(12) United States Patent
Thomas, III et al.

(10) Patent No.: US 12,043,646 B2
(45) Date of Patent: *Jul. 23, 2024

(54) METHODS AND SYSTEMS FOR SOLID PHASE PEPTIDE SYNTHESIS

(71) Applicant: Massachusetts Institute of Technology, Cambridge, MA (US)

(72) Inventors: Dale Arlington Thomas, III, Hampden, ME (US); Alexander James Mijalis, Shreveport, LA (US); Bradley L. Pentelute, Revere, MA (US); Mark David Simon, Gainesville, FL (US); Surin Mong, Ann Arbor, MI (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/068,838

(22) Filed: Dec. 20, 2022

(65) Prior Publication Data

US 2023/0279045 A1 Sep. 7, 2023

Related U.S. Application Data

(63) Continuation of application No. 16/874,824, filed on May 15, 2020, now Pat. No. 11,584,776, which is a continuation of application No. 15/268,032, filed on Sep. 16, 2016, now Pat. No. 10,683,325.

(60) Provisional application No. 62/220,233, filed on Sep. 17, 2015.

(51) Int. Cl.
| | |
|---|---|
| C07K 1/04 | (2006.01) |
| C07K 7/06 | (2006.01) |
| C07K 14/47 | (2006.01) |
| C07K 14/60 | (2006.01) |
| C07K 14/61 | (2006.01) |
| C07K 14/62 | (2006.01) |
| G01N 21/27 | (2006.01) |
| G01N 21/33 | (2006.01) |
| G01N 21/3577 | (2014.01) |
| G01N 21/84 | (2006.01) |
| G01N 33/487 | (2006.01) |

(52) U.S. Cl.
CPC ............ *C07K 1/045* (2013.01); *C07K 7/06* (2013.01); *C07K 14/47* (2013.01); *C07K 14/60* (2013.01); *C07K 14/61* (2013.01); *C07K 14/62* (2013.01); *G01N 21/33* (2013.01); *G01N 33/48707* (2013.01); *G01N 21/272* (2013.01); *G01N 21/3577* (2013.01); *G01N 2021/8416* (2013.01)

(58) Field of Classification Search
None
See application file for complete search history.

(56) References Cited

U.S. PATENT DOCUMENTS

| | | | |
|---|---|---|---|
| 4,192,796 | A | 3/1980 | Mosby et al. |
| 4,192,798 | A | 3/1980 | Verlander et al. |
| 4,668,476 | A | 5/1987 | Bridgham et al. |
| 4,746,490 | A | 5/1988 | Saneii |
| 4,816,513 | A | 3/1989 | Bridgham et al. |
| 5,807,525 | A | 9/1998 | Allen et al. |
| 6,028,172 | A | 2/2000 | Stepaniuk et al. |
| 6,033,631 | A | 3/2000 | Zuckermann et al. |
| 7,348,404 | B2 | 3/2008 | Holm et al. |
| 7,902,488 | B2 | 3/2011 | Collins et al. |
| 8,206,593 | B2 | 6/2012 | Lee et al. |
| 8,535,947 | B2 | 9/2013 | Menakuru |
| 8,614,289 | B2 | 12/2013 | Acemoglu et al. |

(Continued)

FOREIGN PATENT DOCUMENTS

| | | |
|---|---|---|
| CN | 101665528 A | 3/2010 |
| CN | 102924568 A | 2/2013 |

(Continued)

OTHER PUBLICATIONS

Canadian Office Action mailed Nov. 16, 2022, for Application No. CA 2,999,031.
Chinese Office Action mailed Jan. 6, 2021, for Application No. CN 201680067354.5.
Extended European Search Report dated Mar. 22, 2019, for Application No. EP 16847419.5.
European Office Action mailed Oct. 16, 2020, for EP Application No. 16847419.5.

(Continued)

*Primary Examiner* — Christina Bradley
(74) *Attorney, Agent, or Firm* — Wolf, Greenfield & Sacks, P.C.

(57) ABSTRACT

Methods and systems for control of solid phase peptide synthesis are generally described. Control of solid phase peptide synthesis involves the use of feedback from one or more reactions and/or processes (e.g., reagent removal) taking place in the solid phase peptide synthesis system. In some embodiments, a detector may detect one or more fluids flowing across a detection zone of a solid phase peptide synthesis system and one or more signals may be generated corresponding to the fluid(s). For instance, an electromagnetic radiation detector positioned downstream of a reactor may detect a fluid exiting the reactor after a deprotection reactor and produce a signal(s). In some embodiments, based at least in part on information derived from the signal(s), a parameter of the system may be modulated prior to and/or during one or more subsequent reactions and/or processes taking place in the solid phase peptide synthesis system. In some embodiments, the methods and systems, described herein, can be used to conduct quality control to determine and correct problems (e.g., aggregation, truncation, deletion) in reactions (e.g., coupling reactions) taking place in the solid phase peptide synthesis system.

19 Claims, 27 Drawing Sheets

Specification includes a Sequence Listing.

(56) References Cited

U.S. PATENT DOCUMENTS

| | | | |
|---|---|---|---|
| 8,835,179 | B2 | 9/2014 | Chang et al. |
| 9,169,287 | B2 | 10/2015 | Simon et al. |
| 9,669,380 | B2 | 6/2017 | Collins et al. |
| 9,695,214 | B2 | 7/2017 | Simon et al. |
| 9,868,759 | B2 | 1/2018 | Simon et al. |
| 10,683,325 | B2 | 6/2020 | Thomas, III et al. |
| 10,889,613 | B2 | 1/2021 | Simon et al. |
| 11,584,776 | B2 * | 2/2023 | Thomas, III ............ C07K 14/47 |
| 2012/0080608 | A1 | 4/2012 | Menakuru et al. |
| 2014/0275481 | A1 | 9/2014 | Simon et al. |
| 2015/0217254 | A1 | 8/2015 | Boroomand |
| 2016/0031931 | A1 | 2/2016 | Simon et al. |
| 2016/0102118 | A1 | 4/2016 | Simon et al. |
| 2017/0081358 | A1 | 3/2017 | Thomas, III et al. |
| 2017/0081359 | A1 | 3/2017 | Thomas, III et al. |
| 2018/0057525 | A1 | 3/2018 | Simon et al. |
| 2018/0066012 | A1 | 3/2018 | Simon et al. |

FOREIGN PATENT DOCUMENTS

| | | |
|---|---|---|
| CN | 103048395 A | 4/2013 |
| EP | 1923396 A2 | 5/2008 |
| JP | 59-161322 A | 9/1984 |
| JP | 60-237097 A | 11/1985 |
| JP | 2000-511934 A | 9/2000 |
| JP | 2001-527544 A | 12/2001 |
| JP | 2005-015483 A | 1/2005 |
| JP | 2008-110977 A | 5/2008 |
| JP | 2018-528965 A | 10/2018 |
| WO | WO 82/03077 A1 | 9/1982 |
| WO | WO 98/34633 A1 | 8/1998 |
| WO | WO 2014/149387 A2 | 9/2014 |

OTHER PUBLICATIONS

Japanese Office Action mailed Aug. 31, 2020, for Application No. JP2018-514412.
International Search Report and Written Opinion mailed Dec. 7, 2016, for Application No. PCT/US2016/052200.
International Preliminary Report on Patentability dated Mar. 29, 2018, for Application No. PCT/US2016/052200.
[No Author Listed] Apogee: Totally automated single peptide synthesizer. Advanced Automated Peptide Protein Technologies. Product Description. 2006. Louisville, KY. 4 pages.
[No Author Listed] Applied Biosystems User Bulletin No. 35: Model 431A Peptide Synthesizer. Nov. 1993. 26 pages. updated Jul. 2002.
[No Author Listed], Applied Biosystems User Bulletin: Model 433A Peptide Synthesizer and Series 200 UV Detector, UV Monitoring Guide. 2004: 236 pages.
[No Author Listed], ABI 433A Peptide Synthesizer: User Guide. vol. 1 of 2. 2004; 376 pages.
[No Author Listed] Bachem: The Bachem Practice of SPPS. Edition 2005. 84 pages.
[No Author Listed] Endeavor 90: Tabletop peptide synthesizer. Advanced Automated Peptide Protein Technologies. Product Description. 2006. Louisville, KY. 4 pages.
[No Author Listed], ERBI Directory 2010, 192 pages.
[No Author Listed] Focus XC: Automated peptide synthesizer. Advanced Automated Peptide Protein Technologies. Product Description. 2006. Louisville, KY. 5 pages.
[No Author Listed] Liberty 1: Advantages. CEM Corporation. 2011. Last accessed online at <http://www.cem.com/liberty-1-advantages.html> on May 9, 2013. 2 pages.
[No Author Listed] Liberty Blue. Microwave Peptide Synthesizer: peptide synthesis made fast and efficient. CEM Sales Literature LibBlue B105, accessible via: www.brs.be/pdf/525_broch_libblue_b105.pdf; dated Feb. 18, 2010. 9 pages.
[No Author Listed] Liberty. Microwave Peptide Synthesis. CEM Sales Literature Liberty, accessible via: www.cem.hu/pdf/liberty_eng.pdf; dated Mar. 6, 2005. 3 pages.
[No Author Listed] Liberty: Advantages. CEM Corporation. 2011. Last accessed online at <http://www.cem.com/liberty-advantages.html> on May 9, 2013. 3 pages.
[No Author Listed] Liberty: Liberty Overview. CEM Corporation. 2011. Last accessed online at <http://www.cem.com/liberty.html> on May 9, 2013. 2 pages.
[No Author Listed], Peptide synthesis and applications. Methods in Molecular Biology. Ed. Howl, J. 2005:263 pages.
[No Author Listed] PL-Wang Resin, Sales Literature, accessible via: www.cypress-international.com/imagepolymerlabs/wang.pdf; dated Apr. 27, 2003. 3 pages.
[No Author Listed] Pseudoproline Dipeptides, Corden Pharma Switzerland, Sales Literature, 2011. 4 pages.
[No Author Listed], CS Bio Specifications for CS336X. Last Accessed Jun. 20, 2016. http://www.csbio.com/peptide-synthesizers/cs-336x. 2 pages.
[No Author Listed], We Have the Art of Peptide Synthesis Down to a Science. 2010. CEM Corporation. Complete Peptide Brochure. 9 pages.
[No Author Listed], Static Mixing, Reaction, Heat Transfer & Fluid Dynamics Technology. Stamixco. Jul. 18, 2007. 8 pages.
[No Author Listed], Synthesis of Crosslinked Polymers, Chapter 4, Results and Discussion, Jun. 18, 2010, available online at: http://shodhganga.inflibnet.ac.in/bitstream/10603/146/11/11_chapter4.pdf. 102 pages.
[No Author Listed], PubChem Compound Summary for CID: 8083, Morpholine. https://pubchem.ncbi.nlm.nih.gov/compound/8083#section=Chemical-and-Physi-cal-Properties. 2018. 98 pages.
Adamo et al., On-demand continuous-flow production of pharmaceuticals in a compact, reconfigurable system. Science. Apr. 1, 2016;352(6281):61-7. doi: 10.1126/science.aaf1337.
Al-Warhi, Recent development in peptide coupling reagents. J Saudi Chem Soc. 2012;16:97-116. Epub Jan. 5, 2011.
Bacsa et al., Rapid solid-phase synthesis of a calmodulin-binding peptide using controlled microwave irradiation. Nature Protocols. 2007; 2(9):2222-2227.
Basca et al., Rapid solid-phase peptide synthesis using thermal and controlled microwave irradiation. J Pept Sci. Oct. 2006;12(10):633-8.
Bayer et al., Polystyrene-immobilized PEG chains: Dynamics and application in peptide synthesis, immunology, and chromatography. Ch. 20. In: Harris, J.M. (eds). Poly(Ethylene Glycol) Chemistry. Biotechnical and biomedical applications. Springer,Boston. 1992;325-45.
Bedford et al., Amino acid structure and "difficult sequences" in solid phase peptide synthesis. Int J Pept Protein Res. Sep.-Oct. 1992;40(3-4):300-7.
Carpino et al., Synthesis of "Difficult" Peptide Sequences : Application of a Depsipeptide Technique to the Jung-Redemann 10- and 26-mers and the Amyloid Peptide Abeta(1-42). Tetrahedron Lett. 2004;45:7519-23.
Carter et al., ReactIR Flow Cell: A New Analytical Tool for Continuous Flow Chemical Processing. Org Process Res Dev. 2010;14(2):393-404.
Cen et al., Progress on synthesis of peptide by microwave irradiation. Chemical World. Jul. 2009;2009-07:439-42.
Coin et al., Solid-phase peptide synthesis: from standard procedures to the synthesis of difficult sequences. Nat Protoc. 2007;2(12):3247-56.
Collins et al., High-efficiency solid phase peptide synthesis (HE-SPPS). Organic Letters. Jan. 23, 2014; 16:940-943.
Collins et al., Microwave energy: a versatile tool for the biosciences. Org Biomol Chem. 2007; 5:1141-1150.
Dang et al., Enhanced Solvation of Peptides Attached to "Solid-Phase" Resins: Straightforward Syntheses of the Elastin Sequence Pro-Gly-Val-Gly-Val-Pro-Gly-Val-Gly-Val. Org Lett. Jul. 17, 2015;17(14):3521-3. doi: 10.1021/acs.orglett.5b01632. EpubJun. 25, 2015.
Dettin et al., SPPS of difficult sequences. J Peptide Res. 1997;49:103-11.

(56) References Cited

OTHER PUBLICATIONS

Dryland et al., Peptide synthesis. Part 11. A system for continuous flow solid phase peptide synthesis using fluorenylmethoxycarbonyl-amino acid pentafluorophenyl esters. Tetrahedron. 1988;44(3):859-76.

Dryland et al., Peptide synthesis. Part 8. A system for solid-phase synthesis under low pressure continuous flow conditions. J Chem Soc, Perkin Trans 1. Jan. 1, 1986:125-37.

Finneman et al., Novel approach for optimization of a 'difficult' peptide synthesis by utilizing quantitative reaction monitoring assays. J Pept Sci. 2012;18:511-8.

Fuentes et al., Fast conventional synthesis of .sup.65-74ACP on the Symphony.RTM. and Prelude. TM. Protein Technologies, Inc. Tuscon, AZ. 1 page. 2006.

Fuse et al., Efficient amide bond formation through a rapid and strong activation of carboxylic acids in a microflow reactor. Angew Chem Int Ed. 2014;53:851-5.

Goodman et al., Synthesis of Peptides and Peptidomimetics. New York: Thieme Stuttgart. 2004; vol. E22a; Section 2.1 Amino Group. p. 65.

Goodman et al., Synthesis of Peptides and Peptidomimetics. New York: Thieme Stuttgart. 2004; vol. E22b; Section 5.3 Examples of Protein Synthesis on Solid Support. p. 65.

Goodman et al., Synthesis of Peptides and Peptidomimetics. New York: Thieme Stuttgart. 2004; vol. E22c; Section 9.2 Synthesis of Peptides Containing Proline Analogues. p. 65.

Gude et al., An accurate method for the quantitation of Fmoc-derivatized solid phase supports. Letters in Peptide Science; Jul. 2002; 9(4-5): 203-206.

Han et al., Occurrence and minimization of cysteine racemization during stepwise solid-phase peptide synthesis 1, 2. J Org Chem. Jul. 1997.;62(13):4307-12.

Hjorringgaard et al., Evaluation of COMU as a coupling reagent for in situ neutralization Boc solid phase peptide synthesis. J Pept Sci. Mar. 2012;18(3):199-207. doi: 10.1002/psc.1438. Epub Jan. 17, 2012.

Hood et al., Fast conventional Fmoc solid-phase peptide synthesis with HCTU. J Pept Sci. Jan. 2008;14(1):97-101. Published online Sep. 24, 2007 in Wiley InterScience.

Johnson et al., A reversible protecting group for the amide bond in peptides. Use in the synthesis of 'difficult sequences'. J Chem Soc Chem Commun. 1993;29(4):369-72.

Kaiser et al., Color test for detection of free terminal amino groups in the solid-phase synthesis of peptides. Anal Biochem. Apr. 1970;34(2):595-8.

Kent, Chemical synthesis of peptides and proteins. Annu Rev Biochem. 1988:57-:957-89.

Krchnak et al., Continuous-flow solid-phase peptide synthesis. Tetrahedron Letters. 1987;28(38):4469-4472.

Latassa et al., Abstract: AKTA™ oligopilot™ for Automated Solid Phase Peptide Synthesis. LONZA. Poster presented at the 30th European Peptide Symposium in Helsinki, Finlandia Hall. Aug. 31, 2008:132-3.

Latassa et al., AKTA™ oligopilot™ for Automated Solid Phase Peptide Synthesis. LONZA. Poster presented at the 30th European Peptide Symposium in Helsinki, Finlandia Hall. Aug. 31, 2008. 8 pages.

Lukas et al., Solid-phase peptide synthesis under continuous-flow conditions. Proc Natl Acad Sci USA. May 1981;78(5):2791-5.

Made et al., Automated solid-phase peptide synthesis to obtain therapeutic peptides. Beilstein J Org Chem. May 22, 2014;10:1197-212. doi: 10.3762/bjoc.10.118.

Malik et al., Microwave-assisted solid-phase peptide synthesis using the biotage syro Wave™. Chapter 16. Peptide Synthesis and Applications. Methods in Molecular Biology. Eds. Jenson et al., 2011: 225-34.

McQuade et al., Applying flow chemistry: methods, materials, and multistep synthesis. J Org Chem. Jul. 5, 2013;78(13):6384-9. doi: 10.1021/jo400583m. Epub Jun. 10, 2013.

Meldal et al., PEGA: A flow stable polyethylene glycol dimethyl acrylamide copolymer for solid phase synthesis. Tetrahedron Letters. May 19, 1992;33(21):3077-80.

Merrifield et al., Solid Phase Peptide Synthesis I. The Synthesis of a Tetrapeptide. J Am Chem Soc. Jul. 20, 1963; 85:2149-54.

Miranda et al., Accelerated chemical synthesis of peptides and small proteins. Proc Natl Acad Sci U S A. Feb. 16, 1999;96(4):1181-6.

Mong et al., Rapid total synthesis of DARPin pE59 and barnase. Chembiochem. Mar. 21, 2014;15(5):721-33. doi: 10.1002/cbic.201300797. Epub Mar. 11, 2014.

Pedersen et al., Instruments for automated peptide synthesis. Peptide Synthesis and Applications. Methods in Molecular Biology. Eds. Jensen et al., 2011; 215-24.

Pedersen et al., Microwave heating in solid-phase peptide synthesis. Chem Soc Rev. 2012;41:1826-44. Published online Oct. 20, 2011 on http://pubs.rsc.org.

Quade, Solid Phase Peptide Synthesis, Strategies and Resins, modified on May 28, 2006, available online at: http://wwwoc. chemie. uni-regensburg.de/OCP/ch/chv/oc22/script/006.pdf. 12 pages.

Quibell et al., Preparation and purification of beta-Amyloid (1-43) via soluble, amide backbone protected intermediates. J Org Chem. Mar. 1994;59(7):1745-50.

Razzaq et al., Continuous-flow microreactor chemistry under high-temperature/pressure conditions. Eur J Org Chem. 2009;2009(9):1321-5.

Reid et al., Automated solid-phase peptide synthesis: use of 2-(1H-benzotriazol-1-yl)-1,1,3,3-tetramethyluronium tetrafluoroborate for coupling of tert-butyloxycarbonyl amino acids. Anal Biochem. Feb. 1, 1992;200(2):301-9.

Sabatino et al., Advances in automatic, manual and microwave-assisted solid-phase peptide synthesis. Curr Opin Discov Devel. Nov. 2008;11(6):762-70. Abstract Only. 1 page.

Sarin et al., Quantitative monitoring of solid-phase peptide synthesis by the ninhydrin reaction. Anal Biochem. Oct. 1981;117(1):147-57.

Schnolzer et al., In situ neutralization in boc-chemistry solid phase peptide synthesis. International Journal of Peptide Research and Therapeutics. 1992;40:180-193. Published online Jun. 2007.

Simon et al., Rapid flow-based peptide synthesis. Chembiochem. Mar. 21, 2014;15(5):713-20. doi:10.1002/cbic.201300796. Epub Mar. 11, 2014.

Sucholeiko et al., New developments in solid phase synthesis supports. Mol Div. Jan. 1, 1998;4:25-30.

Tedebark et al., AKTA™ oligopilot™ for Automated Solid Phase Peptide Synthesis. Proceedings of the 30th European Peptide Symposium in Helsinki, Finlandia Hall. Aug. 10, 2010:450-1.

Vanier, Microwave-assisted solid-phase peptide synthesis based on the Fmoc protecting group strategy (CEM). Peptide synthesis and applications. Methods in Molecular Biology. Eds. Jensen et al., 2011; 235-50.

Varanda et al., Solid-phase peptide synthesis at elevated temperatures: a search for and optimized synthesis condition of unsulfated cholecystokinin-12. J Pept Res. Aug. 1997;50(2):102-8.

Wang et al., Temperature effects on reaction rates for solid phase peptide synthesis. Chem Engin Sci. Jan. 29, 1991; 46(9):2373-6.

Wohr et al., Pseudo-prolines in peptide synthesis: Direct insertion of serine and threonine derived oxazolidines in dipeptides. Tetrahedron Lett. May 29, 1995;36(22):3847-8.

Yoshida et al., Flash chemistry: flow chemistry that cannot be done in batch. Chem Commun (Camb). Nov. 4, 2013;49(85):9896-904. doi: 10.1039/c3cc44709j. Epub Aug. 29, 2013.

Yu et al., Enhanced coupling efficiency in solid-phase peptide synthesis by microwave irradiation. J Org Chem. Aug. 1, 1992;57(18):4781-4.

CA2999031, Nov. 16, 2022, Canadian Office Action.
CN 2016800673545, Jan. 6, 2021, Chinese Office Action.
EP16847419.5, Mar. 22, 2019, Extended European Search Report.
EP16847419.5, Oct. 16, 2020, European Office Action.
JP 2018-514412, Aug. 31, 2020, Japanese Office Action.
PCT/US2016/052200, Dec. 7, 2016, International Search Report and Written Opinion.

(56) References Cited

OTHER PUBLICATIONS

PCT/US2016/052200, Mar. 29, 2018, International Preliminary Report on Patentability.

* cited by examiner

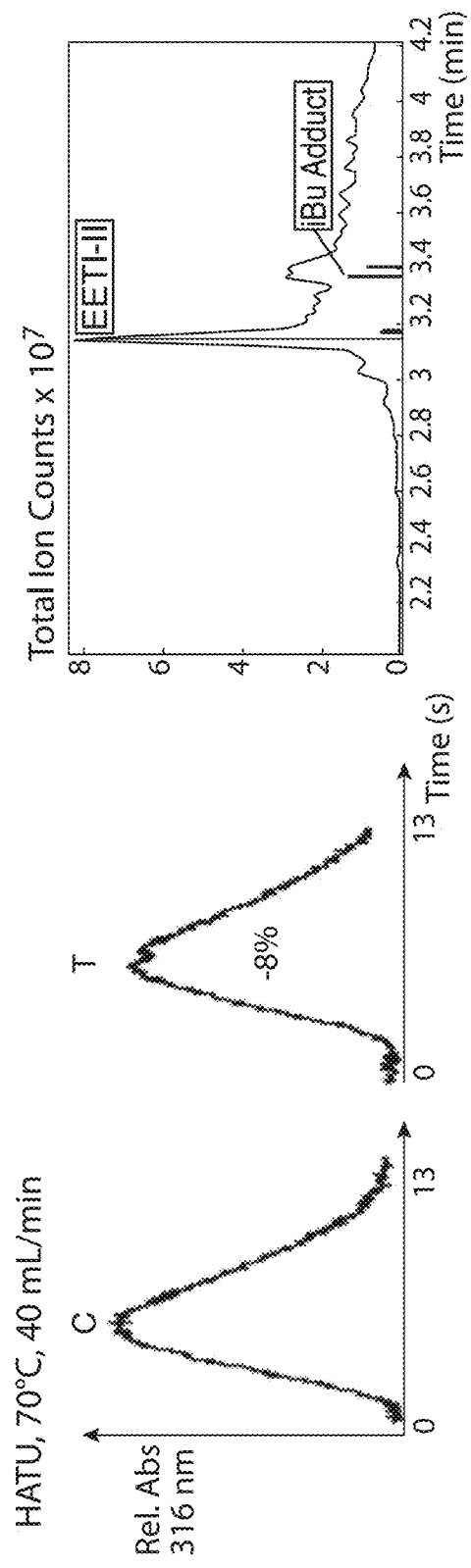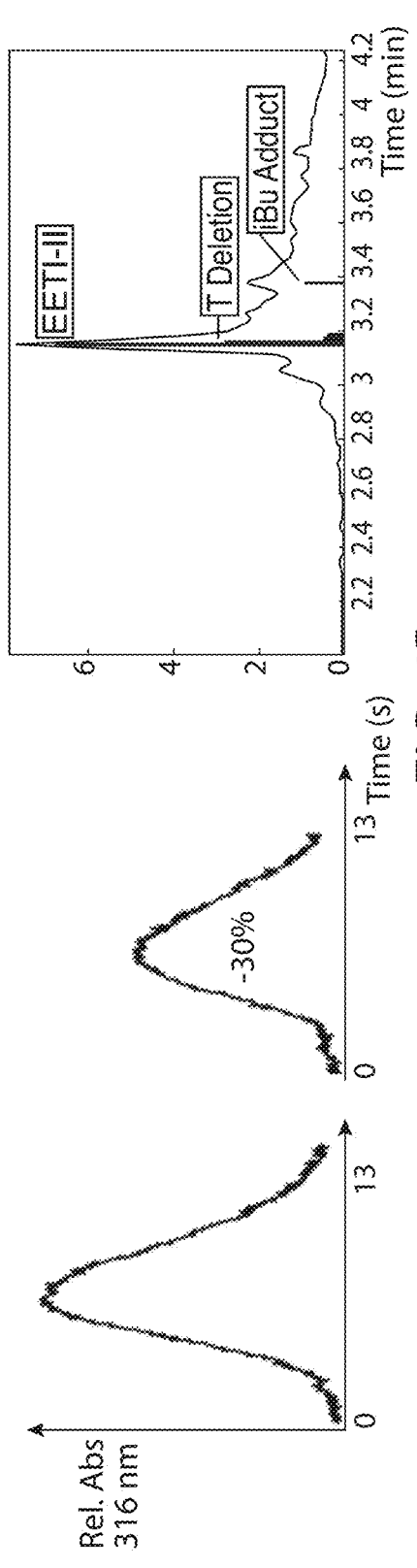

SEQUENCE LISTING

```
Sequence total quantity: 6
SEQ ID NO: 1            moltype = AA  length = 32
FEATURE                 Location/Qualifiers
REGION                  1..32
```

```
                    note = Synthetic polypeptide
source              1..32
                    mol_type = protein
                    organism = synthetic construct
SEQUENCE: 1
GCPRPRGDNP PLTCKQDSDC LAGCVCPNGF CG                              32

SEQ ID NO: 2        moltype = AA   length = 10
FEATURE             Location/Qualifiers
REGION              1..10
                    note = Synthetic polypeptide
source              1..10
                    mol_type = protein
                    organism = synthetic construct
SEQUENCE: 2
WFTTLISTIM                                                       10

SEQ ID NO: 3        moltype = AA   length = 11
FEATURE             Location/Qualifiers
REGION              1..11
                    note = Synthetic polypeptide
source              1..11
                    mol_type = protein
                    organism = synthetic construct
SEQUENCE: 3
TMGTTLISTI M                                                     11

SEQ ID NO: 4        moltype = AA   length = 10
FEATURE             Location/Qualifiers
REGION              1..10
                    note = Synthetic polypeptide
source              1..10
                    mol_type = protein
                    organism = synthetic construct
SEQUENCE: 4
VQAAIDYING                                                       10

SEQ ID NO: 5        moltype = AA   length = 29
FEATURE             Location/Qualifiers
REGION              1..29
                    note = Synthetic polypeptide
SITE                29
                    note = Modified by CONH2
source              1..29
                    mol_type = protein
                    organism = synthetic construct
SEQUENCE: 5
YADAIFTNSY RKVLGQLSAR KLLQDILSA                                  29

SEQ ID NO: 6        moltype = AA   length = 30
FEATURE             Location/Qualifiers
REGION              1..30
                    note = Synthetic polypeptide
SITE                30
                    note = Modified by CONH2
source              1..30
                    mol_type = protein
                    organism = synthetic construct
SEQUENCE: 6
FVNQHLCGSH LVEALYLVCG ERGFFYTPKT                                 30
```

METHODS AND SYSTEMS FOR SOLID PHASE PEPTIDE SYNTHESIS

RELATED APPLICATIONS

This application is a continuation of U.S. patent application Ser. No. 16/874,824, filed May 15, 2020, which is a continuation of U.S. patent application Ser. No. 15/268,032, filed Sep. 16, 2016, which claims priority under 35 U.S.C. § 119(e) to U.S. Provisional Application Ser. No. 62/220,233, filed Sep. 17, 2015, each of which is incorporated herein by reference in its entirety for all purposes.

REFERENCE TO AN ELECTRONIC SEQUENCE LISTING

The content of the electronic sequence listing (M092570473US03-SEQ-BXB.xml; Size: 9,319 bytes; and Date of Creation: Dec. 16, 2022) is incorporated herein by reference in its entirety.

TECHNICAL FIELD

Methods and systems for feedback control in solid phase peptide synthesis are generally described.

BACKGROUND

Solid phase peptide synthesis is a process used to chemically synthesize peptides on solid supports. In solid phase peptide synthesis, an amino acid or peptide is bound, usually via the C-terminus, to a solid support. New amino acids are added to the bound amino acid or peptide via coupling reactions. Due to the possibility of unintended reactions, protecting groups are typically used. To date, solid phase peptide synthesis has become standard practice for chemical peptide synthesis. The broad utility of solid phase peptide synthesis has been demonstrated by the commercial success of automated solid phase peptide synthesizers. Though solid phase peptide synthesis has been used for over 30 years, automated solid phase peptide synthesizers that afford a high degree of control over individual coupling reactions and/or minimize side reactions have not yet been developed. Accordingly, improved processes and systems are needed.

SUMMARY

Solid phase peptide synthesis methods and associated systems are generally described. Certain embodiments relate to systems and methods for feedback control. The subject matter of the present invention involves, in some cases, interrelated products, alternative solutions to a particular problem, and/or a plurality of different uses of one or more systems and/or articles.

In one set of embodiments, methods are provided. In one embodiment, a method of operating a peptide synthesis system comprises flowing a fluid stream comprising a deprotection reagent through a reactor after a coupling reaction occurs in the reactor, wherein the reactor comprises a plurality of peptides immobilized on a solid support; detecting an electromagnetic absorbance and/or an electromagnetic emission of the fluid stream at a detection zone positioned downstream of the reactor to produce a signal; and modulating a parameter of the system prior to and/or during a subsequent coupling reaction in the reactor based at least in part on information derived from the signal.

In another embodiment, a method of operating a peptide synthesis system comprises producing a first and a second signal at a detection zone positioned downstream of a peptide synthesis reactor, comparing the first signal to the second signal and/or to a reference signal, and modulating a parameter of the system prior to and/or during a reaction in the reactor based at least in part on information derived from the comparing step, wherein the parameter is selected from the group consisting of a flow rate, a reaction time, a temperature, a reactant type, a reactant concentration, a ratio of reactants, an addition of an additive, and combinations thereof.

In yet another embodiment, a method of forming a peptide in a peptide synthesis system, comprises flowing a fluid stream comprising a deprotection reagent through a reactor after a coupling reaction between an amino acid and an amino acid residue immobilized on a solid support to form a peptide fragment; detecting an electromagnetic absorbance and/or an electromagnetic emission of the fluid stream at a detection zone positioned downstream of the reactor to produce a signal; and modulating a parameter of the system prior to formation of the peptide in the reactor based at least in part on an intensity component and a time component derived from the signal, wherein the peptide comprises the peptide fragment.

In another set of embodiments, peptide synthesizer systems are provided. In one embodiment, a peptide synthesizer system comprises a first reagent reservoir connected to a first reagent channel, a second reagent reservoir connected to a second reagent channel, a peptide synthesis reactor positioned downstream of and fluidically connected to the first and second reagent reservoirs, a delivery channel connected to the reactor, wherein the first and second channels are each upstream of and fluidly connected to the delivery channel at a junction, an effluent channel downstream of and fluidically connected to the reactor, an electromagnetic radiation detector connected to and downstream of the effluent channel, and a controller in electrical communication with the electromagnetic radiation detector, wherein the controller is configured control one or more parameters of the system.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 6A is 0 UV traces of dibenzofulvene signals and a mass spectrum from the synthesis of EETI-II when using HATU, according to certain embodiments;

FIG. 6B is UV traces of dibenzofulvene signals and a mass spectrum from the synthesis of EETI-II when using HATU, according to certain embodiments;

DETAILED DESCRIPTION

Figure 1A:
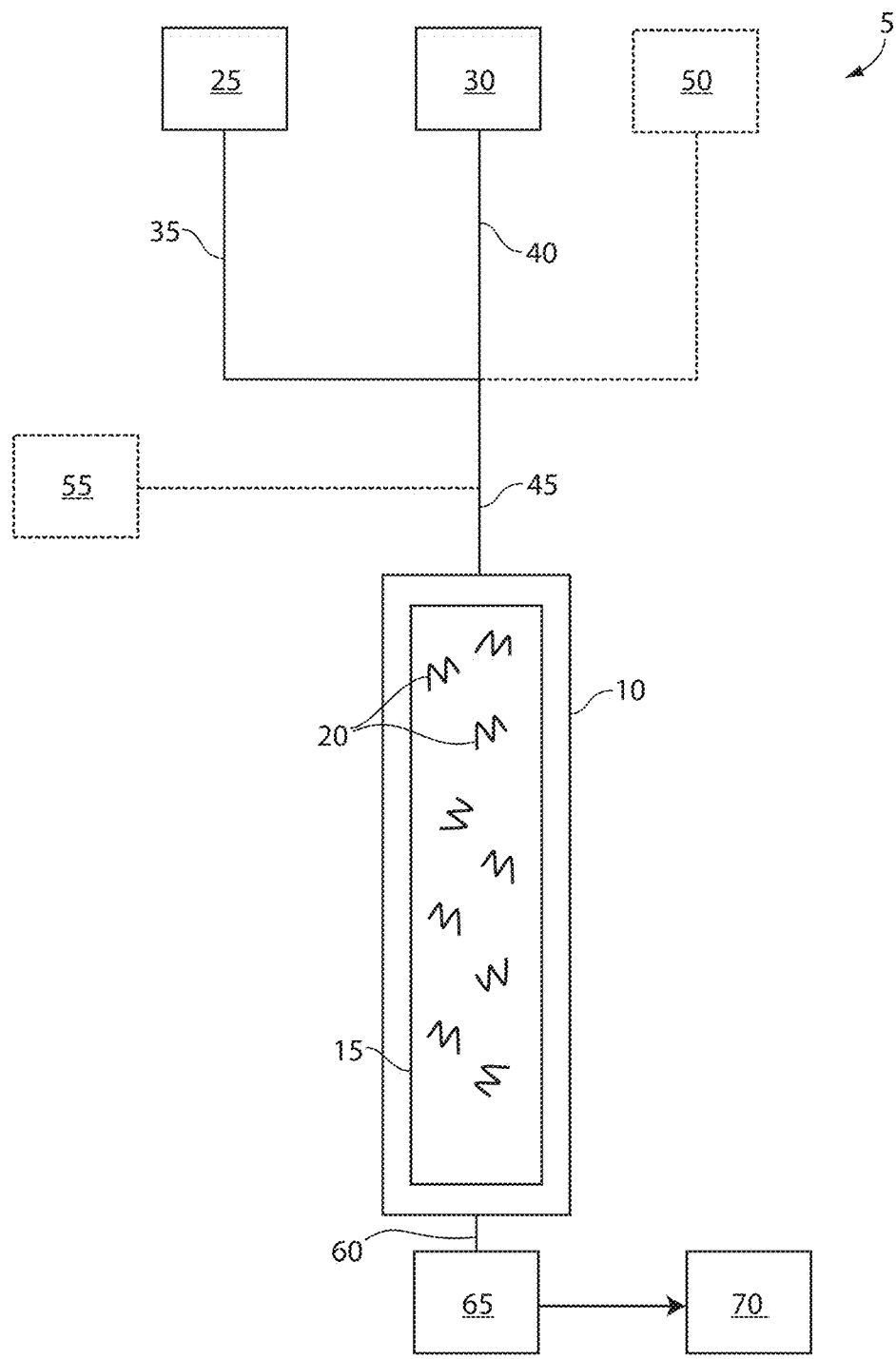
FIG. 1A is a schematic illustration of a system for performing peptide synthesis, according to one set of embodiments.

Methods and systems for control of solid phase peptide synthesis are generally described. Control of solid phase peptide synthesis involves the use of feedback from one or more reactions and/or processes (e.g., reagent removal) taking place in the solid phase peptide synthesis system. In some embodiments, a detector may detect one or more fluids flowing across a detection zone of a solid phase peptide synthesis system and one or more signals may be generated corresponding to the fluid(s). For instance, an electromagnetic radiation detector positioned downstream of a reactor may detect a fluid exiting the reactor after a deprotection reaction and produce a signal(s). In some embodiments, based at least in part on information derived from the signal(s), a parameter of the system may be modulated prior to and/or during one or more subsequent reactions and/or processes taking place in the solid phase peptide synthesis system. In some embodiments, the methods and systems, described herein, can be used to conduct quality control to determine and correct problems (e.g., aggregation, truncation, deletion) in reactions (e.g., coupling reactions) taking place in the solid phase peptide synthesis system.

Solid phase peptide synthesis is a known process in which amino acid residues are added to peptides that have been immobilized on a solid support. In general, solid phase peptide synthesis comprises repeating amino acid addition cycles. Each amino acid additional cycle is intended to add a single amino acid residue to the peptide. The amino acid addition cycle may comprise a deprotection reaction, a coupling reaction, and one or more optional reagent removal (e.g., wash) steps after each reaction. Since peptides are synthesized one amino acid at a time, the yield of each amino acid addition cycle significantly impacts the overall yield for the peptide. For example, in the synthesis of a peptide containing 26 amino acids, a problem in the coupling reaction during the third amino acid addition cycle, such as capping by an activating agent, may prevent subsequent coupling reactions without corrective and result in a 0% yield for the peptide. As another example, the general reaction conditions selected for all coupling reactions in a solid phase peptide synthesis system may be inappropriate for certain amino acids and resulting in lower coupling yields for addition of those amino acids and accordingly a lower overall yield. There is a need for solid phase peptide synthesis methods and systems that are capable of conducting quality control to determine and correct problems occurring in the solid phase peptide synthesis system.

Some conventional solid phase peptide synthesis systems have tried to address this problem by periodically monitoring the effluent from the reactor for indication that the reaction should be stopped. However, many of these conventional systems are unable to identify the problem occurring in reactions, translate the results of monitoring into corrective action, and/or take corrective action based on information derived from monitoring without the need for complex and/or costly methods and equipment.

Certain inventive concepts relate to methods and systems for solid phase peptide synthesis that allow for the identification of a problem occurring in certain reactions, the translation of the results of monitoring into corrective action, and/or implementation of the corrective action based at least in part on information derived from monitoring. FIG. 1 is a schematic illustration of an exemplary system 5 which can be used to perform certain of the inventive methods described herein. The systems and methods described herein (e.g. system 5 in FIG. 1) can, in certain embodiments, involve flow-based synthesis (as opposed to batch-based synthesis, which is employed in many traditional solid phase peptide synthesis systems). In some such embodiments, continuous peptide synthesis can be performed, in which fluid (of one form or another) is substantially continuously transported through the reactor and over a detection zone. For example, reagents and rinsing fluids may be alternatively and continuously transported over the detection zone, in certain embodiments.

In some embodiments, a solid phase peptide synthesis system 5 may comprise a reactor 10. The reactor may comprise peptides 20 immobilized on a solid support 15. In some embodiments, and as shown in FIG. 1, reagent reservoirs (e.g., 25, 30) may be located upstream of and fluidically connected to reactor 10. For example, a first reagent reservoir 25 and a second reagent reservoir 30 may be fluidically connected to the reactor via first reagent channel 35 and second reagent channel 40, respectively, which connect to delivery channel 45 that is connected to reactor 10. The reagent reservoirs may contain at least a portion of the reagents necessary for peptide synthesis. For instance, reagent reservoir 25 may contains amino acids and reagent reservoir 30 may contain an activating agent (e.g., an uronium activating agent). The system may also comprise optional reagent reservoir 50 that may contain a base and/or optional reagent reservoir 55 that may contain a deprotection reagent, such as piperidine or trifluoroacetic acid. The system may also comprise an optional reagent reservoir, not shown, fluidically connected to the reactor that may contain a solvent, such as dimethylformamide (DMF), that may be used, e.g., in a reagent removal step.

In some embodiments, a solid phase peptide synthesis system 6 may comprise a reactor configured to promote and/or facilitate one or more chemical reactions between molecules. For instance, as shown in FIG. 1B, system 6 may comprise reactor 8 configured to promote and/or facilitate one or more chemical reactions between certain reagents and/or reaction products thereof by, e.g., modulating the reaction kinetics and/or reaction time. For example, reactor 8 may be configured to allow the temperature profile of the fluid stream in the reactor to be controlled such that one or more temperature dependent reaction rates can be modulated (e.g., increased, maintained, and/or decreased) to achieve the desired reaction rate(s), reaction product(s), amount of reaction product(s), and/or reaction yield(s). In some embodiments, and as shown in FIG. 1B, reagent reservoirs (e.g., 16, 18) may be located upstream of and fluidically connected to reactor 8. For example, a first reagent reservoir 16 and a second reagent reservoir 18 may be fluidically connected to the reactor via first reagent channel 22 and second reagent channel 24, respectively, which connect to delivery channel 26 that is connected to reactor 8. The reagent reservoirs may contain at least a portion of the reagents necessary for peptide synthesis. For instance, reagent reservoir 16 may contains amino acids and reagent reservoir 30 may contain an activating agent (e.g., an uronium activating agent). The system may also comprise optional reagent reservoir 28A that may contain a base and/or optional reagent reservoir 28B that may contain a deprotection reagent, such as piperidine or trifluoroacetic acid. The system may also comprise an optional reagent reservoir, not shown, fluidically connected to the reactor that may contain a solvent, such as dimethylformamide (DMF), that may be used, e.g., in a reagent removal step.

In some embodiments, reactor 8 may configured to promote and/or facilitate a chemical reaction between reagents from one or more reservoirs located upstream of reactor 8, between a reaction product of a reagent and a reagent, and/or between reaction products of reagents. In certain embodiments, reactor 8 may facilitate and/or promote a chemical reaction between two or more reagents from reservoirs located upstream of reactor 8. In some embodiments, reactor 8 may be within a heating zone (not shown) or otherwise in communication with a heat source. For example, system 6 may comprise a heating zone (not shown), within which the contents of the fluid stream in reactor 6 may be heated. The heating zone may comprise a heat source, such as a heater. In general, any suitable method of heating may be used to control the temperature of the fluid stream in the reactor. For example, the heating zone may comprise a liquid bath (e.g., a water bath), a resistive heater, a gas convection-based heating element, a microwave heating element, or any other suitable device designed to produce heat upon the application of energy or due to a chemical reaction. In some embodiments, system 6 may comprise two or more reactors. For example, as shown in FIG. 1B, system 6 may comprise reactor 8 upstream of reactor 12. In certain embodiments, reactor 8 may not comprise a plurality of amino acids immobilized and/or a plurality of peptides immobilized on a solid support. In some such cases, the formation of one or more amino acid residue may not occur in reactor 8. In some embodiments, the formation of one or more amino acid residue may occur in reactor 12. In some such embodiments, reactor 12 may contain peptides and/or amino acids immobilized on a solid support. For example, as shown in FIG. 1B, peptides 14 may be immobilized on a solid support 13. Solid support 13 may be contained within reactor 8.

Figure 1B:
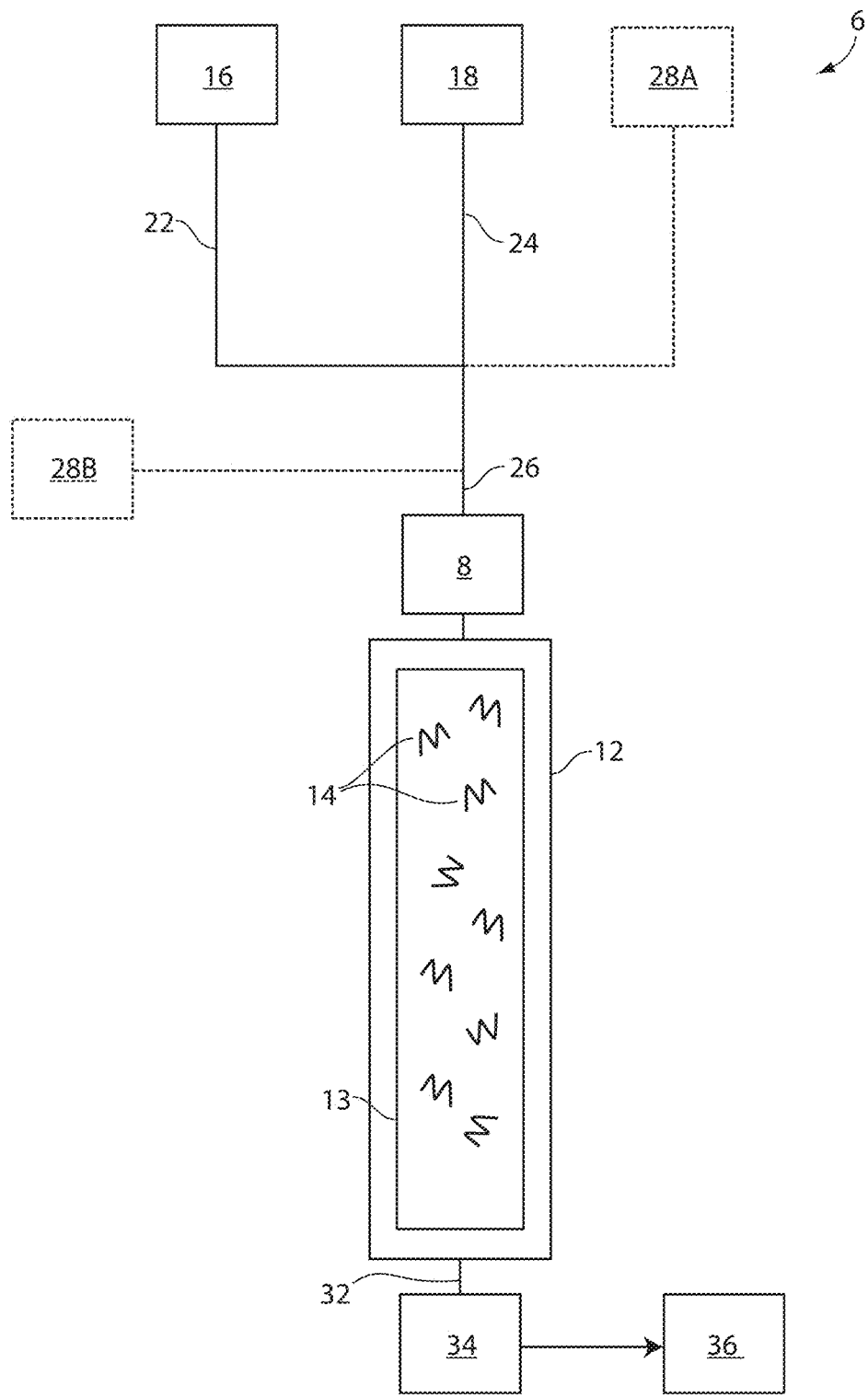
FIG. 1B is a schematic illustration of a system for performing peptide synthesis, according to one set of embodiments.

While single reservoirs have been illustrated in FIGS. 1A and 1B for simplicity, it should be understood that in FIGS. 1A and 1B, where single reservoirs are illustrated, multiple reservoirs (e.g., each containing different types of amino acids, different types of activating agents, different types of deprotection agents, different types of bases, etc.) could be used in place of the single reservoir.

In some embodiments, peptide synthesis comprising flowing fluid streams, e.g., from the reagent reservoirs through a reactor (e.g., 8, 10). For example, a fluid stream comprising a deprotection reagent may be flowed through the reactor after a coupling reaction. Fluid may exit the reactor through effluent channel connected to the reactor. The effluent channel may be fluidically connected to a detection zone (e.g., 34, 65). In certain embodiment, the effluent channel (e.g., 32, 60) may be not comprise a separation element (e.g., size-exclusion column, affinity column) and/or may be connected to the detection zone.

In some embodiments, the detection zone (e.g., 34, 65) may comprise one or more electromagnetic radiation detectors. The detector(s) may measure the electromagnetic absorbance and/or the electromagnetic emission of one or more fluids exiting the reactor and produce one or more signals corresponding to the fluid(s). The signal(s) may be transmitted to a unit (e.g., 36, 70), which is in electrical communication with the detector(s). In some embodiments, the unit (e.g., 36, 70) may be a controller that is configured control one or more parameters of the system. In such embodiments, the controller may be operatively associated with one or more components (e.g., temperature regulator, fluid flow source) of the system and/or with one or more processors for controlling component(s) of the system. For example, the controller may be operatively associated with one or more processors for controlling flow rate, temperature, selection of reagent type, selection of reagent concentration, reaction time, selection of the ratio of reagents, the addition of an additive, or combinations thereof. Optionally, the controller may also be operatively associated with other components such as a user interface and an external communication unit (e.g., a USB), and/or other components, as described in more detail below. The user interface may be used to display the signal(s), alert the user of a problem with a certain reaction, and/or receive operation instructions from the user.

As used herein, a unit that is "operatively associated with" one or more other components indicates that such components are directly connected to each other, in direct physical contact with each other without being connected or attached to each other, or are not directly connected to each other or in contact with each other, but are mechanically, electrically (including via electromagnetic signals transmitted through space), or fluidically interconnected (e.g., via channels) so as to cause or enable the components so associated to perform their intended functionality. For instance, in some embodiments, the controller may be electronically coupled to a component via a wireless or wired electronic connection. For example, the controller may be electronically coupled via a wireless or wired electronic connection to one or more processors for controlling flow rate, temperature, selection of reagent type, selection of reagent concentration, reaction time, selection of the ratio of reagents, the addition of an additive, or combinations thereof. In certain embodiments, the controller may be electronically coupled via a wireless or wired electronic connection to a temperature regulator for one or more fluid streams and/or the reactor. In some embodiments, the controller may be electronically coupled via a wireless or wired electronic connection to a fluid flow source (e.g., pump) for one or more fluid streams and/or the reactor. In certain embodiments, the controller may be electronically coupled via a wireless or wired electronic connection to one or more processors for controlling one or more selection of reagents (e.g., type, concentration, ratio).

In general, a unit (e.g., controller), such as 36 or 70, may be used to conduct quality control by the use of feedback from one or more reactions and/or processes (e.g., reagent removal step) taking place in the solid peptide synthesis system. For instance, a controller may be configured to receive signal(s) from the one or more detectors, to quantitatively analyze one or more signals or a pattern of signals, to compare one or more signals or a pattern of signals with other signals (e.g., reference signal) or values pre-programmed into the controller, and/or to modulate one or more parameters to control operation of the solid phase peptide synthesis system. Specific examples of feedback control are described in more detail below.

As described herein, certain inventive concepts relate to methods for feedback control in a solid phase peptide synthesis system. In some embodiments, the method may comprise detecting an electromagnetic absorbance and/or an electromagnetic emission of a fluid stream at a detection zone positioned downstream of the reactor during and/or immediately after (e.g., after the stream exits the reactor, but before the next amino acid addition step) a reaction step in an amino acid addition cycle to produce a signal. Based at least in part on information derived from the signal (e.g., an intensity component and a time component derived from the signal), one or more parameter of the system may be modulated prior to and/or during a subsequent reaction (e.g., coupling reaction) in the reactor and/or prior to formation of the peptide in the reactor.

In some embodiments, detecting during a reaction step in an amino acid addition cycle may comprise detecting from the start of the reaction step to the end of the reaction step, detecting during at least a portion of the reaction step (e.g., at least about 20% of the total time for the reaction step, at least about 30% of the total time for the reaction step, at least about 40% of the total time for the reaction step, at least about 50% of the total time for the reaction step, at least about 60% of the total time for the reaction step, or at least about 75% of the total time for the reaction step and less than about 100%), and/or continuous detection during at least a portion of the two or more reaction steps (e.g., deprotection steps) and/or complete peptide synthesis.

Figure 2A:
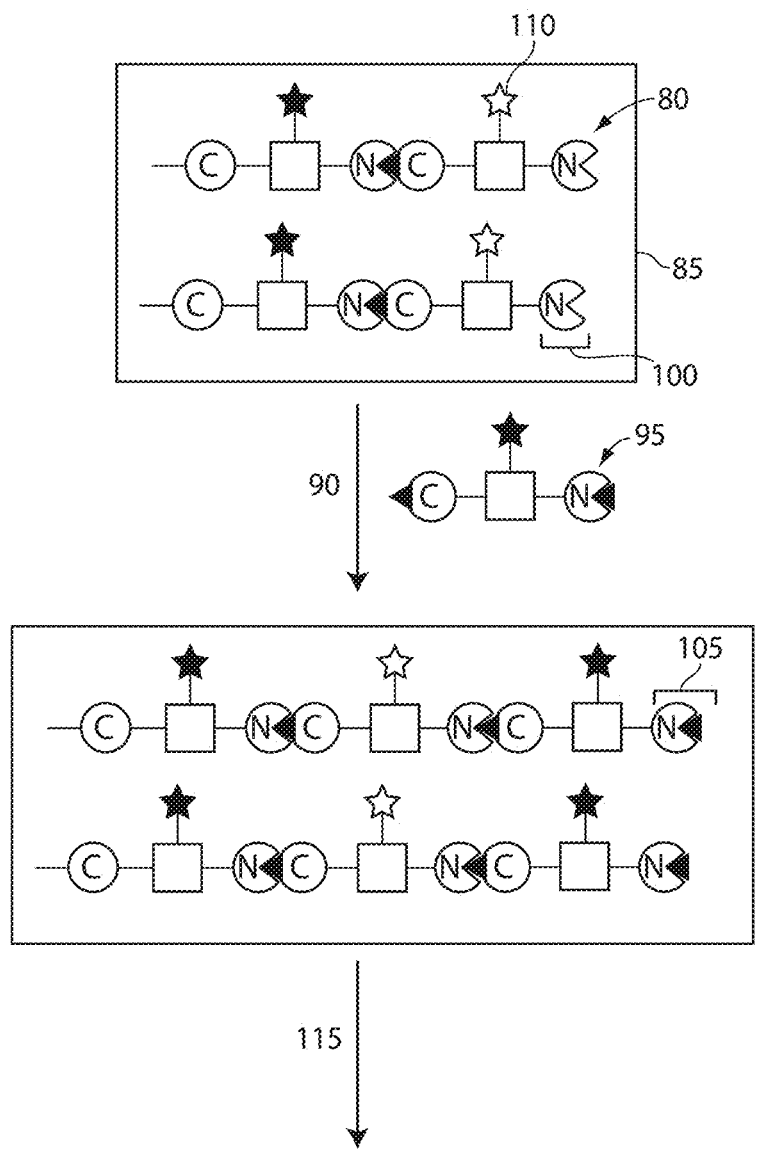
FIG. 2A is a schematic of peptide synthesis, according to certain embodiments.
Figure 2A:
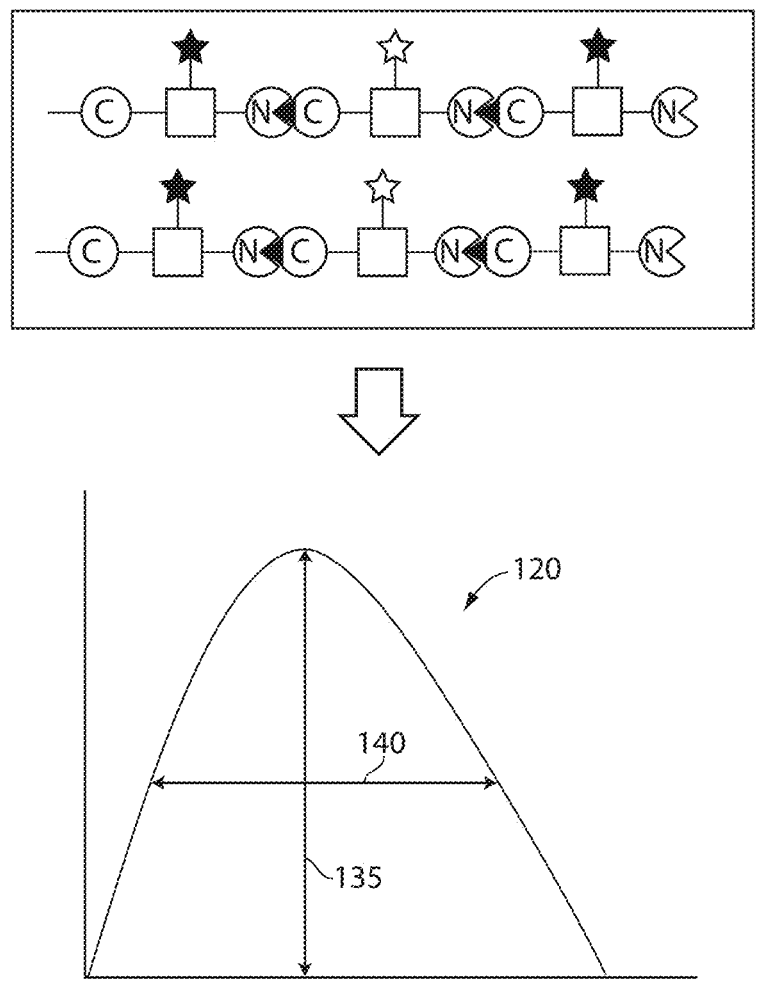
Figure 2B:
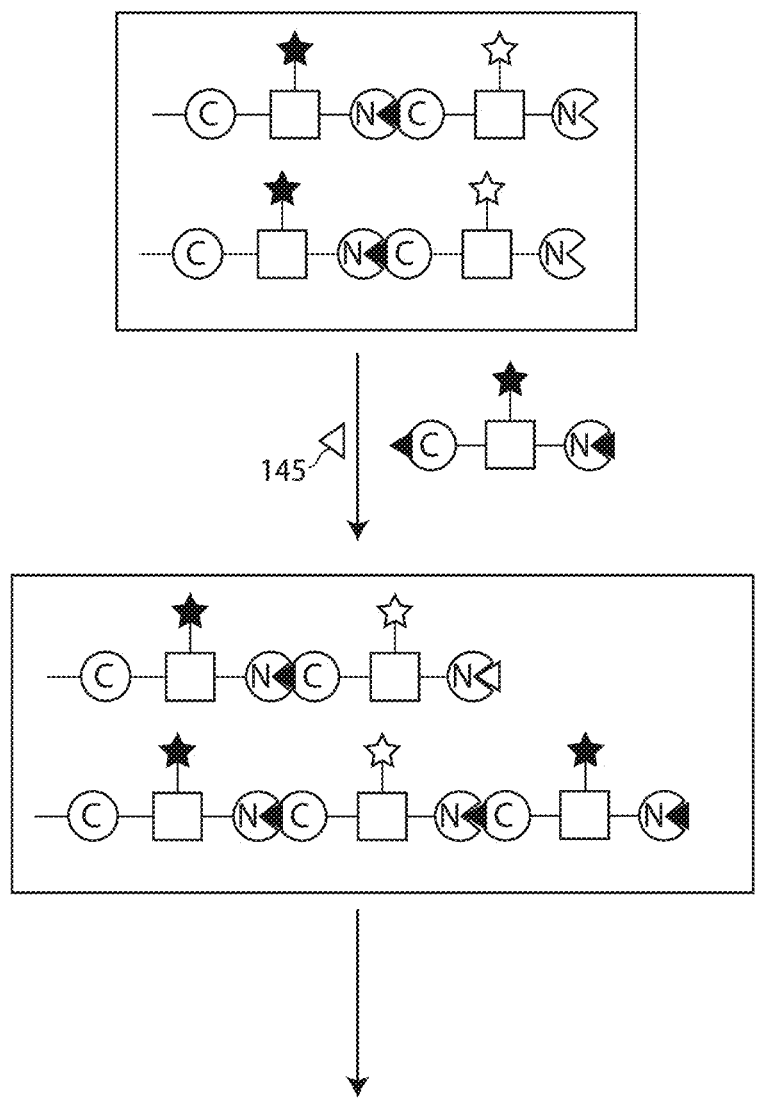
FIG. 2B is a schematic of peptide synthesis, according to certain embodiments.
Figure 2B:
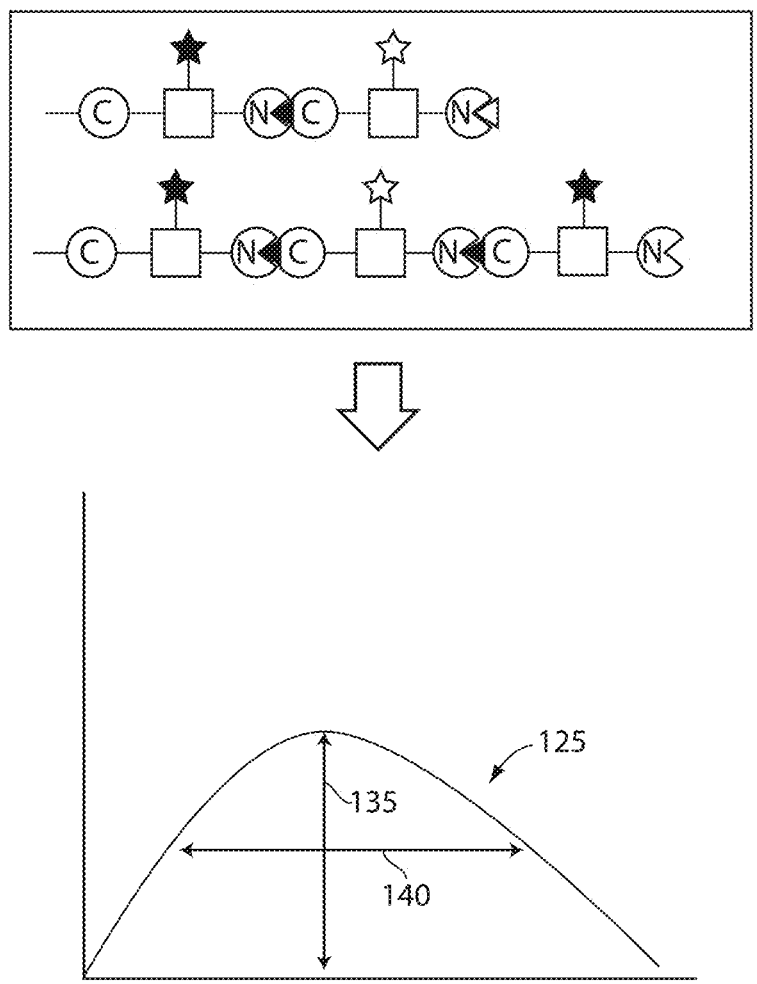
Figure 2C:
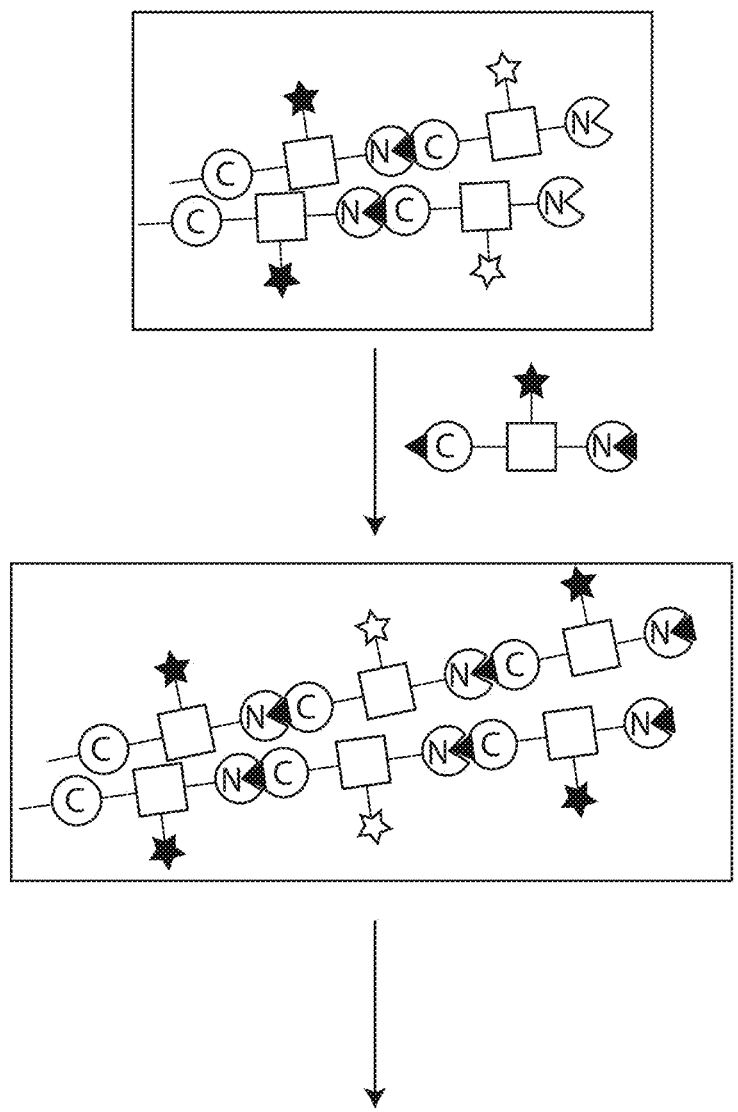
FIG. 2C is a schematic of peptide synthesis, according to certain embodiments.
Figure 2C:
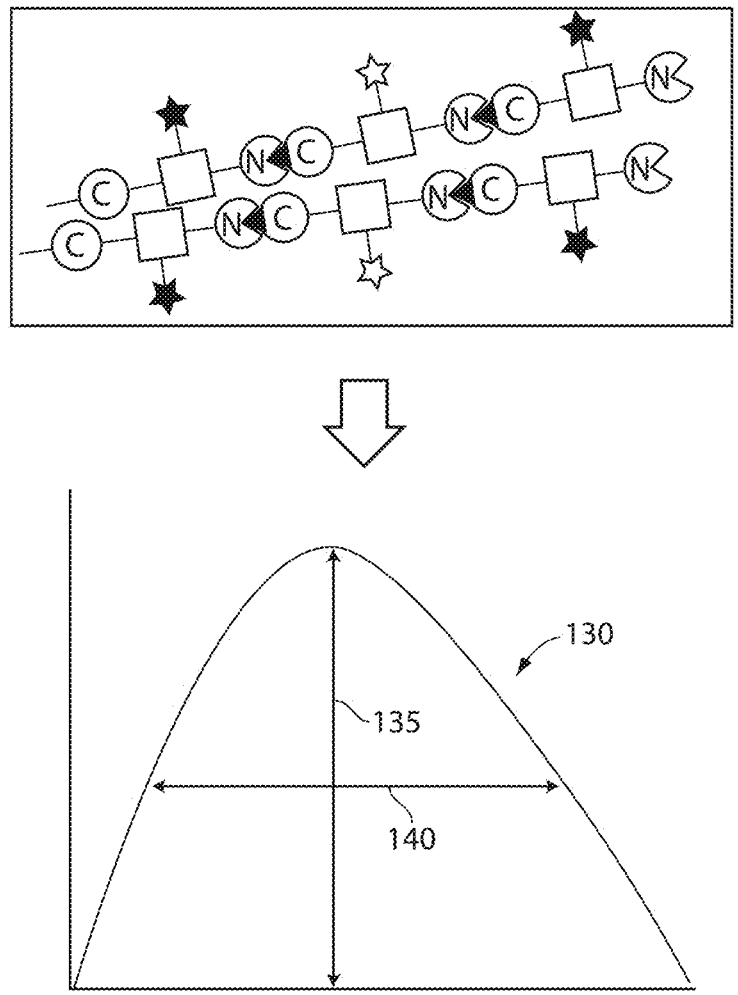

An exemplary schematic of peptide synthesis and signals that may be produced are shown in FIGS. 2A-2C. In some embodiments, as shown in FIGS. 2A-2C, peptides 80 may be immobilized on a solid support 85. The peptides may be bound to the solid support via their C termini, thereby immobilizing the peptides. In some embodiments, the process of adding amino acid residues to immobilized peptides comprises, in certain embodiments, exposing activated amino acids 95 to the immobilized peptides as indicated by arrow 90 of FIGS. 2A-2C. In some embodiments, as illustrated FIG. 2A, exposing the immobilized peptides to activated amino acids may result in at least a portion of the activated amino acids being bonded to the immobilized peptides to form newly-bonded amino acid residues. For example, the peptides may be exposed to activated amino acids 95 that react with the free N-termini 100 of the peptides. In certain embodiments, amino acids can be activated for reaction with the deprotected peptides by mixing an amino acid-containing stream with an activation agent stream and/or a base stream. In some instances, the amine group of the activated amino acid may be protected, such that addition of the amino acid results in an immobilized peptide with a protected N-terminus 105.

In general, peptides 80 may comprise protecting groups, for example, on the N-termini and/or the side chains 110 of the peptides. As used herein, the term "protecting group" is given its ordinary meaning in the art. Protecting groups include chemical moieties that are attached to or are configured to be attached to reactive groups (i.e., the protected groups) within a molecule (e.g., peptides) such that the protecting groups prevent or otherwise inhibit the protected groups from reacting. Protection may occur by attaching the protecting group to the molecule. In some embodiments, the side chains 110 of the amino acid residues in the peptide may comprise protecting groups. Deprotection may occur when the protecting group is removed from the molecule, for example, by a chemical transformation which removes the protecting group.

In some embodiments, prior to a subsequent coupling reaction, the protecting group of the newly formed protected N-terminus 105 must be removed to form a free N-terminus. In some such embodiments, the deprotection process comprises exposing a deprotection reagent to the immobilized peptides, as indicated by arrow 115, to remove at least a portion of the protecting groups from at least a portion of the immobilized peptides. The immobilized peptides may be exposed to the deprotection reagent by flowing a fluid stream comprising a deprotection reagent through a reactor. The deprotection reagent exposure step can be configured, in certain embodiments, such that side-chain protecting groups are preserved, while N-terminal protecting groups are removed. For instance, in certain embodiments, the protecting group used to protect the peptides comprises fluorenylmethyloxycarbonyl (Fmoc). In some such embodiments, a deprotection reagent comprising piperidine (e.g., a piperidine solution) may be exposed to the immobilized peptides such that the Fmoc protecting groups are removed from at least a portion of the immobilized peptides.

In some embodiments, the effluent from the reactor may be monitored during and/or after one or more reactions (e.g., deprotection reaction, coupling reaction) and/or processes (e.g., reagent removal step). In certain embodiments, as shown in FIGS. 2A-2C, the fluid stream exiting the reactor, during and/or after the deprotection step, may be detected using an electromagnetic radiation detector. The electromagnetic radiation detector may measure the electromagnetic absorbance and/or electromagnetic emission of the fluid stream and produce one or more corresponding signals. In some embodiments, the signal(s) may correspond to one or more components within the fluid stream and/or the interaction between two or more components in the fluid stream. In some such embodiments, the one or more components may be a byproduct or a side product of a reaction and/or process that occurred in the reactor. For instance, in embodiments in which Fmoc protecting groups are used to protect the N-termini of the peptides, a dibenzofulvene adduct may be formed as a byproduct of the deprotection reaction. At least a portion of the dibenzofulvene adduct may be removed from the reactor during and/or after the deprotection step and may be detected in the fluid stream exiting the reactor. In certain embodiments, the signal may comprise a collection of data points. In some such embodiments, the signal produced by the detector may include an intensity component, a duration component (e.g., duration of the signal), and/or a time component (e.g., peak width at half height, position in time, relative position in time). For instance, the electromagnetic radiation detector may produce a signal comprising an intensity and a time component (e.g., intensity versus time). In other instances, the signal may be a single value.

Non-limiting examples of a signal produced by the detector after a deprotection reaction is shown in FIGS. 2A-2C. The detector may produce the distribution of data shown in signals 120, 125, and 130 shown in FIG. 2A, FIG. 2B, and FIG. 2C, respectively. In some embodiments, one or more characteristics (e.g., peak area, peak height, peak width at half-height) of the signal may be used to identify a problem that has occurred in a prior reaction, identify a problem that has occurring in a current reaction, and/or determine the origin of the problem to aid in the selection of appropriate corrective action. For instance, FIG. 2A shows a coupling reaction and deprotection reaction for an amino acid addition cycle that are free of problems. Signal 120 may be produced from the detecting of the fluid stream downstream of the detector during and/or after the deprotection step. Signal 120 may correspond to an electromagnetic radiation intensity of a byproduct (e.g., dibenzofulvene adduct) over time. Signal 120 and/or one or more characteristics of the signal, such as the peak area, peak height 135, and/or peak width, e.g., at half-height 140 (e.g., peak height and peak width at half-height) may be compared to another signal and/or a reference signal to determine if a problem has occurred during a prior reaction (e.g., coupling reaction) in the reactor and/or is presently occurring (e.g., deprotection reaction).

FIG. 2B shows a coupling reaction and deprotection reaction for an amino acid addition cycle, which coupling is blocked in at least a portion of the peptides. As illustrated in FIG. 2B, unreacted activating agent 145 may react with at least a portion of the free N-termini and thereby prevent coupling with activated amino acids 95. Signal 125 may be produced from the detection of the fluid stream downstream of the detector during and/or after the deprotection step and may correspond to an electromagnetic radiation intensity of a byproduct (e.g., dibenzofulvene adduct) over time. Signal 125 and/or one or more characteristics of the signal, such as the peak area, peak height 135, and/or peak width at half-height 140 may be compared to another signal (e.g., signal 120) and/or a reference signal to determine if a problem has occurred during a prior reaction (e.g., coupling reaction) in the reactor and/or is presently occurring (e.g., deprotection reaction) and identify the source of the problem. For instance, the difference in peak height but not peak width at half height between reference signal and/or signal 120 may be indicative of a certain type of problem (e.g., truncation due to activation agent). Referring to FIG. 1, unit 70 and or a user may be used to analyze the signal(s) from the detector and identify the presence, absence, and/or source of a problem. In some such embodiments, unit 70 and or a user may determine appropriate corrective action to be implemented prior to and/or during a subsequent reaction (e.g., coupling reaction). In certain embodiments, unit 70 may automatically identify a problem, determine the source of the problem, and/or implement appropriate corrective action. In some cases, a user may be involved in identifying a problem, determining the source of the problem, and/or implementing appropriate corrective action. In some embodiments, corrective action may be implemented prior to completion of the synthesis of the peptide. For instance, information (e.g., time component, intensity component) derived from a signal produced by detecting an electromagnetic absorbance and/or an electromagnetic emission of the fluid stream during and/or immediately after a deprotection step following a coupling reaction between an amino acid and an amino acid residue immobilized on a solid support to form a peptide fragment may be used to modulate a parameter of the system prior to formation of the peptide comprising the peptide fragment.

FIG. 2C shows a coupling reaction and deprotection reaction for an amino acid addition cycle, in the peptides are aggregated. As illustrated in FIG. 2C, peptides 80 are aggregated during coupling, which negatively affects the reaction kinetics. Signal 130 may be produced from the detection of the fluid stream downstream of the detector during and/or after the deprotection step and may correspond to an electromagnetic radiation intensity of a byproduct (e.g., dibenzofulvene adduct) over time. Signal 130 and/or one or more characteristics of the signal, such as the peak area, peak height 135, and/or peak width at half-height 140 may be compared to another signal (e.g., signal 120 and/or signal 125) and/or a reference signal to determine if a problem has occurred during a prior reaction in the reactor and/or is presently occurring and identify the source of the problem. For instance, the difference in peak width at half height but not peak height between reference signal and/or signal 120 may be indicative of a certain type of problem (e.g., aggregation).

In some embodiments, a pattern of signals and one or more of their respective characteristics (e.g., peak area, peak height, peak width at half-height) may be used to identify a problem that has occurred in a prior reaction, identify a problem that has occurring in a current reaction, and/or determine the origin of the problem to aid in the selection of appropriate corrective action. A pattern of signals is produced using one or more detectors at detection zone 65. The pattern of signals may correspond to the measurement of electromagnetic radiation (e.g., UV absorbance) in the fluid stream during and/or after a plurality of reactions and/or processes in the reactor. For instance, in some embodiments, the pattern of signals may correspond to the measurement of electromagnetic radiation in the fluid stream during and/or after each deprotection step.

In certain embodiments, the pattern of signals comprises a first signal and a second signal. In some instances, the first and the second signals may comprise an intensity component, a duration component, and/or a time component. For instance, the signals may be similar to signals 120, 125, and 130. In some embodiments, analysis of a pattern of signals may provide information not present in a single signal, such as position of the signal in time relative to another signal position in time. In certain embodiments, the pattern of signals may indicate, in some embodiments, whether a particular reaction or process is taking place properly within the solid phase peptide synthesis system. For example, Table 1 shows exemplary information that may be obtained from a pattern of signals, the problem indicated by certain patterns, and possible corrective action. In Table 1, H refers to high and L refers to low.

TABLE 1

Exemplary analysis of a pattern of signals

| Peak 1 Area | Peak 2 Area | Peak 3 Area | Peak Widths | Interpretation/ Problem | Corrective Action | Additional Corrective Action(s) |
| --- | --- | --- | --- | --- | --- | --- |
| H | H | H | Constant | Efficient Coupling | Continue synthesis as planned | |
| H | L | H | Constant | Deletion of residue 2 | If change in area is >20%, end synthesis | Increase residence time for future Residue 2 couplings, use a more reactive activating agent |
| H | L | L | Constant | Truncation after residue 1 due to activating agent | If change in area is >30%, end synthesis | Change activating agent chemistry. Change stoichiometric ratios |
| H | H | H | Increasing | Aggregation of growing peptidyl chain | Increase temperature of reactor and fluid stream | Use amino acid analog at these sequence motifs |
| H | L | L | Increasing | Truncation after residue 1 due to aggregation | Increase temperature of reactor and fluid stream | |
| L | L | L | Constant | Improper resin loading or mechanical failure | Restart synthesis | |

Figure 3A:
FIG. 3A is a schematic of signals corresponding to certain peptide synthesis steps, according to one set of embodiments.
Figure 3B:
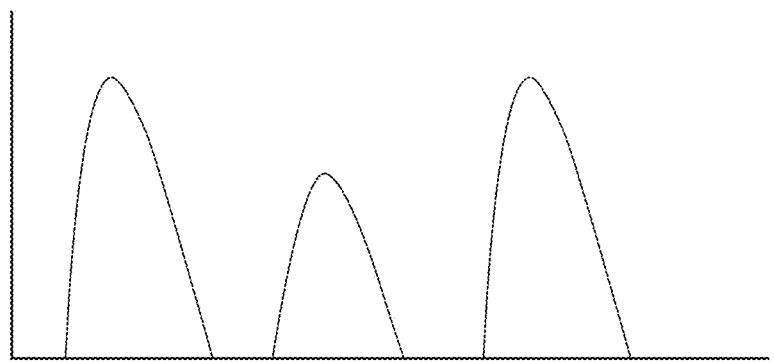
FIG. 3B is a schematic of signals corresponding to certain peptide synthesis steps, according to one set of embodiments.
Figure 3C:
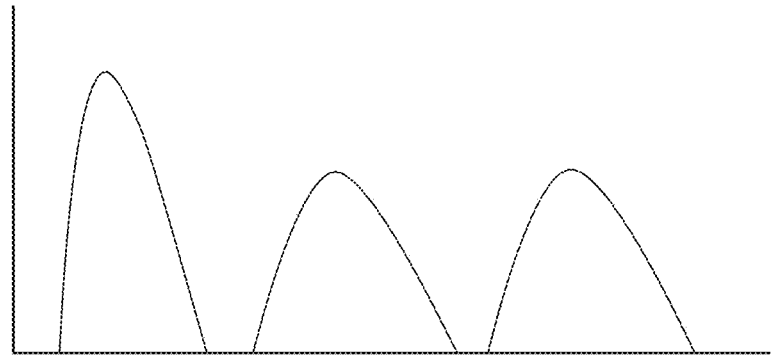
FIG. 3C is a schematic of signals corresponding to certain peptide synthesis steps, according to one set of embodiments.

In some embodiments, as illustrated in Table 1, analysis of a pattern of signals may allow additional information to be determined regarding the source of the problem and/or potential corrective action. For instance, comparison of two or more signal may allow certain reasons for a particular problem to be definitively determined. For instance, truncation due to aggregation may be definitively distinguished from truncation due to reaction with the activating agent or another contaminant. FIGS. 3A-3C shows exemplary schematics for patterns of signal for efficient coupling, truncation after residue 1 due to the activating agent, and truncation after residue 1 due to aggregation, respectively.

For instance, as illustrated in FIGS. 3A-3C, measuring the electromagnetic absorbance (e.g., UV absorbance, UV-vis absorbance) in a fluid stream to detect a byproduct of deprotection (e.g., dibenzofulvene adduct) during and/or after a series (e.g., two or more, three or more) of deprotection reaction may produce a series of curves. The peak area, peak height, and/or peak width at half-height may be used to determine whether efficient coupling has occurred, whether aggregation has occurred during coupling, whether deletion has occurred during coupling, whether truncation has occurred during coupling, whether improper resin has occurred during coupling, and/or whether mechanical failure has occurred during coupling. In certain embodiments, as illustrated in FIG. 3A, changes in peak area and/or peak width at half-height of less than about 5% (e.g., less than about 4%, less than about 2%, less than about 1%, less than about 0.5%, less than about 0.1%) between all of the curves may indicate that efficient coupling is occurring.

In some embodiments, a percentage change in the peak area may be used to estimate the amount of deletion and/or truncation at one or more steps (e.g., each). This may be done by integrating the area under the curve for a peak (e.g., from a UV absorbance measurement) and comparing the area to the areas of another signal(s). In some embodiments, as illustrated in FIG. 3B, a change in peak area of greater than or equal to about 5% (e.g., greater than or equal to about 10%, greater than or equal to about 15%, greater than or equal to about 20%) may indicate that a deletion and/or a truncation has occurred. Referring to Table 1, in some embodiment, a change in peak area from H to L or L to H may refer to a change in peak area by greater than or equal to about 5%. In certain embodiments, corrective action may be taken when the change is peak area is greater than or equal to about 5% but less than 30%. Corrective action may include modulating one or more parameters. For example, modulating reaction times, modulating flow rates, increasing temperatures, introducing fluid stream additives, increasing deprotection time, and/or changing activating agents may be done to improve subsequent coupling reactions. In some embodiments, if the change in area is greater than or equal to about 30%, the synthesis may be aborted due to low yield.

In some embodiments, as illustrated in FIG. 3C, the peak width at half height of the curve(s) may be used to distinguish between truncation due to activating agent and truncation due to aggregation as well as identify other problems due to aggregation. In some embodiments, as illustrated in FIG. 3C, a change in peak width at half height of greater than or equal to about 5% (e.g., greater than or equal to about 10%, greater than or equal to about 15%, greater than or equal to about 20%) may indicate, without being bound by theory, slower coupling kinetics and ultimately aggregation and/or diffusion problems. Referring to Table 1, in some embodiment, increasing peak width at half height may refer to a change in peak width by greater than or equal to about 5%. In some embodiments, Corrective action may include modulating one or more parameters. For example, a cosolvent and/or detergent additive(s) may be added to break up peptide aggregates, the temperature of the reactor and/or one or more fluid stream, and/or coupling reaction time may be increased as well to drive the reaction to completion.

When calculating the percentage difference between two values (unless specified otherwise herein), the percentage calculation is made using the value that is larger in magnitude as the basis. To illustrate, if a first value is $V_1$, and a second value is $V_2$ (which is larger than $V_1$), the percentage difference ($V_{\% \, Diff}$) between $V_1$ and $V_2$ would be calculated as:

$$V_{\% \, Diff} = \frac{V_2 - V_1}{V_2} \times 100\%$$

The first and second values would be said to be within X % of each other if $V_{\% \, Diff}$ is less than X %. The first and second values would be said to be at least X % different if $V_{\% \, Diff}$ is X % or more.

As described herein, a signal or pattern of signals may be used to determine and implement appropriate corrective action to address a problem. In some embodiments, corrective action may include modulating a parameter of the system prior to and/or during a reaction in the reactor based at least in part on information derived from a signal and/or comparison of two or more signals. For example, the parameter may be selected from the group consisting of a flow rate, a temperature, reaction time, a reagent type, a reagent concentration, reaction time, a ratio of reagents, addition of an additive, and combinations thereof. In embodiments in which corrective action cannot be taken, the synthesis may be stopped. For instance, as shown in Table 1, truncation due to the activating agent may be corrected by changing the activating agent chemistry and/or stoichiometric ratios during an activation step, for instance, using a carbodiimide instead of a guanidinium activator, or by increasing the ratio of amino acid to activating agent. As another example, the temperature of the reactor may be increased and detergents or cosolvents may be added to reagent fluid streams to better solubilize aggregated peptides. In one example, reagent concentration may be increased to prevent deletions. Flow rate and/or reaction time may be extended to prevent deletions for slow couplings. In general, the corrective actions may be implemented during the current synthesis and/or future syntheses. In embodiments in which corrective action cannot be taken, the synthesis may be stopped.

In some embodiments, modulating one or more parameter may include increasing the temperature of the reactor and/or one or more fluid streams. Modulating one or more parameter may include decreasing the temperature of the reactor and/or one or more fluid streams. In certain embodiments, modulating one or more parameter may include increasing the molar ratio two or more reagents and/or concentration of a reagent. Modulating one or more parameter may include decreasing the molar ratio two or more reagents and/or concentration of a reagent. In certain embodiments, modulating one or more parameter may include increasing flow rate of one or more fluid streams. Modulating one or more parameter may include decreasing flow rate of one or more fluid streams. In certain embodiments, modulating one or more parameter may include increasing the reaction time of one or more reactions (e.g., coupling reaction). Modulating one or more parameter may include decreasing the reaction time of one or more reactions (e.g., coupling reaction).

In some embodiments, implementation of the corrective action may be performed via a controller and/or a user. For instance, detection of reactions and/or processes in the solid phase peptide synthesis system can produce a signal or pattern of signals that can be transmitted to a controller. Based (at least in part) on the signal(s) received by the controller, this feedback can be used to modulate a parameter of the system by controlling, e.g., one or more of a pump, vacuum, valve, temperature regulator, and/or other components. In some cases, the feedback can determine problems that have occurred or are occurring in the solid phase peptide synthesis system, and the controller may send one or more signal(s) to one or more components to cause modulation of a parameter in all or portions of the system. Alternatively, when corrective action cannot be taken, the controller may send one or more signal(s) to one or more components to cause the system to shut down.

In certain embodiments, one or more measured signals is processed or manipulated (e.g., before or after transmission, and/or before being compared to a signal). It should be appreciated, therefore, that when a signal is transmitted (e.g., to a controller, user), compared (e.g., with a reference signal or another signal), or otherwise used in a feedback process, that the raw signal may be used or a processed/manipulated signal based (at least in part) on the raw signal may be used. For example, in some cases, one or more derivative signals of a measured signal can be calculated (e.g., using a differentiator, or any other suitable method) and used to provide feedback. In other cases, signals are normalized (e.g., subtracting a measured signal from a background signal). In one set of embodiments, a signal comprises a slope or average slope, e.g., an average slope of intensity as a function of time.

In some cases, the measured signal may be converted to a digital signal with the use of an analog to digital converter so that all further signal processing may be performed by a digital computer or digital signal processor. Although in one embodiment, all signal processing is performed digitally, the present invention is not so limited, as analog processing techniques may alternatively be used. For instance, a digital to analog converter may be used to produce an output signal. Signals may be processed in a time domain (one-dimensional signals), spatial domain (multidimensional signals), frequency domain, autocorrelation domain, or any other suitable domain. In some cases, signals are filtered, e.g., using a linear filter (a linear transformation of a measured signal), a non-linear filter, a causal filter, a non-causal filter, a time-invariant filter, a time-variant filter, or other suitable filters. It should be understood that the signals, patterns, and their use in feedback described herein are exemplary and that the invention is not limited in this respect.

Once a signal or pattern of signals has been determined, the signal(s) may be optionally transmitted to a controller. In some cases, the controller compares the signal or pattern of signals to a second set of signal(s). The second signal or pattern of signals may be, for example, signal(s) determined previously in the solid phase peptide system, or reference signal(s). In some cases, a reference signal or pattern of signals includes one or more threshold values or a range of threshold values. The controller may compare a first signal or pattern of signals with a second signal or pattern of signals (e.g., reference signals), and determine whether to modulate one or more parameter in the solid phase peptide synthesis system. That is, the measured signal or pattern of signals can be used by the controller to generate a drive signal and provide feedback control to the solid phase peptide synthesis system. This modulation may be performed, in certain embodiments, by the controller sending one or more drive signals to an appropriate component of the solid phase peptide synthesis system to actuate that or another component. Any suitable valve drive electronics circuit may be used to receive a drive signal and convert the drive signal to a voltage, current, or other signal capable of actuating the component. In certain embodiments, the controller can determine whether or not to modulate operation of one or more components of the solid phase peptide synthesis system. In some cases, the controller may determine whether or not to stop a synthesis being conducted in the solid phase peptide synthesis system.

In some embodiments, one or more feedback control methods such as proportional control, integral control, proportional-integral control, derivative control, proportional-derivative control, integral-derivative control, and proportional-integral-derivative control can be used by a controller to modulate a parameter. The feedback control may involve a feedback loop in some embodiments. In some cases involving one or more of the aforementioned feedback control methods, a drive signal (which may be used to modulate a parameter, e.g., by actuating a component of the microfluidic system) may be generated based at least in part on a signal and a feedback signal that is measured by a detector.

As described above, certain embodiments of the inventive systems include one or more controllers (e.g., computer implemented controllers) for operating various components/subsystems of the system, performing data/image analysis, etc. In some embodiments, the controller may be computer implemented. In general, any calculation methods, steps, simulations, algorithms, systems, and system elements described herein may be implemented and/or controlled using one or more computer implemented controller(s), such as the various embodiments of computer implemented systems described below. The methods, steps, controllers, and controller elements described herein are not limited in their implementation to any specific computer system described herein, as many other different machines may be used.

The computer implemented controller(s) can be part of or coupled in operative association with an image analysis system and/or other automated system components, and, in some embodiments, is configured and/or programmed to control and adjust operational parameters, as well as analyze and calculate values, for example analyte molecule or particle concentrations as described above. In some embodiments, the computer implemented controller(s) can send and receive reference signals to set and/or control operating parameters of system apparatus. In other embodiments, the computer implemented system(s) can be separate from and/or remotely located with respect to the other system components and may be configured to receive data from one or more remote assay systems of the invention via indirect and/or portable means, such as via portable electronic data storage devices, such as magnetic disks, or via communication over a computer network, such as the Internet or a local intranet.

The computer implemented controller(s) may include several known components and circuitry, including a processing unit (i.e., processor), a memory system, input and output devices and interfaces (e.g., an interconnection mechanism), as well as other components, such as transport circuitry (e.g., one or more busses), a video and audio data input/output (I/O) subsystem, special-purpose hardware, as well as other components and circuitry, as described below in more detail. Further, the computer system(s) may be a multi-processor computer system or may include multiple computers connected over a computer network.

The computer implemented controller(s) may include a processor, for example, a commercially available processor such as one of the series x86, Celeron and Pentium processors, available from Intel, similar devices from AMD and Cyrix, the 680X0 series microprocessors available from Motorola, and the PowerPC microprocessor from IBM. Many other processors are available, and the computer system is not limited to a particular processor.

A processor typically executes a program called an operating system, of which WindowsNT, Windows95 or 98, Windows XP, Windows Vista, Windows 7, UNIX, Linux, DOS, VMS, MacOS and OS8 are examples, which controls the execution of other computer programs and provides scheduling, debugging, input/output control, accounting, compilation, storage assignment, data management and memory management, communication control and related services. The processor and operating system together define a computer platform for which application programs in high-level programming languages are written. The computer implemented controller is not limited to a particular computer platform.

The computer implemented controller(s) may include a memory system, which typically includes a computer readable and writeable non-volatile recording medium, of which a magnetic disk, optical disk, a flash memory and tape are examples. Such a recording medium may be removable, for example, a floppy disk, read/write CD or memory stick, or may be permanent, for example, a hard drive.

Such a recording medium stores signals, typically in binary form (i.e., a form interpreted as a sequence of one and zeros). A disk (e.g., magnetic or optical) has a number of tracks, on which such signals may be stored, typically in binary form, i.e., a form interpreted as a sequence of ones and zeros. Such signals may define a software program, e.g., an application program, to be executed by the microprocessor, or information to be processed by the application program.

The memory system of the computer implemented controller(s) also may include an integrated circuit memory element, which typically is a volatile, random access memory such as a dynamic random access memory (DRAM) or static memory (SRAM). Typically, in operation, the processor causes programs and data to be read from the non-volatile recording medium into the integrated circuit memory element, which typically allows for faster access to the program instructions and data by the processor than does the non-volatile recording medium.

The processor generally manipulates the data within the integrated circuit memory element in accordance with the program instructions and then copies the manipulated data to the non-volatile recording medium after processing is completed. A variety of mechanisms are known for managing data movement between the non-volatile recording medium and the integrated circuit memory element, and the computer implemented controller(s) that implements the methods, steps, systems control and system elements control described above is not limited thereto. The computer implemented controller(s) is not limited to a particular memory system.

At least part of such a memory system described above may be used to store one or more data structures (e.g., look-up tables) or equations such as calibration curve equations. For example, at least part of the non-volatile recording medium may store at least part of a database that includes one or more of such data structures. Such a database may be any of a variety of types of databases, for example, a file system including one or more flat-file data structures where data is organized into data units separated by delimiters, a relational database where data is organized into data units stored in tables, an object-oriented database where data is organized into data units stored as objects, another type of database, or any combination thereof.

The computer implemented controller(s) may include a video and audio data I/O subsystem. An audio portion of the subsystem may include an analog-to-digital (A/D) converter, which receives analog audio information and converts it to digital information. The digital information may be compressed using known compression systems for storage on the hard disk to use at another time. A typical video portion of the I/O subsystem may include a video image compressor/decompressor of which many are known in the art. Such compressor/decompressors convert analog video information into compressed digital information, and vice-versa. The compressed digital information may be stored on hard disk for use at a later time.

The computer implemented controller(s) may include one or more output devices. Example output devices include a cathode ray tube (CRT) display, liquid crystal displays (LCD) and other video output devices, printers, communication devices such as a modem or network interface, storage devices such as disk or tape, and audio output devices such as a speaker.

The computer implemented controller(s) also may include one or more input devices. Example input devices include a keyboard, keypad, track ball, mouse, pen and tablet, communication devices such as described above, and data input devices such as audio and video capture devices and sensors. The computer implemented controller(s) is not limited to the particular input or output devices described herein.

It should be appreciated that one or more of any type of computer implemented controller may be used to implement various embodiments described herein. Aspects of the invention may be implemented in software, hardware or firmware, or any combination thereof. The computer implemented controller(s) may include specially programmed, special purpose hardware, for example, an application-specific integrated circuit (ASIC). Such special-purpose hardware may be configured to implement one or more of the methods, steps, simulations, algorithms, systems control, and system elements control described above as part of the computer implemented controller(s) described above or as an independent component.

The computer implemented controller(s) and components thereof may be programmable using any of a variety of one or more suitable computer programming languages. Such languages may include procedural programming languages, for example, LabView, C, Pascal, Fortran and BASIC, object-oriented languages, for example, C++, Java and Eiffel and other languages, such as a scripting language or even assembly language.

The methods, steps, simulations, algorithms, systems control, and system elements control may be implemented using any of a variety of suitable programming languages, including procedural programming languages, object-oriented programming languages, other languages and combinations thereof, which may be executed by such a computer system. Such methods, steps, simulations, algorithms, systems control, and system elements control can be implemented as separate modules of a computer program, or can be implemented individually as separate computer programs. Such modules and programs can be executed on separate computers.

Such methods, steps, simulations, algorithms, systems control, and system elements control, either individually or in combination, may be implemented as a computer program product tangibly embodied as computer-readable signals on a computer-readable medium, for example, a non-volatile recording medium, an integrated circuit memory element, or a combination thereof. For each such method, step, simulation, algorithm, system control, or system element control, such a computer program product may comprise computer-readable signals tangibly embodied on the computer-readable medium that define instructions, for example, as part of one or more programs, that, as a result of being executed by a computer, instruct the computer to perform the method, step, simulation, algorithm, system control, or system element control.

In general, any suitable electromagnetic radiation detector may be used to detect any form of electromagnetic radiation. For instance, the electromagnetic radiation detector may be a UV detector, as UV-vis detector, and/or infra-red radiation the detector. In some embodiments, the electromagnetic absorbance and/or the electromagnetic emission detected selected from a group consisting of infrared absorbance, infrared emission, ultraviolet absorbance and/or ultraviolet emission. In some embodiments, electromagnetic absorbance (e.g., UV, UV-vis, infrared) is detected.

As described herein, the methods and systems for feedback control may be used in solid phase peptide synthesis, which is described in more detail below. Exemplary amino acid addition cycles steps and peptide synthesis are now described in more detail. In some embodiments, the process of adding amino acid residues to immobilized peptides comprises exposing a deprotection reagent to the immobilized peptides to remove at least a portion of the protecting groups from at least a portion of the immobilized peptides as described above.

In some embodiments, the process of adding amino acid residues to immobilized peptides comprises removing at least a portion of the deprotection reagent. In some embodiments, at least a portion of any reaction byproducts (e.g., removed protecting groups) that may have formed during the deprotection step can be removed. In some instances, the deprotection reagent (and, in certain embodiments byproducts) may be removed by washing the peptides, solid support, and/or surrounding areas with a fluid (e.g., a liquid such as an aqueous or non-aqueous solvent, a supercritical fluid, and/or the like), for example stored in optional reservoir 125. In some instances, removing the deprotection reagent and reaction byproducts may improve the performance of subsequent steps (e.g., by preventing side reactions). In certain embodiments, the performance of subsequent steps is not dependent on the removal of at least a portion (e.g., substantially all) of the deprotection reagent and/or reaction byproducts. In some such cases, the removal step is optional. In embodiments in which the removal step is optional, the removal step may be reduced (e.g., reduction in time of the removal step, reduction in the amount of solvent used in the removal step) and/or eliminated. The reduction or elimination of one or more removal steps may reduce the overall cycle time. It should be understood that if an optional removal step is reduced or eliminated the subsequent step in the addition cycle may serve to remove at least a portion of the deprotection reagent and/or reaction byproducts, e.g., due to fluid flow in the system.

The process of adding amino acid residues to immobilized peptides comprises, in certain embodiments, exposing activated amino acids to the immobilized peptides such that at least a portion of the activated amino acids are bonded to the immobilized peptides to form newly-bonded amino acid residues. For example, the peptides may be exposed to activated amino acids that react with the deprotected N-termini of the peptides. In certain embodiments, amino acids can be activated for reaction with the deprotected peptides by mixing an amino acid-containing stream with an activation agent stream, as discussed in more detail below. In some instances, the amine group of the activated amino acid may be protected, such that addition of the amino acid results in an immobilized peptide with a protected N-terminus.

In some embodiments, the process of adding amino acid residues to immobilized peptides comprises removing at least a portion of the activated amino acids that do not bond to the immobilized peptides. In some embodiments, at least a portion of the reaction byproducts that may form during the activated amino acid exposure step may be removed. In some instances, the activated amino acids and byproducts may be removed by washing the peptides, solid support, and/or surrounding areas with a fluid (e.g., a liquid such as an aqueous or non-aqueous solvent, a supercritical fluid, and/or the like), for example stored in optional reservoir 125. In some instances, removing at least a portion of the activated amino acids and reaction byproducts may improve the performance of subsequent steps (e.g., by preventing side reactions). In certain embodiments, the performance of subsequent steps is not dependent on the removal of at least a portion (e.g., substantially all) of the activated amino acids and/or reaction byproducts. In some such cases, the removal step is optional. In embodiments in which the removal step is optional, the removal step may be reduced (e.g., reduction in time of the removal step, reduction in the amount of solvent used in the removal step) and/or eliminated. The reduction or elimination of one or more removal step may reduce the overall cycle time. It should be understood that if an optional removal step is reduced or eliminated the subsequent step in the addition cycle may serve to remove at least a portion of the activated amino acids and/or reaction byproducts, e.g., due to fluid flow in the system.

It should be understood that the above-referenced steps are exemplary and an amino acid addition cycle need not necessarily comprise all of the above-referenced steps. For example, an amino acid addition cycle may not include the deprotection reagent removal step and/or the activated amino acid removal step. Generally, an amino acid addition cycle includes any series of steps that results in the addition of an amino acid residue to a peptide.

In certain embodiments, during the amino acid addition steps, adding the amino acid can result in the peptide incorporating a single additional amino acid residue (i.e., a single amino acid residue can be added to the immobilized peptides such that a given peptide includes a single additional amino acid residue after the addition step). In some such embodiments, subsequent amino acid addition steps can be used to build peptides by adding amino acid residues individually until the desired peptide has been synthesized. In some embodiments, more than one amino acid residue (e.g., in the form of a peptide) may be added to a peptide immobilized on a solid support (i.e., a peptide comprising multiple amino acid residues can be added to a given immobilized peptide). Addition of peptides to immobilized peptides can be achieved through processes know to those of ordinary skill in the art (e.g., fragment condensation, chemical ligation). That is to say, during the amino acid addition step, adding an amino acid to an immobilized peptide can comprise adding a single amino acid residue to an immobilized peptide or adding a plurality of amino acid residues (e.g., as a peptide) to an immobilized peptide.

In certain embodiments, the first amino acid addition step (and/or subsequent amino acid addition steps) may add amino acids at a relatively high yield. For example, certain embodiments include exposing amino acids to the immobilized peptides such that an amino acid residue is added to at least about 99%, at least about 99.9%, at least about 99.99%, or substantially 100% of the immobilized peptides. In certain embodiments, a second (and, in some embodiments, a third, a fourth, a fifth, and/or a subsequent) amino acid addition cycle can be performed which may include exposing amino acids to the immobilized peptides such that an amino acid residue is added to at least about 99%, at least about 99.9%, at least about 99.99%, or substantially 100% of the immobilized peptides. In certain embodiments, the use of processes and systems of the present invention may allow the addition of more than one amino acid to the immobilized peptides to occur relatively quickly (including within any of the time ranges disclosed above or elsewhere herein), while maintaining a high reaction yield.

In certain embodiments, one or more amino acid addition steps can be performed while little or no double incorporation (i.e., adding multiple copies of a desired amino acid (e.g., single amino acid residues or peptides) during a single addition step). For example, in certain embodiments, multiple copies of the desired amino acid are bonded to fewer than about 1% (or fewer than about 0.1%, fewer than about 0.01%, fewer than about 0.001%, fewer than about 0.0001%, fewer than about 0.00001%, or substantially none) of the immobilized peptides during a first (and/or second, third, fourth, fifth, and/or subsequent) amino acid addition step.

In some embodiments, multiple amino acid addition cycles can be performed. Performing multiple amino acid addition cycles can result in more than one single-amino-acid residue (or more than one peptide, and/or at least one single-amino-acid residue and at least one peptide) being added to a peptide. In certain embodiments a process for adding more than one amino acid to immobilized peptides may comprise performing a first amino acid addition cycle to add a first amino acid and performing a second amino acid addition cycle to add a second amino acid. In certain embodiments, third, fourth, fifth, and subsequent amino acid addition cycles may be performed to produce an immobilized peptide of any desired length. In some embodiments, at least about 10 amino acid addition cycles, at least about 50 amino acid addition cycles, or at least about 100 amino acid addition cycles are performed, resulting in the addition of at least about 10 amino acid residues, at least about 50 amino acid residues, or at least about 100 amino acid residues to the immobilized peptides. In certain such embodiments, a relatively high percentage of the amino acid addition cycles (e.g., at least about 50%, at least about 75%, at least about 90%, at least about 95%, or at least about 99% of such amino acid addition cycles) can be performed at high yield (e.g., at least about 99%, at least about 99.9%, at least about 99.99%, or substantially 100%). In some such embodiments, a relatively high percentage of the amino acid addition cycles (e.g., at least about 50%, at least about 75%, at least about 90%, at least about 95%, or at least about 99% of such amino acid addition cycles) can be performed quickly, for example, within any of the time ranges specified above or elsewhere herein. In some such embodiments, a relatively high percentage of the amino acid addition cycles (e.g., at least about 50%, at least about 75%, at least about 90%, at least about 95%, or at least about 99% of such amino acid addition cycles) can be performed with limited or no double incorporation, for example, within any of the double incorporation ranges specified above or elsewhere herein.

In some embodiments, solid phase peptide synthesis may involve heating a stream prior to, but within a short period of time of, arrival at the reactor. Supplying the reactor with a heated stream may alter the kinetics of a process occurring in the reactor. For example, exposing immobilized peptides, solid supports, or other synthesis components to a heated stream may alter the reaction kinetics and/or diffusion kinetics of the amino acid addition process. For example, exposing the peptides to a heated stream comprising activated amino acids may increase the rate at which amino acids are added to the peptides. In some embodiments, heating the stream prior to, but within a short period of time of arrival at the reactor may substantially reduce or eliminate the need to supply auxiliary heat (i.e., heat that is not from one or more pre-heated streams) to the reactor. In some instances, most or substantially all of the heat supplied to the reactor originates from the pre-heated stream. For example, in some embodiments, the percentage of thermal energy that is used to heat the reactor that originates from the pre-heated stream(s) may be greater than or equal to about 50%, greater than or equal to about 60%, greater than or equal to about 70%, greater than or equal to about 80%, greater than or equal to about 90%, greater than or equal to about 95%, or greater than or equal to about 99%. In some such embodiments, heating the system in this way can reduce the time required to heat the reactor, immobilized peptides, solid support, activated amino acids, deprotection reagents, wash fluids, and/or other synthesis components to a desirable reaction temperature.

In some embodiments, a process for adding amino acid residues to peptides may comprise heating a stream comprising activated amino acids such that the temperature of the activated amino acids is increased by at least about 1° C. (or at least about 2° C., at least about 5° C., at least about 10° C., at least about 25° C., at least about 50° C., and/or less than or equal to about 100° C., and/or less than or equal to about 75° C.) prior to the heated amino acids being exposed to the immobilized peptides. In certain embodiments, a stream comprising any other component (e.g., a washing agent, a deprotection agent, or any other components) may be heated such that the temperature of the stream contents is increased by at least about 1° C. (or at least about 2° C., at least about 5° C., at least about 10° C., at least about 25° C., at least about 50° C., and/or less than or equal to about 100° C., and/or less than or equal to about 75° C.) prior to the stream contents being exposed to the immobilized peptides. In some instances, the heating step (e.g., the heating of the activated amino acids and/or the heating of any other component within a stream transported to the immobilized peptides) may be performed within about 30 seconds (or within about 15 seconds, within about 10 seconds, within about 5 seconds, within about 3 seconds, within about 2 seconds, within about 1 second, within about 0.1 seconds, or within about 0.01 seconds) of exposing the stream contents (e.g., the heated activated amino acids) to the immobilized peptides. In some such embodiments, such heating may be achieved by heating a location upstream of the immobilized peptides. In some such embodiments, the heating of the amino acids begins at least about 0.1 seconds, at least about 1 second, at least about 5 seconds, or at least about 10 seconds prior to exposure of the amino acids to the immobilized peptides. In certain embodiments, the amino acids are heated by at least about 1° C. (or at least about 2° C., at least about 5° C., at least about 10° C., at least about 25° C., at least about 50° C., and/or less than or equal to about 100° C., and/or less than or equal to about 75° C.) at least about 0.1 seconds, at least about 1 second, at least about 5 seconds, or at least about 10 seconds prior to the amino acids being exposed to the immobilized peptides.

In some embodiments, both the heating of the amino acids and the merging of the amino acids with the base and/or activating agent can be performed before and within a relatively short time of the amino acids contacting the immobilized peptides. Heating the amino acids may be performed before, during, and/or after merging the streams.

In general, any protecting group known to those of ordinary skill in the art can be used. Non-limiting examples of protecting groups (e.g., n-terminal protecting groups) include fluorenylmethyloxycarbonyl, tert-butyloxycarbonyl, allyloxycarbonyl (alloc), carboxybenzyl, and photolabile protecting groups. In certain embodiments, immobilized peptides comprise fluorenylmethyloxycarbonyl protecting groups. In some embodiments, immobilized peptides comprise tert-butyloxycarbonyl protecting groups.

As described elsewhere, an activating agent may be used to activate or complete the activation of amino acids prior to exposing the amino acids to immobilized peptides. Any suitable activating agent may be used. The activating agent comprises, in some embodiments, a carbodiimide, such as N,N'-dicyclohexylcarbodiimide (DCC), 1-ethyl-3-(3-dimethylaminopropyl)carbodiimide (EDC), and the like. In certain embodiments, the activating agent comprises a uronium activating agent, such as O-(Benzotriazol-1-yl)-N,N,N',N'-tetramethyluronium hexafluorophosphate (HBTU); 2-(7-Aza-1H-benzotriazole-1-yl)-1,1,3,3-tetramethyluronium hexafluorophosphate (HATU); 1-[(1-(Cyano-2-ethoxy-2- oxoethylideneaminooxy) dimethylaminomorpholino)]uronium hexafluorophosphate (COMU); and the like.

As described elsewhere, peptides may be immobilized on a solid support. In general, any solid support may be used with any of the addition cycles described herein. Non-limiting examples of solid support materials include polystyrene (e.g., in resin form such as microporous polystyrene resin, mesoporous polystyrene resin, macroporous polystyrene resin), glass, polysaccharides (e.g., cellulose, agarose), polyacrylamide resins, polyethylene glycol, or copolymer resins (e.g., comprising polyethylene glycol, polystyrene, etc.).

The solid support may have any suitable form factor. For example, the solid support can be in the form of beads, particles, fibers, or in any other suitable form factor.

In some embodiments, the solid support may be porous. For example, in some embodiments macroporous materials (e.g., macroporous polystyrene resins), mesoporous materials, and/or microporous materials (e.g., microporous polystyrene resin) may be employed as a solid support. The terms "macroporous," "mesoporous," and "microporous," when used in relation to solid supports for peptide synthesis, are known to those of ordinary skill in the art and are used herein in consistent fashion with their description in the International Union of Pure and Applied Chemistry (IUPAC) Compendium of Chemical Terminology, Version 2.3.2, Aug. 19, 2012 (informally known as the "Gold Book"). Generally, microporous materials include those having pores with cross-sectional diameters of less than about 2 nanometers. Mesoporous materials include those having pores with cross-sectional diameters of from about 2 nanometers to about 50 nanometers. Macroporous materials include those having pores with cross-sectional diameters of greater than about 50 nanometers and as large as 1 micrometer.

As used herein, the term "peptide" has its ordinary meaning in the art and may refer to amides derived from two or more amino carboxylic acid molecules (the same or different) by formation of a covalent bond from the carbonyl carbon of one to the nitrogen atom of another with formal loss of water. An "amino acid residue" also has its ordinary meaning in the art and refers to the composition of an amino acid (either as a single amino acid or as part of a peptide) after it has combined with a peptide, another amino acid, or an amino acid residue. Generally, when an amino acid combines with another amino acid or amino acid residue, water is removed, and what remains of the amino acid is called an amino acid residue. The term "amino acid" also has its ordinary meaning in the art and may include proteogenic and non-proteogenic amino acids.

As used herein, the term "protecting group" is given its ordinary meaning in the art. Protecting groups include chemical moieties that are attached to or are configured to be attached to reactive groups (i.e., the protected groups) within a molecule (e.g., peptides) such that the protecting groups prevent or otherwise inhibit the protected groups from reacting. Protection may occur by attaching the protecting group to the molecule. Deprotection may occur when the protecting group is removed from the molecule, for example, by a chemical transformation which removes the protecting group.

The following examples are intended to illustrate certain embodiments of the present invention, but do not exemplify the full scope of the invention.

Example 1

This example describes the use of in-line UV absorbance spectroscopy to perform real-time control of a flow peptide synthesis. This was accomplished by quantitative analysis of the dibenzofulvene adduct released from the resin-bound polypeptide during the Fmoc removal step. Real-time control involved taking actions to enhance synthesis, such as decreasing flow rates, increasing temperature, increasing coupling times, increasing deprotection times, or using an alternate coupling reagent. If the synthesis was deemed to be irreparable, the synthesis could be aborted to save reagents. This method used UV absorbance to quantitatively correlate synthesis conditions to products observed with LC-MS analysis.

Figure 4:
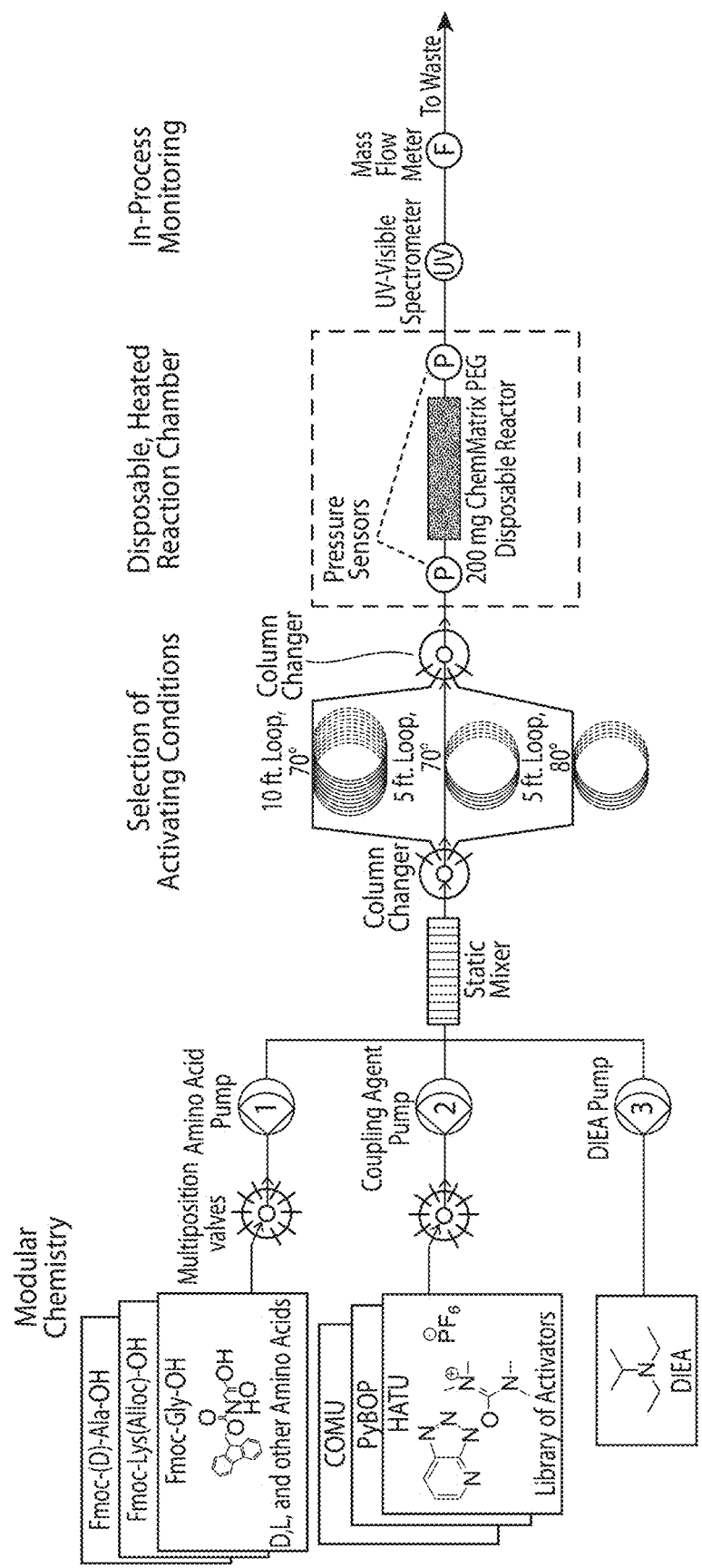
FIG. 4 is a schematic of the automated flow peptide synthesizer having an electromagnetic radiation detector, according to certain embodiments.
Figure 5:
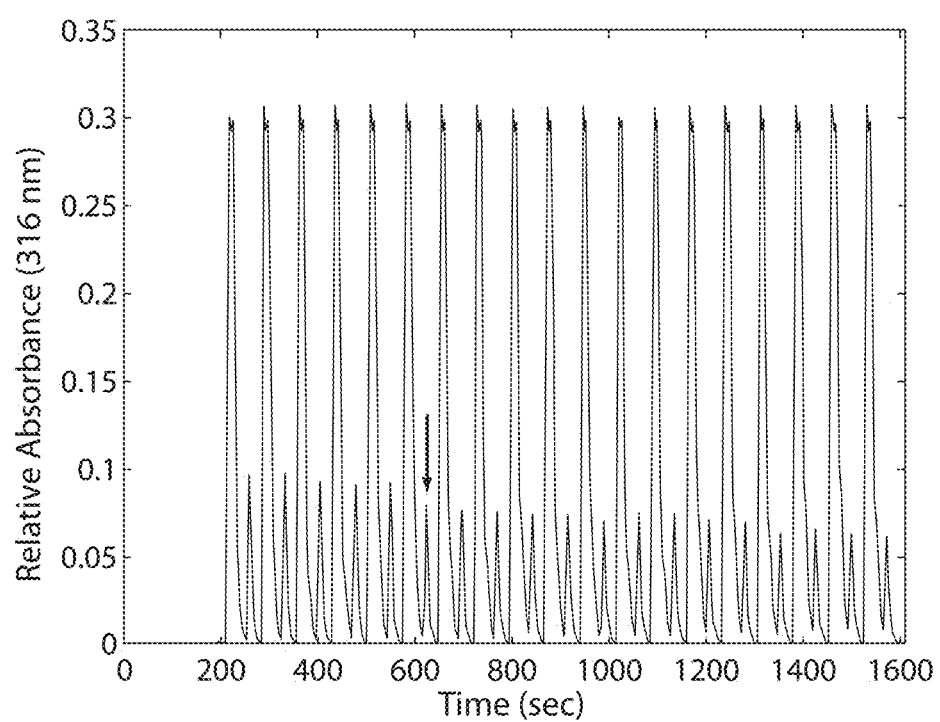
FIG. 5 is a graph of relative abundance versus time determined using a detector during the synthesis of a 19 amino acid peptide, according to certain embodiments.
Figure 7A:
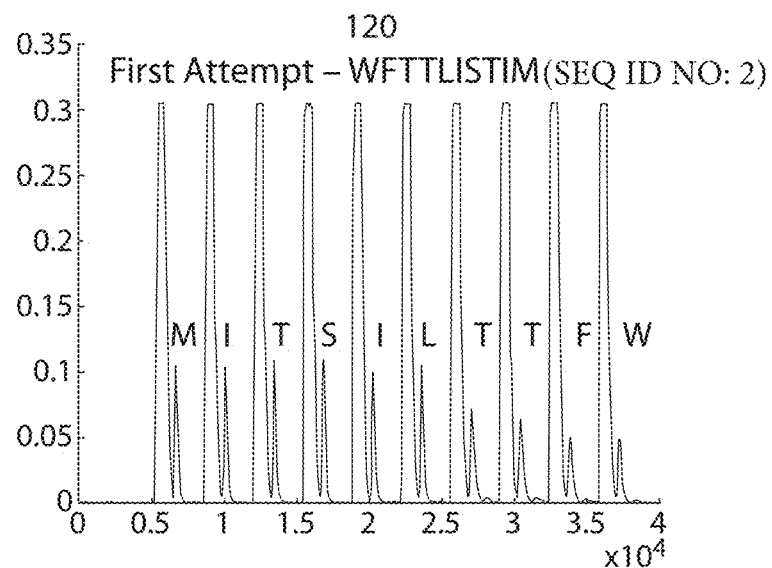
FIG. 7A is a UV trace under certain reaction conditions, according to one set of embodiments.
Figure 7B:
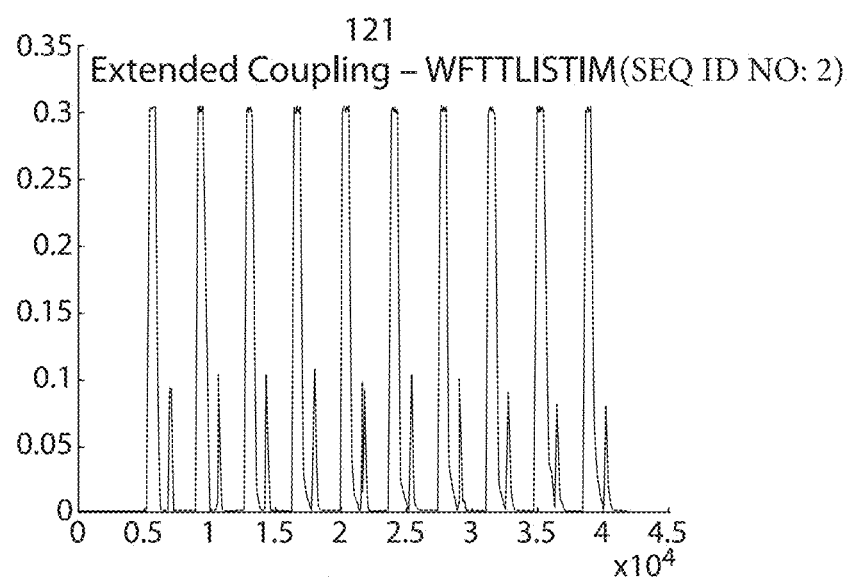
FIG. 7B is a UV trace under certain reaction conditions, according to one set of embodiments.
Figure 7C:
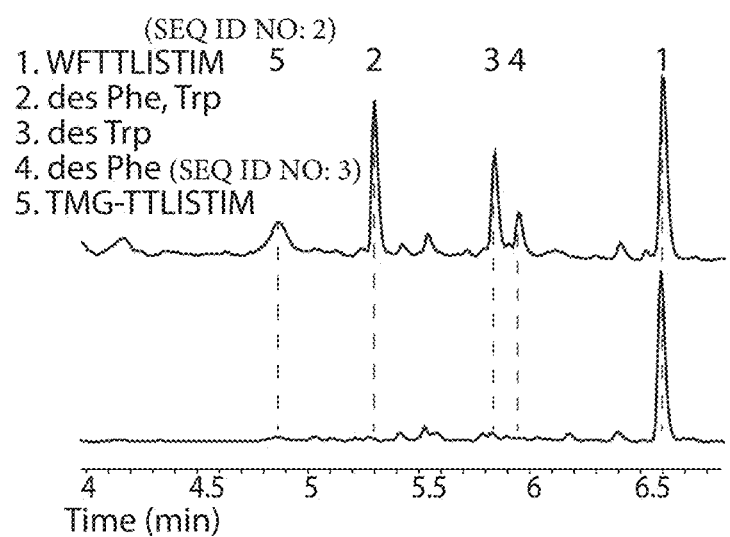
FIG. 7C is liquid chromatograms, according to one set of embodiments.
Figure 7D:
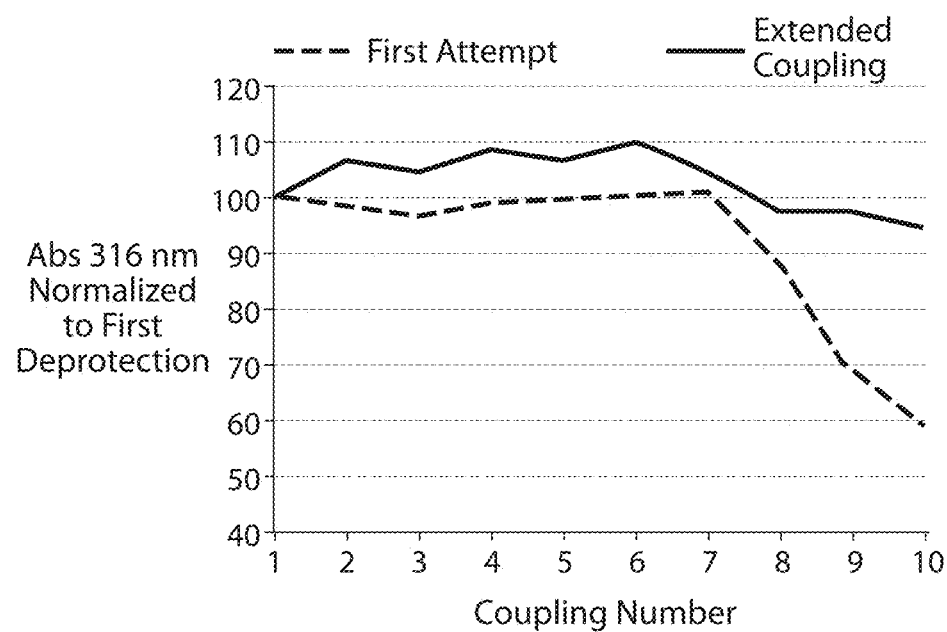
FIG. 7D is a graph of absorbance versus coupling number according to one set of embodiments.

FIG. 4 shows a schematic of the automated flow peptide synthesizer with an inline UV-vis spectrometer. During the Fmoc removal step of solid phase peptide synthesis, treatment of the Fmoc protected polypeptide chain liberates carbon dioxide and dibenzofulvene from the N-terminus of the growing peptide chain. Dibenzofulvene reacts quickly with the deprotection agent in solution and this adduct absorbs in the UV range. The automated flow synthesizer was uniquely able to monitor the UV absorbance of the dibenzofulvene adduct present in the reactor effluent stream in real time using a standard UV-visible spectrometer. The UV-visible spectrometer gave quantitative information about the efficiency of each coupling step and/or each deprotection step. FIG. 5 shows a graph of relative abundance versus time determined using a detector during the synthesis of a 19 amino acid peptide. The tall, oversaturated peaks occurred during infusion of amino acid and activator into the reactor. During treatment with piperidine, the smaller peaks were generated by liberation of dibenzofulvene. As indicated by the red arrow, a sharp decrease in Fmoc removal that did not recover was indicative of chain termination.

The flow-based approach of the quantitation of the dibenzofulvene adduct was advantageous over the traditional measurement of Fmoc removal in batch. To perform this type of monitoring in batch, the resin has to be scrupulously washed and all washes must be saved. Differences in the final volume of solution must also be corrected for. In practice, these limitations make the measurement non-quantitative. In this example, by contrast, the process of UV monitoring was rigorously controlled, and the temporally resolved signal could be integrated in a chromatogram style fashion to give a measure of coupling efficiency.

It was observed that a decrease in dibenzofulvene absorbance was correlated to chain truncation events and amino acid non-incorporations. For chain truncations, the absorbance never recovered to previous levels, and for amino acid non-incorporations there was often a recovery in the amount of Fmoc removed during the subsequent deprotection. In practice, these data were used for rapid optimization, before cleavage and chromatographic analysis of the polypeptide, of chain assembly conditions increased process throughput.

FIG. 6 shows Fmoc removal peaks for two residues, a threonine and a cysteine, of EETI-II, a cysteine knot miniprotein. It is noted that the synthesis was performed from the C- to N-terminus of the peptide, so the cysteine was coupled first and its peak appeared on the left. When HBTU was first used during the synthesis, there was a 30% decrease in the integrated peak area for the Fmoc removal of threonine. This piece of data suggested that the coupling was not completely efficient, prompting the switch to HATU, a more reactive, but more expensive, coupling agent, for just this coupling. Using HATU, there was only an 8% decrease in signal. Analysis of the crude peptides with LC-MS revealed that the major side product of the synthesis with HBTU was a threonine deletion at 40% of the main peak intensity. This threonine deletion was not observed when using HATU. Most crucially, this complete optimization was performed in less than an hour, which would not have been possible with traditional methods. FIG. 6 shows the comparison of dibenzofulvene signals from the synthesis of EETI-II when using (A) HATU or (B) HBTU. The large decrease in signal for Fmoc removal after threonine coupling when using HBTU was manifested in the crude peptide chromatogram as a large threonine deletion.

FIG. 7 shows another example of this type of optimization. A first attempt at the synthesis of the "JR 10-mer" (i.e., WFTTLISTIM (SEQ ID NO: 2)) polypeptide, a classic difficult sequence, yielded decreasing areas of the UV deprotection signals toward the end of the peptide synthesis, as seen in Panel A of FIG. 7. This corresponded with both a truncation of the polypeptide chain as observed by LC-MS (Panel C, product 5) as well as major deletions of phenylalanine and tryptophan (Panel C, products 2, 3, and 4). Based on the UV data alone, it was determined that the coupling time should be increased for the final residues in the sequence. This corrective action dramatically increased the quality of the desired polypeptide as analyzed by LC-MS, and as seen in Panel B, a recovery of the UV signals was observed for deprotection. This entire optimization was performed in 20 minutes using this data, as opposed to hours if only LC-MS data were used.

EETI-II, sequence shown in FIG. 6, was synthesized using standard synthesis parameters with HBTU at 70° C. and 40 mL/min total flow rate. During the coupling of the underlined threonine, a peak area decrease of 30% was observed for the deprotection signal. This peak area decrease corresponded to a threonine residue deletion in the final LC-MS analysis of the peptide. During the next coupling of the threonine residue, HATU, a more reactive activating agent was used for the coupling. Only an 8% change in peak area was observed during the deprotection of the threonine, and the deletion was not observed in the LC-MS trace of the final product.

The 10-mer (i.e., WFTTLISTIM (SEQ ID NO: 2)) polypeptide was initially synthesized at 90° C., 80 mL/min flow rate, with 5 mL coupling solution delivered during the amino acid addition step. A drastic reduction in the UV trace as shown in Panel A of FIG. 7 was indicative of amino acid deletions in the LC-MS chromatogram (Panel C, Top). Extending the coupling times for these residues recovered the UV trace as shown in Panel B of FIG. 7 and eliminated these deletions as shown in Panel C of FIG. 8, bottom). Panel D of FIG. 7 shows integrations for the deprotection peaks as a line graph.

The detection of truncation byproducts using UV signal is shown in FIG. 7, panel A. FIG. 7, panel A shows a UV trace obtained during the synthesis of JR 10-mer (WFTTLISTIM (SEQ ID NO: 2)) synthesized at 90° C. and at 80 mL/min total flow rate. The deprotection peaks have been labeled with their corresponding residue. Proceeding from the L to the T coupling, a sharp decrease in peak area was observed and the area did not recover in the subsequent signals. This corresponded to the observance of byproduct 5, a truncation, in the product mixture. FIG. 7, panel B, shows the results of synthesis optimization performed using UV data.

Because a sharp decrease in peak area and height was observed proceeding from the L to the T coupling in experiment A, two corrective actions were performed. First, a second deprotection step was performed after the first deprotection step to assess whether or not the deprotection was quantitative. The absence of a signal during the second deprotection treatment indicated that there was a problem with coupling and not the deprotection. Second, the amount of time exposing the immobilized peptides to activated amino acid was doubled in experiment B. The resultant UV traces demonstrated that the coupling efficiency was greatly increased. This corresponded to a much cleaner crude peptide with most of the deletion products absent (Panel C). This same optimization could be performed upon observation of the first peak height decrease during the threonine coupling. The truncation would still be present; however, the deletion products of phenylalanine and tryptophan could be avoided in this case.

Example 2

This example describes the use of in-line UV absorbance spectroscopy to perform real-time control of a flow peptide synthesis.

Amide bond forming reactions are prevalent in the syntheses of therapeutic small molecules, peptides, and proteins. Of 128 recently surveyed small molecule drug candidates, 65% required formation of an amide. In addition to small molecules, peptides, including GLP-1 agonists for diabetes treatment, require forming up to 40 amide bonds. Personalized peptide vaccines, a frontier in cancer treatment, require custom synthesis for each patient. However, research, development, and production of these peptides is limited by synthesis speed, typically minutes to hours for each amino acid addition and deprotection cycle. In this example, we report a fully automated, flow chemistry approach to solid phase polypeptide synthesis with amide bond formation in seven seconds and complete cycle times in forty seconds is described. Crude peptide qualities and isolated yields were comparable to standard batch solid phase peptide synthesis. At full capacity, this machine could synthesize 25,000 30-mer individual peptides per year weighing a combined 25 kilograms.

Peptides and proteins are important in the search for new therapeutics. Underpinning peptide and protein research is the need to design new functional variants and to quickly iterate on these designs. Biological expression of peptides can be fast and scalable—the ribosome synthesizes peptides at a rate of 15 peptide bonds per second—but becomes difficult outside of the twenty, naturally-occurring amino acids. On the other hand, despite the expanded number of monomers, chemical peptide synthesis remains relatively slow. In this example, Automated Flow Peptide Synthesis (AFPS), a method with the flexibility of chemical synthesis that approaches the speed of the ribosome is described. AFPS reduces the amide bond forming step to seven seconds and the entire cycle for each amino acid addition to 40 seconds while maintaining a high level of control over the chemistry. UV monitoring and disposable reactors allow for yield quantitation and fast, automated switchover.

Figure 8A:
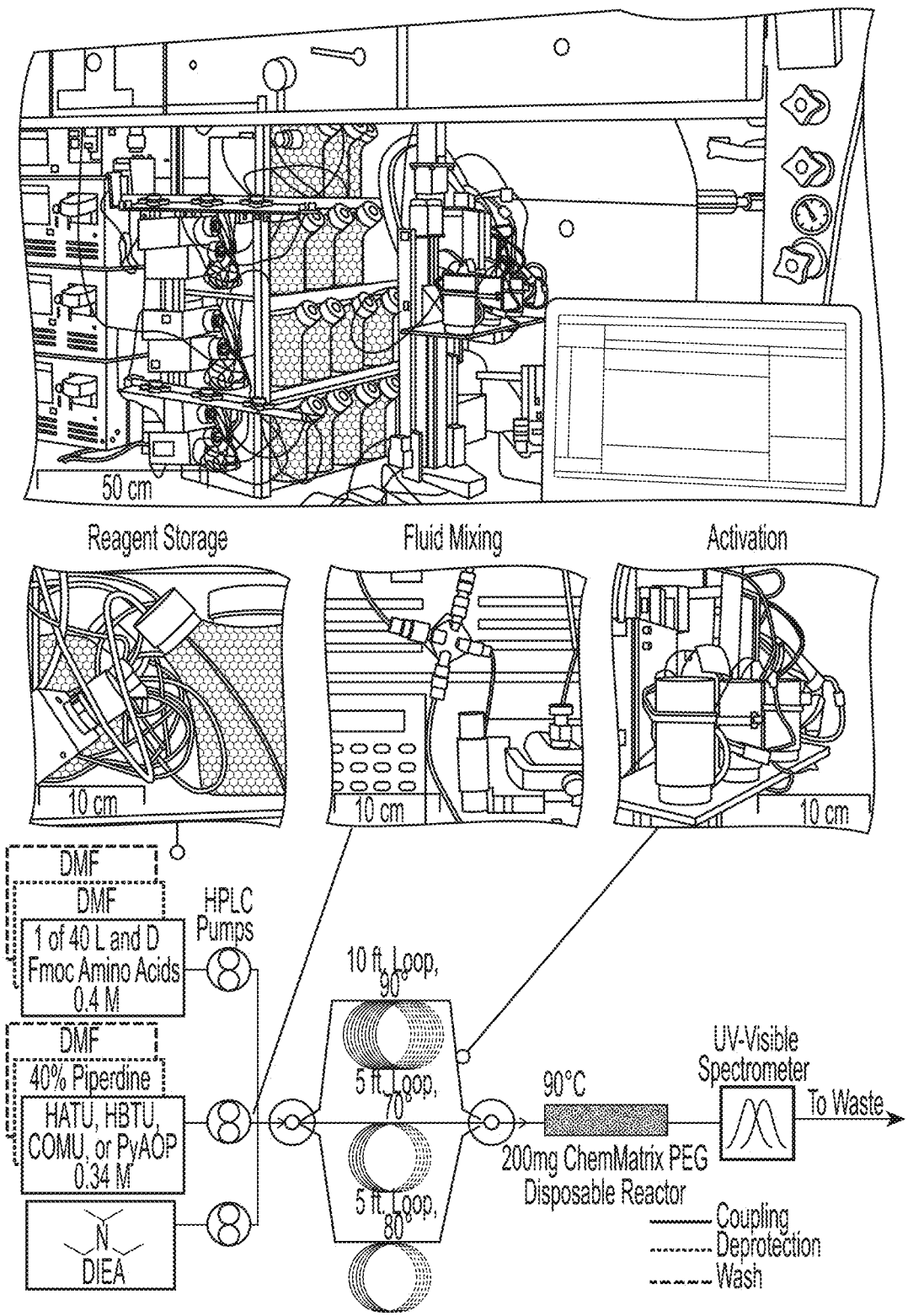
FIG. 8A is a photograph of the automated flow solid phase synthesizer, according to one set of embodiments.
Figure 8B:
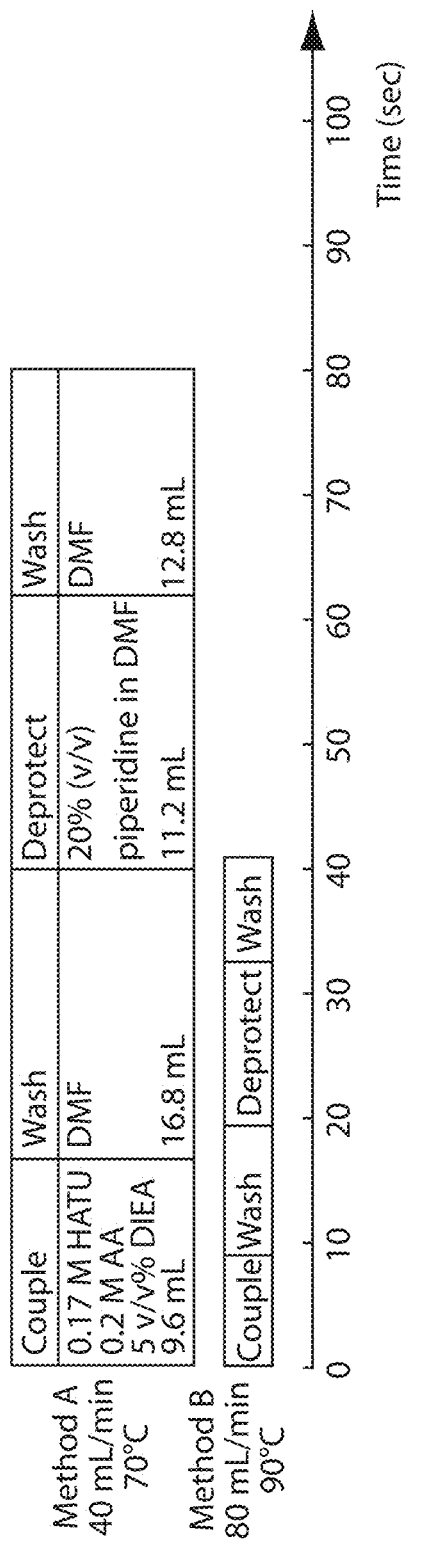
FIG. 8B is a cycle diagram of a peptide synthesis, according to certain embodiments.

The Automated Flow Peptide Synthesizer consists of five modules, depicted in FIGS. 8A-8B. During a coupling reaction, the machine draws reagents from the storage module, and then mixes the desired amino acid with an amine base (diisopropylethylamine, DIEA), and an activating agent (e.g. HATU or PyAOP) in the mixing module. This mixture flows through the activation module, an electrically heated plug flow reactor, where it quickly heats to 90° C. Within two seconds of activation, the activated amino acid flows through the coupling module, a packed bed of peptide synthesis resin, where amide bond formation is complete within seven seconds. The resin is contained in a 6-mL disposable syringe cartridge for easy removal. The AFPS monitors Fmoc removal for each cycle by recording the absorbance of the reactor effluent as a function of time. The Fmoc removal absorbance chromatogram allows the deprotection efficiency, the coupling yield, and the rate of material flux through the peptidyl resin to be inferred, which allowed for the identification of on-resin peptide aggregation.

Figure 8C:
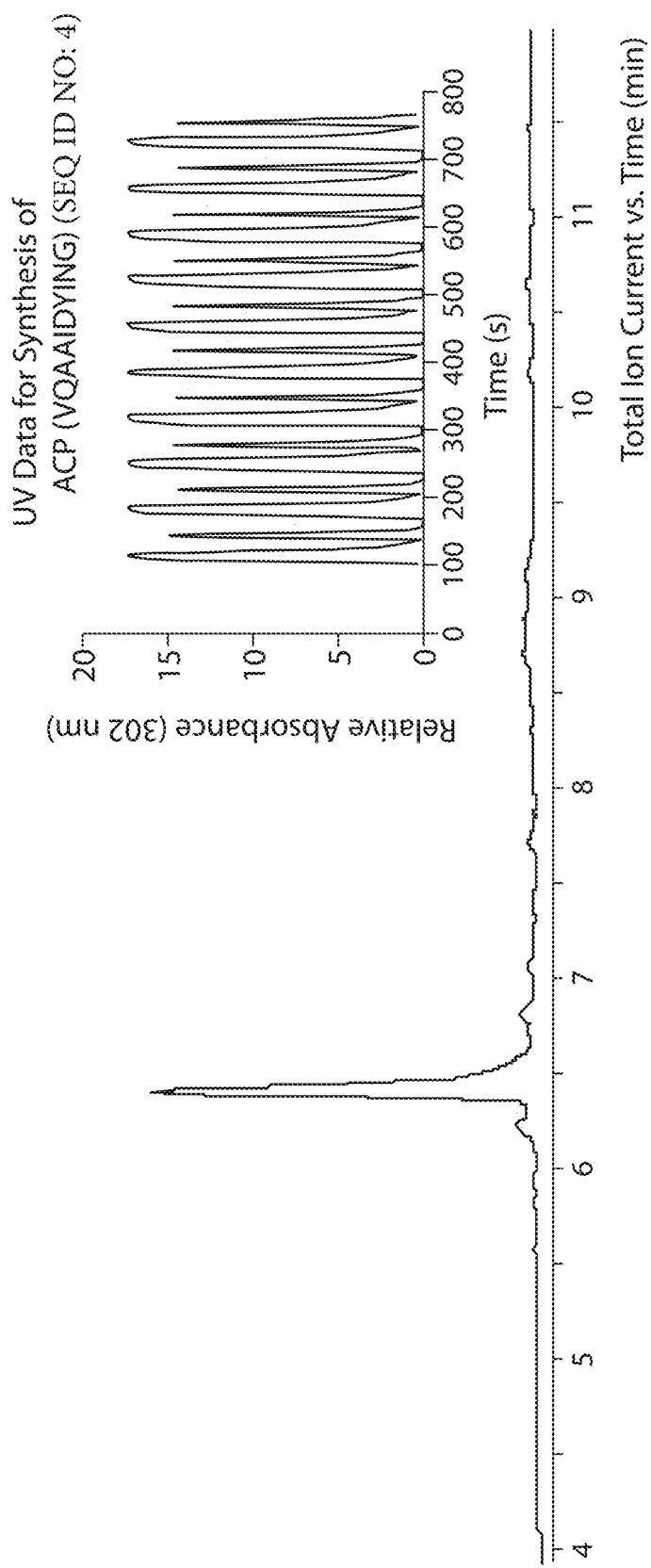
FIG. 8C is a LC-MS chromatogram for the crude product of acyl carrier protein (65-74) synthesis, according to one set of embodiments.
Figure 8D:
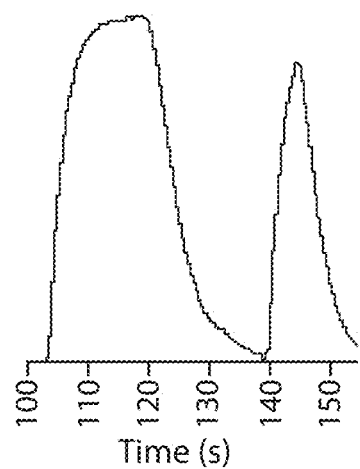
FIG. 8D is a UV absorbance spectrum for one coupling and deprotection cycle, according to one set of embodiments.
Figure 9A:
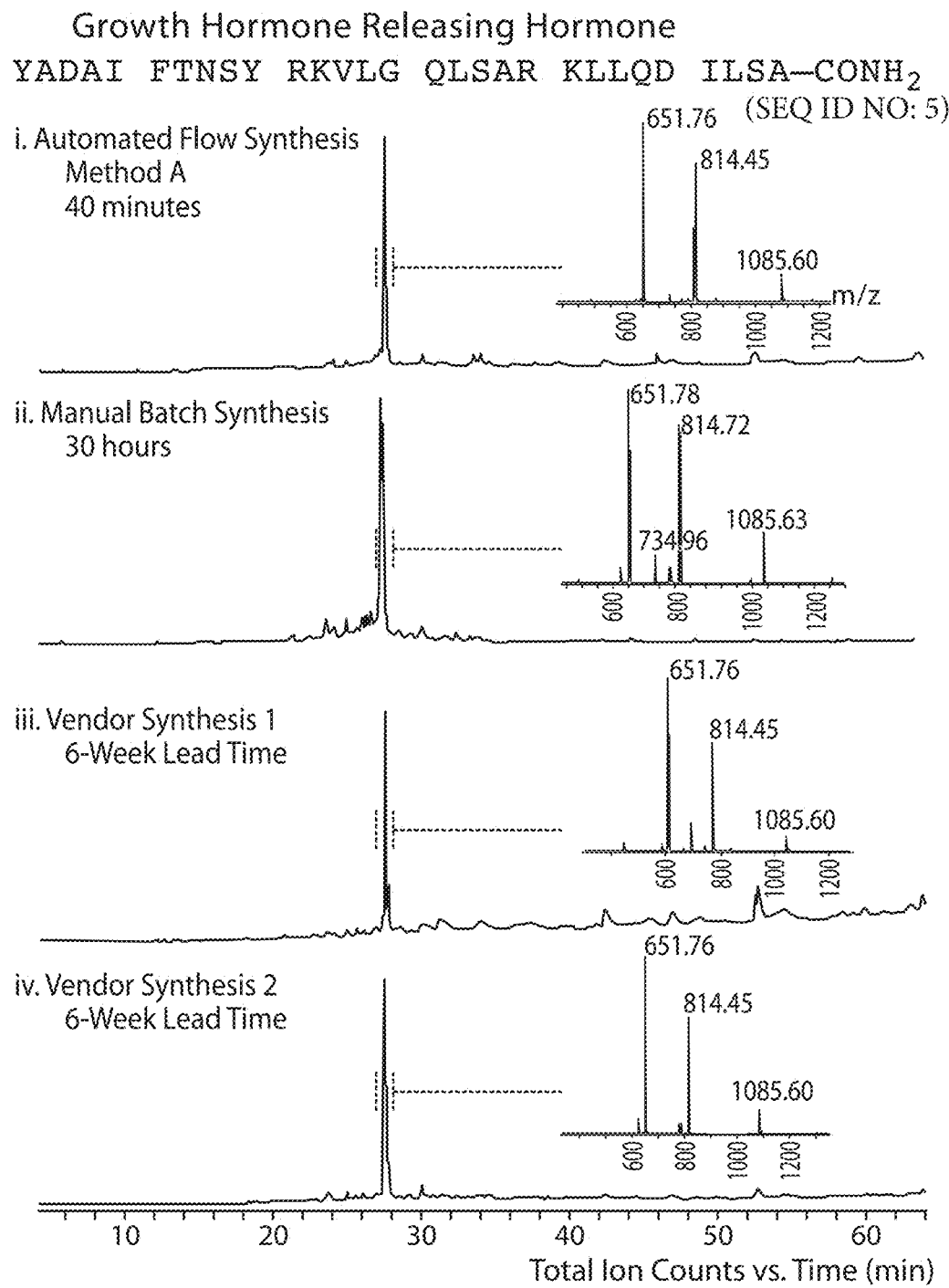
FIG. 9A is a LC-MS chromatograph for Growth Hormone Releasing Hormone (GHRH) synthesized via different methods, according to one set of embodiments.
Figure 9B:
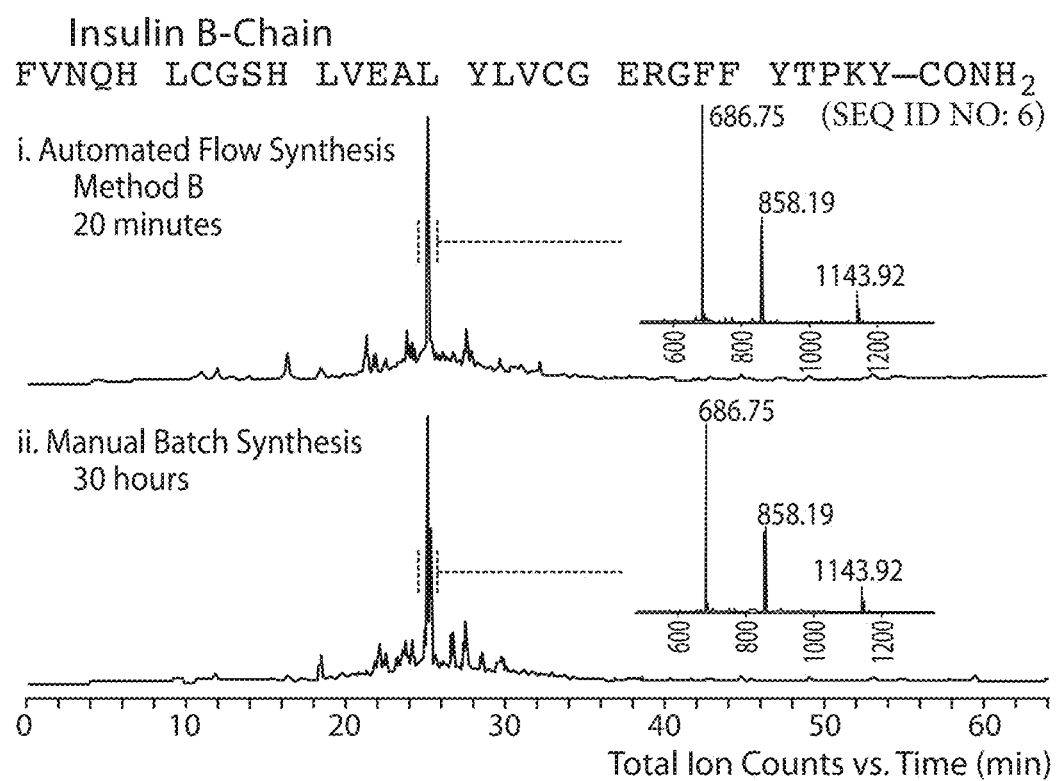
FIG. 9B is a LC-MS chromatograph for Insulin B-chain synthesized using different methods, according to one set of embodiments.
Figure 9C:
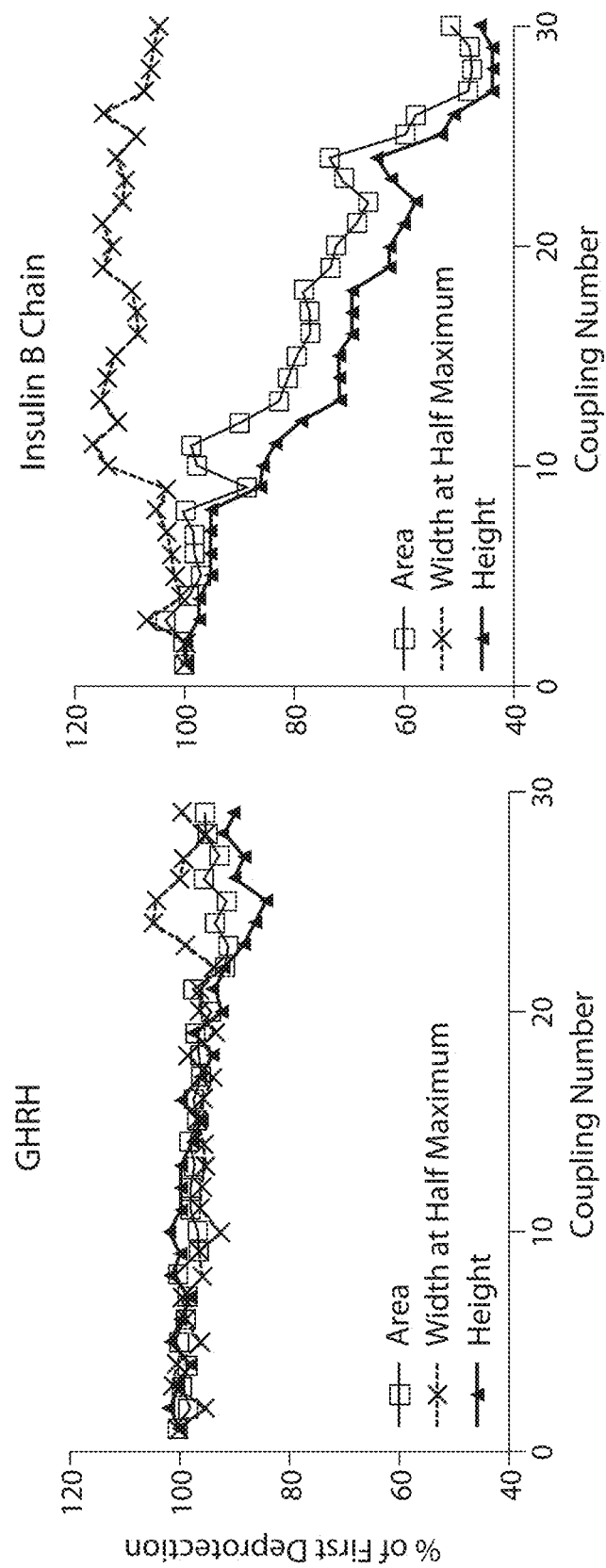
FIG. 9C is a plot of Fmoc deprotection UV data for each cycle of synthesis for GHRH and Insulin B-chain, according to one set of embodiments.

The AFPS was initially validated by synthesizing test peptides ALFALFA and a fragment of acyl carrier protein ($ACP_{65-74}$) as shown in FIG. 8D. These peptides were synthesized in high yield with low levels of side products. A comparative study was then performed between longer peptides produced by the AFPS, batch synthesis, and reputable custom peptide vendors, as shown in FIGS. 9A-9B. Compared to standard batch methods, peptide synthesis using high-speed continuous flow activation at elevated temperatures allowed for comparable or higher quality synthesis of long polypeptides in a fraction of the time. Additionally, as shown in FIG. 9C, in-process UV monitoring gave information about the synthetic yields of each step. The steady decrease in peak area observed for the insulin B chain resulted from chain-terminating side reactions. These byproducts appeared as a series of impurities around the main peak in the LC-MS chromatogram.

The epimerization of Cys and His with high-temperature flow activation was then assessed. When activated, Cys and His can lose stereochemistry at the Cα position. This problem bedevils batch synthesis techniques, especially at elevated temperature, because activation, coupling, and degradation all happen simultaneously in the same vessel. On the batch microwave synthesizer, if has been found coupling Fmoc-L-Cys(Trt) for 1.5 minutes at 90° C. under microwave irradiation with HBTU and DIEA causes 16.7% of the undesired D-Cys product to form. In contrast, it was found that continuous flow allows the activation process to be controlled by the amount of time in the heated zone of the system. To probe this, two model peptides FHL and GCF, whose diastereomers can be separated and quantified by LC-MS were used. By increasing the flow rate, and therefore decreasing the residence time at temperature of activated Fmoc-Cys(Trt) and Fmoc-His(Boc), the diastereomer formation was limited for AFPS method B to 0.5% for FHL and 3% for GCF. This level of diastereomer formation is consistent with optimized room temperature batch synthesis protocols.

Finally, the synthesis of "difficult" peptides was investigated. With such sequences, the kinetics of coupling and deprotection slow down, resulting in deletion and truncation products. It has been hypothesized that difficult peptides result from aggregation of the growing peptidyl chain. However, the identification of difficult sequences requires time-intensive procedures including LC-MS analysis, quantitative ninhydrin tests, or Kaiser tests. By contrast, it was discovered that analysis of Fmoc removal by UV absorbance under continuous flow conditions offers a quick, quantitative measure of the success of peptide assembly and the aggregation state of the resin-bound peptide.

Figure 10A:
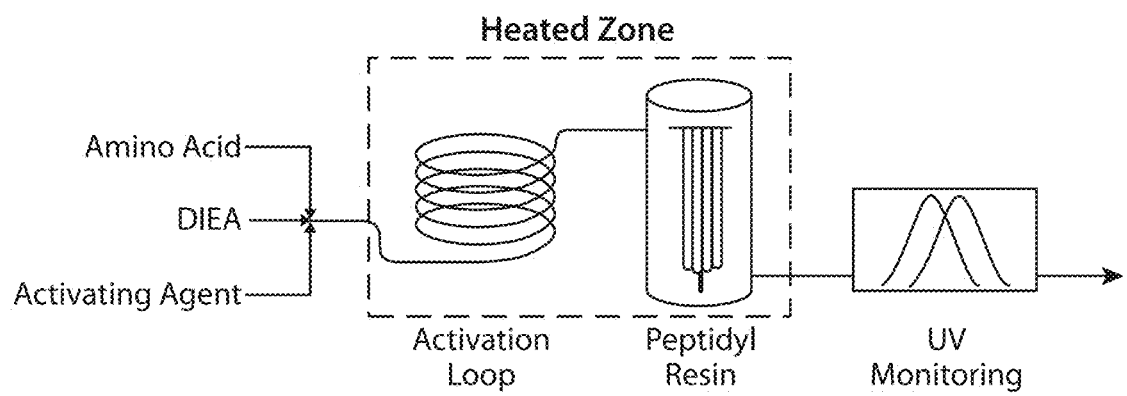
FIG. 10A is a diagram of the heated portion of the automated flow peptide synthesizer, according to one set of embodiments.
Figure 10B:
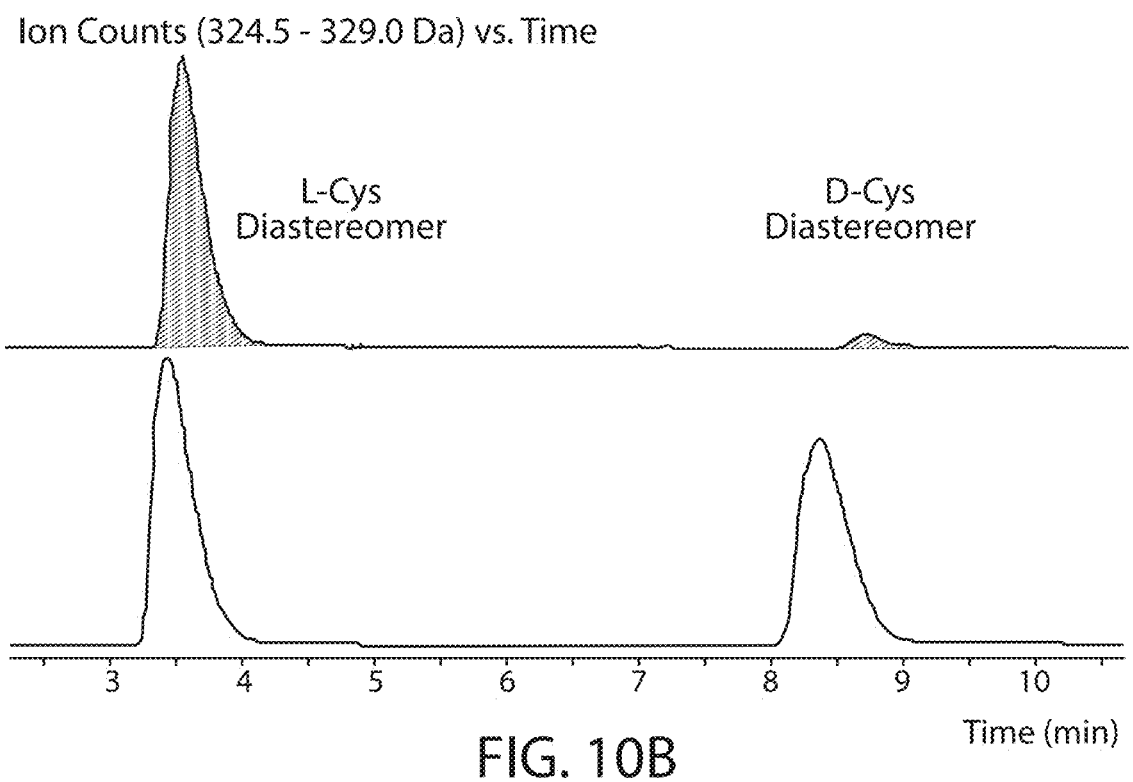
FIG. 10B is a diastereomer analysis of model peptide GCF showing a representative sample from flow synthesis using method B (top) and a 50/50 mixture of the authentic Cys diastereomers (bottom), according to one set of embodiments.
Figure 10C:
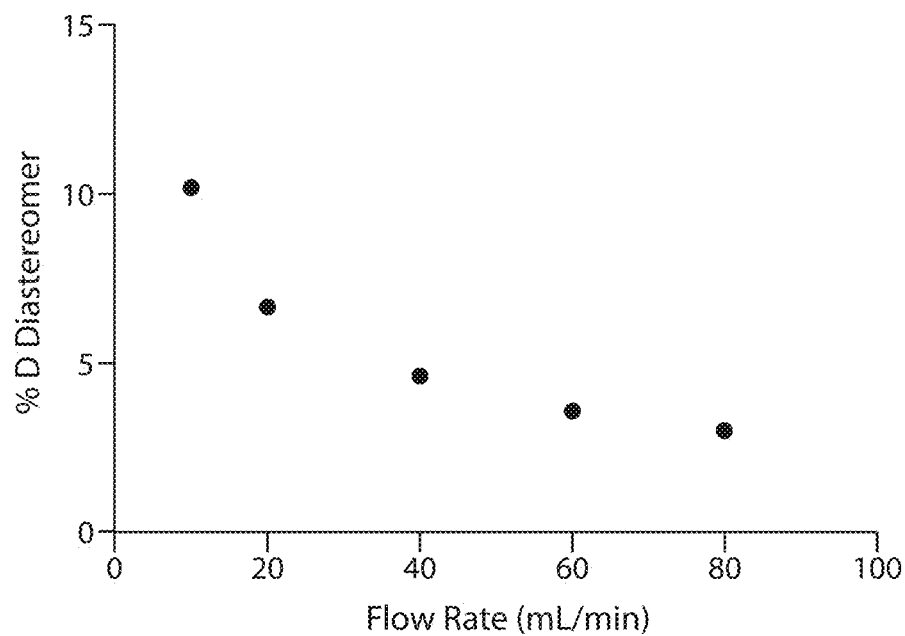
FIG. 10C is a graph of the percentage of Cys diastereomer formation as a function of flow rate (ml/min) using method B, according to one set of embodiments.
Figure 10D:
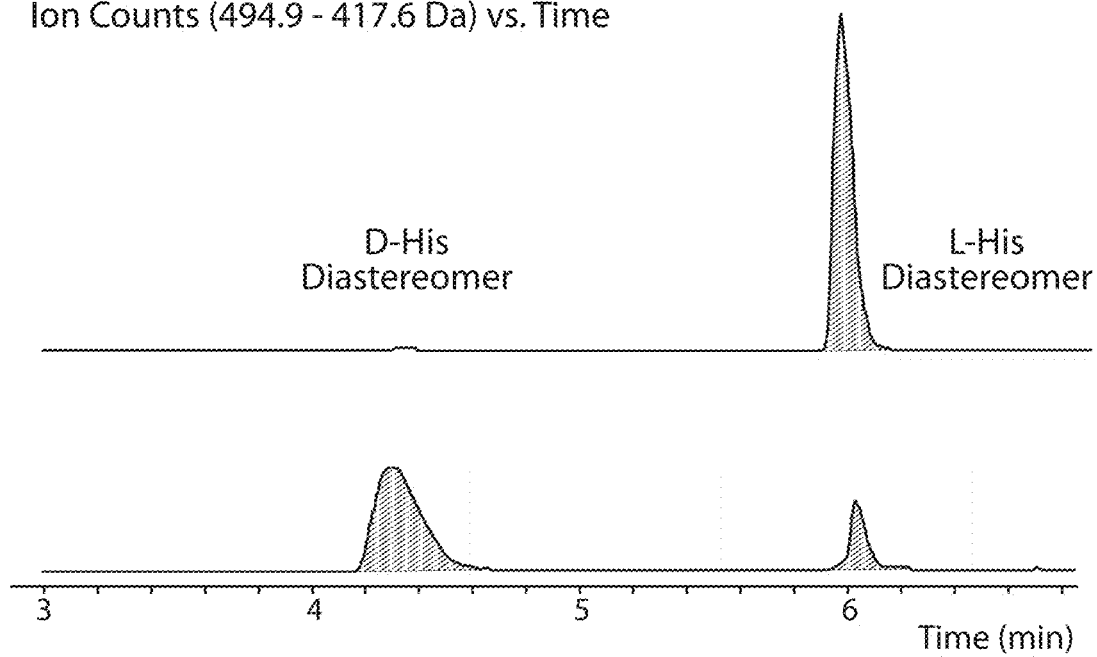
FIG. 10D is a diastereomer analysis of model peptide FHL showing a representative sample from flow synthesis using method B (top) and a 50/50 mixture of the authentic Cys diastereomers (bottom), according to one set of embodiments.
Figure 10E:
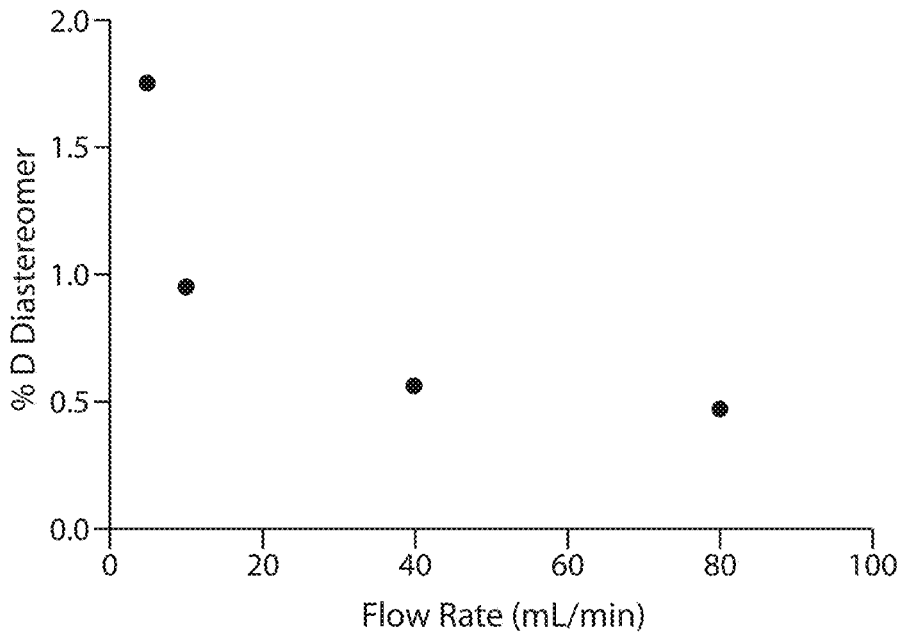
FIG. 10E is a graph of the percentage of histidine diastereomer formation as a function of flow rate (ml/min)

To study the effectiveness of UV monitoring, the Jung-Redmann (JR) 10-mer was used as a difficult peptide. To start, batch SPPS of this peptide was performed at room temperature and it was found that the synthesis began to fail at the sixth coupling, yielding large amounts of Trp, Phe, and Thr deletion as shown in FIG. 10E. Next, using the AFPS, this polypeptide was synthesized at 90° C. and the curves for Fmoc removal after each amino acid addition were examined. As depicted in FIGS. 10A and 10B, the area under each deprotection curve was constant until a sharp decrease during the final deprotection. LC-MS of the product revealed that the major byproduct was a Trp deletion, highlighting that higher temperature eliminated the Phe and Thr deletions observed in the batch case. The full width at half maximum of the deprotection peaks broadened by almost 20% during latter couplings, suggesting either a slowing of Fmoc removal or a reduced rate of diffusion through the aggregated peptide, and serving as a harbinger of the final deletion.

UV readout was used to minimize Trp deletion. One way to mitigate peptide aggregation during synthesis is to lower resin substitution; therefore, a set of amine reduced resins was prepared and the Fmoc removal signals during chain assembly was monitored. As shown in FIG. 10C, at reduced loading, the observed decrease in peak area for the final Trp coupling became less pronounced and pointed toward the optimal loading of 0.3 mmol/g, in line with Merrifield's observation. Equally important, it was found that, for this deletion product, the UV readout corroborated the LC-MS data as shown in FIG. 10C-10F.

The method described in this example offers numerous advantages over manual flow synthesis, thermally-accelerated batch synthesis, and other continuous flow peptide synthesis methods. First, automation of the entire process of heating, mixing, and activation of amino acids in a mix-and-match format enables endless possibilities to tune chemistry on a residue-by-residue basis. Second, inline mixing of these reagents with precise pump and valve actuation allows for control of stoichiometry, residence time, and amino acid epimerization, making the synthesis highly reproducible. Third, in-flow UV monitoring and data collection allow relative quantitation of Fmoc removal for each cycle which correlates with amide coupling efficiency. Fourth, maintaining a high flux of wash solvent, deprotection agent, and activated amino acid at steady state over the resin bead significantly improved peptide synthesis.

FIG. 8A shows a photograph of the automated flow solid phase synthesizer, highlighting the different system modules and a process flow diagram. Amino acid, activating agent and DIEA are merged together by three HPLC pumps. A series of multiposition valves controls the selection of the amino acid and activating agent. Amino acid activation occurs by flow through one of several heated flow paths determined by the position of a column selector valve. Activated amino acid is then flowed over a resin bed containing 200 mg of peptidyl resin housed in a 6-mL fritted polypropylene syringe that is sheathed by a heated jacket. The waste effluent is passed through a UV-visible spectrometer and then to waste. FIG. 8B shows a cycle diagrams showing the duration of each step, the solution composition during each step after mixing, and the total volume of reagent used at each step. FIG. 8C shows LC-MS data for the crude product of acyl carrier protein (65-74) synthesis using Method B, synthesized in 44% isolated yield. For this synthesis, 200 mg of starting peptidyl resin yielded 314 mg of dried resin. Throughout this work, isolated crude peptide yields are based on the nominal loading of resin. FIG. 8D shows an example of UV absorbance data for one coupling and deprotection cycle.

FIG. 9A shows LC-MS data Growth Hormone Releasing Hormone synthesized via different methods. Growth hormone releasing hormone was synthesized in (i) 40 minutes with method A in 58% isolated yield, compared to (ii) 30 hours using manual batch techniques with a 60% isolated yield. This peptide was also purchased from two vendors (iii, iv) with a 6-week lead time. Cleavage of 200 mg of each of these peptidyl resins yielded 76 mg and 90 mg, amounts comparable to automated and manual syntheses. FIG. 9B shows LC-MS data for Insulin B-chain synthesized using different methods. The insulin B-chain was synthesized in 20 minutes using Method B in 53% isolated yield, compared to 30 hours and in 45% yield with manual batch techniques. FIG. 9C shows a plot of Fmoc deprotection UV data for each cycle of synthesis for GHRH and Insulin B-chain. Peak area, full-width half maximum, and peak maximum is plotted as a function of coupling number. Liquid chromatography and ESI-MS was performed on an Agilent 1260 Infinity LC tethered to a 6520 QTOF mass spectrometer. Each sample was injected onto a Zorbax 300SB-C3 column pre-equilibrated with 5% acetonitrile in water with 0.1% formic acid. After a 4 minute hold, the acetonitrile concentration was ramped to 65% over 60 minutes.

FIG. 10A shows a diagram of the heated portion of the automated flow peptide synthesizer. FIG. 10B shows a diastereomer analysis of model peptide GCF showing a representative sample from flow synthesis using method B (top) and a 50/50 mixture of the authentic Cys diastereomers (bottom). FIG. 10B shows the percentage of Cys diastereomer formation as a function of flow rate (ml/min) using method B. FIG. 10D shows the same analysis as FIG. 3B for model peptide FHL to investigate His epimerization during flow activation. LC-MS of model peptide FHL synthesized using method B (top panel) and a 50/50 mixture of authentic His diastereomers (bottom). FIG. 10E shows the percentage of histidine diastereomer formation as a function of flow rate (ml/min).

Figure 11A:
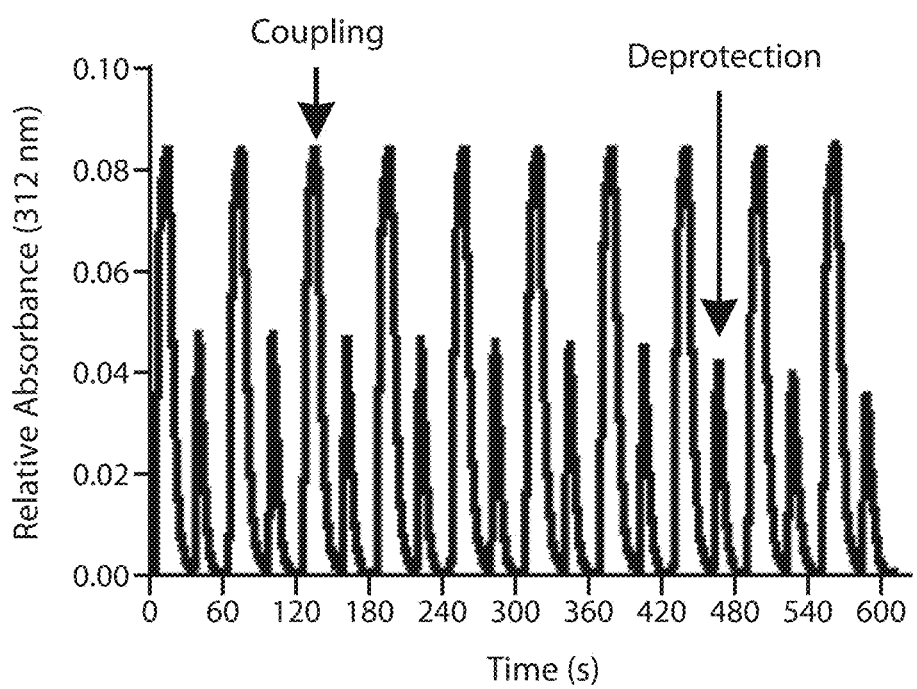
FIG. 11A is an UV absorbance spectrum as recorded for the initial synthesis of the JR 10-mer (WFTTLISTIM) using method B, according to one set of embodiments.
Figure 11B:
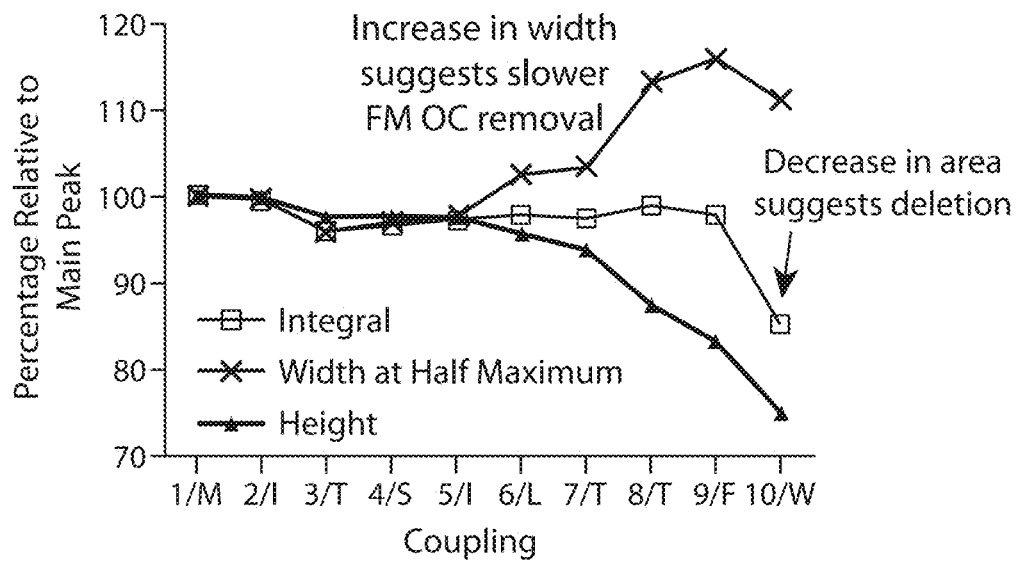
FIG. 11B is a graph of the percentage relative main peak versus coupling, according to one set of embodiments analysis, according to one set of embodiments.
Figure 11C:
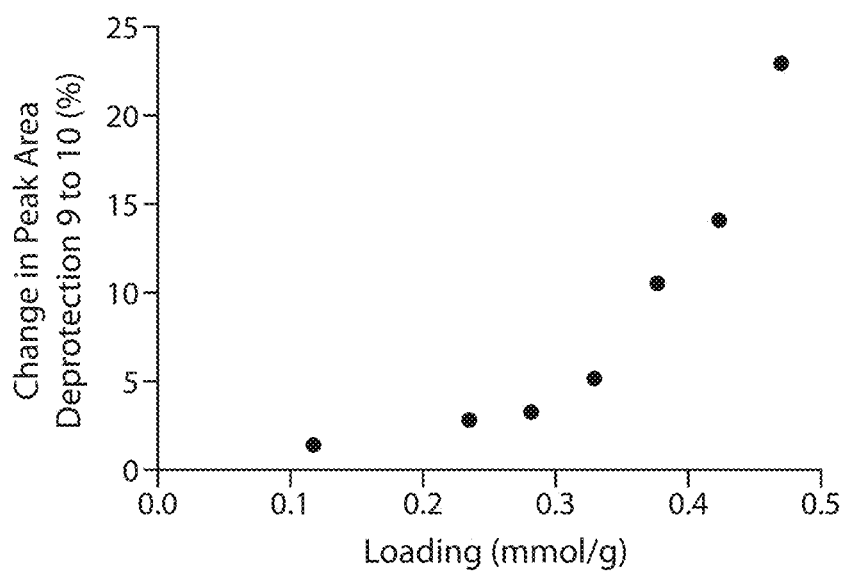
FIG. 11C is a plot of change of deprotection peak area from residue 9 to 10 from the UV absorbance spectrum as a function of resin loading, according to one set of embodiments.
Figure 11D:
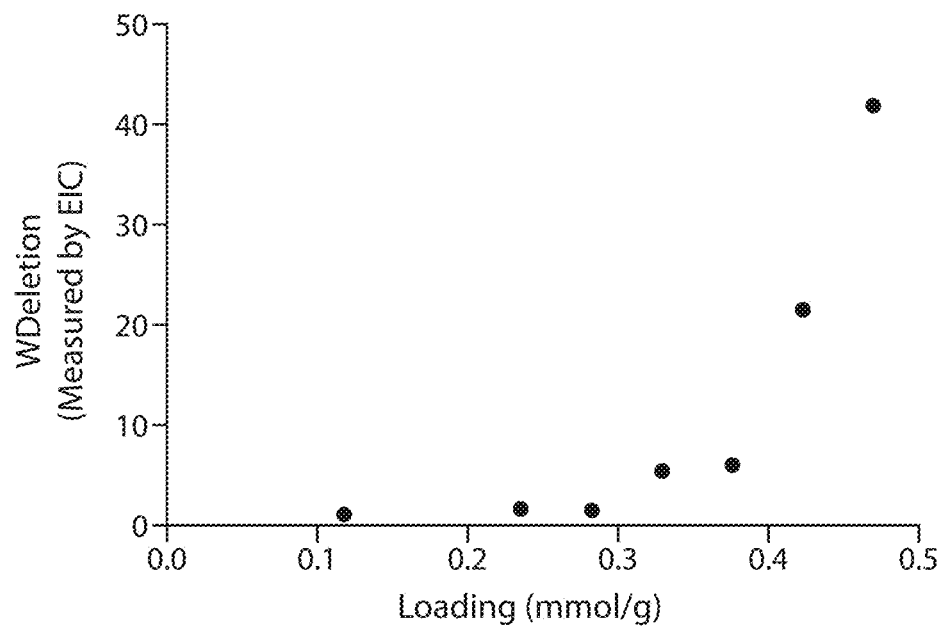
FIG. 11D is a plot of Trp deletion as a function of resin loading as determined from LC-MS, according to one set of embodiments.
Figure 11E:
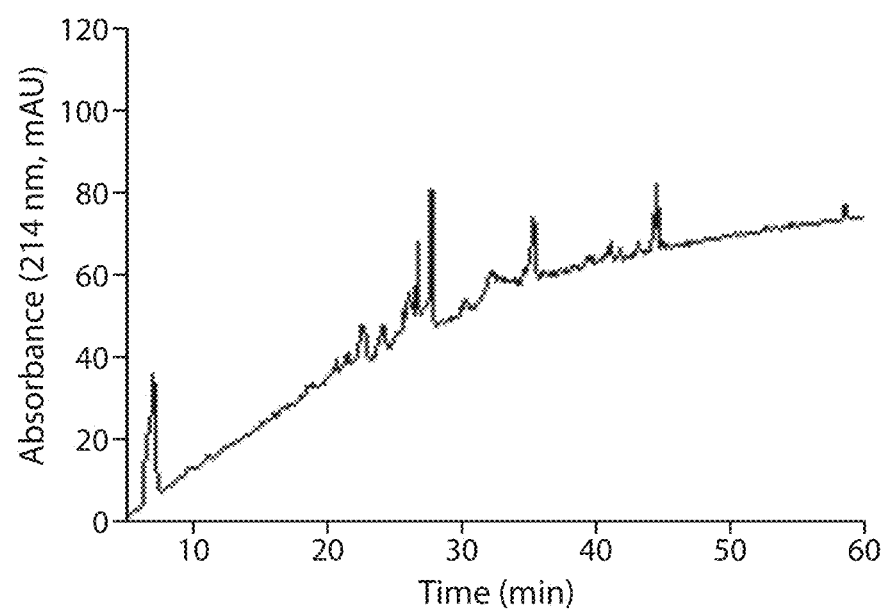
FIG. 11E is a LC-MS chromatogram of the final crude products for JR 10-mer prepared by manual batch with 0.45 mmol/g resin loading, according to one set of embodiments.
Figure 11F:
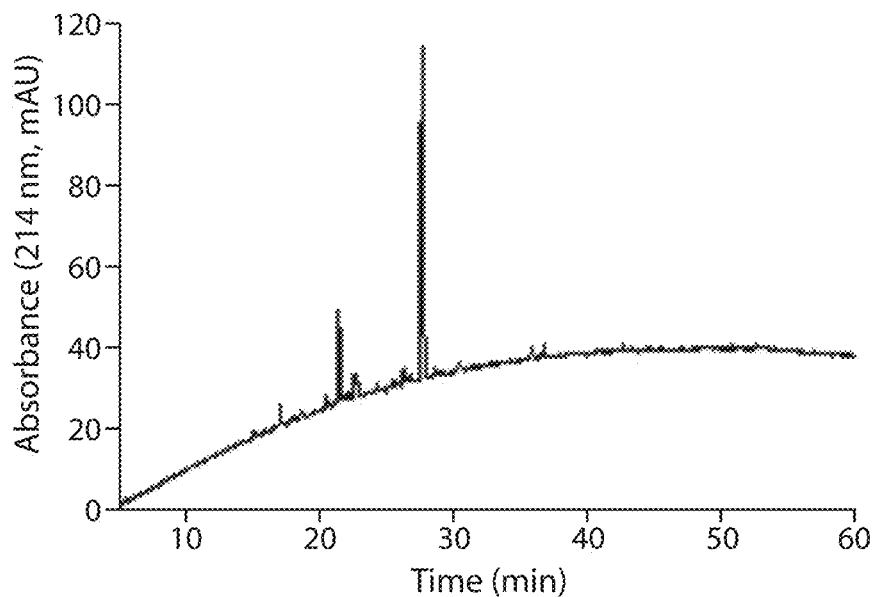
FIG. 11F is a LC-MS chromatogram of the final crude products for JR 10-mer prepared by automated flow with 0.45 mmol/g resin loading, according to one set of embodiments.
Figure 11G:
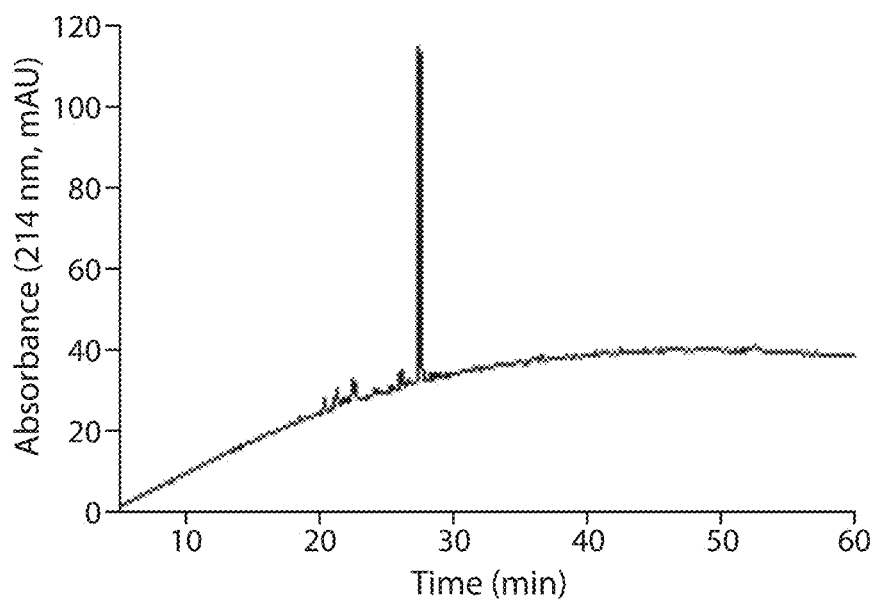
FIG. 11G is a LC-MS chromatogram of the final crude products for JR 10-mer prepared by automated flow with 0.27 mmol/g resin loading.

FIG. 11A shows UV absorbance data as recorded for the initial synthesis of the JR 10-mer (WFTTLISTIM (SEQ ID NO: 2)) using method B. FIG. 11B shows the analysis of the Fmoc removal UV peaks. The analysis revealed that peak width gradually increases after the 4th coupling, while peak area stays constant until the last coupling. FIG. 11C shows a plot of change of deprotection peak area from residue 9 to 10 from the UV absorbance data as a function of resin loading. FIG. 11D shows a plot of Trp deletion as a function of resin loading as determined from LC-MS. The amount of deletion measured by LC-MS corroborates the amount of deletion predicted by the UV in-process measurement. FIG. 11E-11G show LC-MS chromatograms of the final crude products for JR 10-mer prepared by manual batch with 0.45 mmol/g resin loading (E), automated flow with 0.45 mmol/g resin loading (F), and automated flow with 0.27 mmol/g resin loading (G).

Example 3

This example describes the materials, methods, and instrumentation used in Example 2.

Materials: All reagents were purchased and used as received. Fmoc amino acids were purchased from Creo Salus. Fmoc-His(Boc)-OH and O-(7-Azabenzotriazol-1-yl)-N,N,N',N'-tetramethyluronium hexafluorophosphate (HATU) was purchased from ChemImpex. Omnisolv grade N,N-dimethylformamide (DMF) was purchased from EMD Millipore (DX1726-1). Diisopropylethylamine (DIEA, catalog number 387649), piperidine, trifluoroacetic acid, triisopropylsilane, acetonitrile and 1,2-ethanedithiol (EDT) were purchased from Sigma Aldrich. H-Rink Amide ChemMatrix polyethylene glycol resin was purchased from Pcas Biomatrix (catalog number 1744).

Reagent Storage and Fluidic Manifold: The reagent storage system used two different vessels to contain reagents: a Chemglass three-neck 500 mL spinner flask for large volumes (CLS-1401-500), and 50 mL polypropylene syringe tubes for smaller volumes (parts #AD930-N, AD955-N). All of the glass bottles were painted with a UV-resistant matte spray paint (Krylon 1309) to reduce UV degradation of the reagents and had a green protective safety net for operation under argon pressure. The argon pressure was maintained at 5 psi pressure with a Swagelok pressure regulator (part #KCP1CFB2B7P60000). The reagent withdraw lines were outfitted with a 20 um polypropylene filter (part #JR-32178) to prevent clogging of pumps, check valves, and lines from any reagent crystallization or impurities.

Each row of 9 amino acid bottles and syringes fed into a VICI Valco 10-position valve (Vici part #C25-3180EUHA) where the tenth position was DMF. Those valves all fed into a main Vici Valco 10 position valve. This main valve fed the amino acid pump. Bottles containing HATU, other coupling agents, 40% piperidine, and DMF fed into a separate 10-position valve. This valve was connected to the coupling agent pump. DIEA feeds directly into the third pump.

Pumping and Mixing: The AFPS operated with three Varian Prostar 210 pumps. The first pump delivered either an amino acid or DMF. The second pump delivered either a coupling agent, 40% piperidine solution, or DMF. The third pump delivered DIEA. The coupling agent and amino acid pumps had a 50 ml/min stainless steel pump head (Agilent part #50-WSS). The DIEA pump had a 5 ml/min pump head (Agilent part #5-Ti). The three pumps outlets merged at a cross (IDEX part #P-722) with three inlet check valves (IDEX part #CV-3320) to prevent diffusion between the cross and pump head. The lengths of PEEK tubing (1/16" OD, 0.020" ID) between the PEEK cross and all of the pumps had matched volumes. After the cross, a length FEP tubing (1/16" OD, 0.030"ID) was coiled 22 times around a ½ inch cylinder to form a high dean number (>3000) static mixer to facilitate reagent mixing.

Activation and Coupling Reactors: After mixing, the reagent stream proceeded to a heat exchanger that was selected using a VICI Valco six-position column selector valve (Vici part #ACST6UW-EUTA). These heat exchangers consisted of a length of stainless steel tubing wrapped around an aluminum spool and coated with silicone for insulation. The spools were heated with two resistive cartridge heaters (Omega part #CSS-10250/120V). For peptide synthesis method A, a 3 m (10 ft, 1.368 ml) heat exchanger loop at 90° C. was used; for peptide synthesis method B, a 1.5 m (5 ft, 0.684 ml) heat exchanger loop at 70° C. was used.

Prototyping on Arduino: Initially, the control system was prototyped on an Arduino Mega. The pumps and valves were daisy chained and connected to separate TTL serial ports on the Arduino using the RS232 MAX3232 SparkFun Transceiver Breakout (BOB-11189)

Serial Communication with Pumps and Valves: Standard RS-485 serial protocols were used for communication with the Varian ProStar 210 pumps and VICI Valco valves. Pump communication was at 19200 baud, 8 bit, even parity, with 1 stop bit. Valve communication was at 9600 baud with no parity and one stop bit.

Heating and Temperature Control: All heaters were controlled with an 8-channel Watlow EZ-Zone RM controller (part number RMHF-1122-A1AA). This controller integrates PID control on-board. Temperatures were read into the software through the RS-232 serial port using software provided by Watlow. All thermocouples were calibrated using a single point calibration at 0 degrees Celsius.

Process Data Collection: The software recorded temperature, mass flow rate, pressure, and UV absorbance during each synthesis. The Watlow PID control unit described above was used to acquire temperature data. For mass flow data, a Bronkhorst Coriolis mass flow meter was used (part

M14-XAD-11-0-5) and also allowed monitoring of fluid density. The differential pressure across the reactor was monitored using two DJ instrument HPLC through-bore titanium pressure sensors (part #DF2-01-TI-500-5V-41"). These sensors were single point calibrated at 90 degrees Celsius at 100 psi.

UV monitoring at 312 nm was accomplished by using a Varian Prostar 230 UV-Vis detector fitted with a super prep dual path length flow cell (nominal path lengths of 4 mm and 0.15 mm). This dual path length flow cell setup allowed for high dynamic range absorbance measurements—whenever the absorbance increased past the linear range for the large flow cell, the instrument switched to recording the absorbance through the smaller flow cell. In order to assure accurate measurements during the flow cell switchover, the ratio of path lengths was calibrated using a standard solution of dibenzofulvene prepared as described in Letters in Peptide Science, 9: 203-206, 2002.

Temperature and mass flow data were acquired through serial communication with the Watlow PID and Bronkhorst flow meter. Electronic voltage measurements for pressure and UV data were obtained from the instrument using a National Instruments NI cDAQ-9184 (part number 782069-01) with a NI 9205 32-channel analog input card (part number 779357-01). Data points were recorded with averaging every 50 ms. On the UV detector, the signal response time was set to 10 ms and the full voltage scale was 100 my.

The software allowed for customization of amino acid, activating agent, temperatures of the coupling and deprotection steps, flow rate of the coupling and deprotection steps, and the amount of reagents used (number of pump strokes). These could be modified while the system was in operation: for instance, in response to UV that suggested aggregation, the temperature, the amount of amino acid used, or the activating agent could be changed.

The synthesizer was controlled over Ethernet and USB on a Windows computer with a LabView VI. The VI has a graphical interface to allow a user to easily create a recipe for the desired peptide. Recipes allow users to control the flow rate, the amount of amino acid used, the activating agent, the temperature and residence time of activation, the deprotection residence time, and the amount of deprotection reagent for each step of the synthesis. Once, the user has created the desired recipe, he or she submits it to the machine queue and presses "Run." If during the synthesis the user noticed a change in the synthesis quality by monitoring the UV trace, he or she could modify the recipe for any subsequent coupling step on the fly. When "Run" is pressed, the software populates the predefined routine for each amino acid with the users selected amino acid, flow rates, temperatures, amount of reagents, and type of activating reagent.

The code consisted of operations performed on either pumps, valves, or motors. Each operation consisted of a set of inputs and a dwell time. Valves accept a valve ID and valve position; pumps accept a pump ID and pump flow rate; motors accept a motor ID and motor position. After a step was complete, the program waited until completion of the dwell time before executing the next step. Dwell times represented by #variables are computed on the fly using the recipe input. For instance, the dwell time after actuation of the pumps in step 12 is determined by the "CPL NStrk" (number of coupling strokes) parameter in the recipe. Table 1 shows a program for the assembly of a single amino acid peptide.

Analytical Peptide Cleavage and Side Chain Protecting Group Removal: Approximately 10 mg of peptidyl resin was added to a 1.5 mL Eppendorf tube. 200 µL of cleavage solution (94% TFA, 1% TIPS, 2.5% EDT, 2.5% water) was added to the tube and incubated at 60° C. for 5 minutes. After completion of cleavage, 200 µL TFA was added to the tube to rinse the resin, and as much liquid as possible was transferred into another tube using a pipet tip, avoiding resin. To the tube of cleavage solution, 800 µL cold diethyl ether was added. The tube was shaken—a visible waxy precipitate formed and was collected by centrifugation. The supernatant ether was poured off and two more ether washes were performed.

Finally, the waxy solid was allowed to dry briefly under a stream of nitrogen gas. 500 µL of 50% acetonitrile in water was added to the tube and mixed thoroughly. This solution was filtered through a centrifugal basket filter and diluted 1:10 in 50% acetonitrile in water with 0.1% TFA for the liquid chromatographic analysis.

Preparative Peptide Cleavage: After synthesis, peptidyl resin was washed with dichloromethane, dried in a vacuum chamber, and weighed. The resin was transferred into a 15 mL conical polypropylene tube. Approximately 7 mL of cleavage solution (94% TFA, 1% TIPS, 2.5% EDT, 2.5% water) was added to the tube. More cleavage solution was added to ensure complete submersion. The tube was capped, inverted to mix every half hour, and was allowed to proceed at room temperature for 2 hours.

Then, the resin slurry was filtered through a 10 µm polyethylene membrane disk fitted into a 10 mL Torviq syringe. The resin was rinsed twice more with 1 mL TFA, and the filtrate was transferred into a 50 mL polypropylene conical tube. 35 mL ice cold diethyl ether were added to the filtrate and left to stand for 30 minutes to precipitate the peptide. The precipitate was collected by centrifugation and triturated twice more with 35 mL cold diethyl ether. The supernatant was discarded.

Finally, residual ether was allowed to evaporate and the peptide was dissolved in 50% acetonitrile in water. The peptide solution was frozen, lyophilized until dry, and weighed.

Analytical Liquid Chromatographic Analysis of Peptide Samples: 1 µL of the diluted peptide sample was analyzed on an Agilent 6520 LC-MS with a Zorbax 300SB-C3 column (2.1 mm×150 mm, 5 µm particle size). For samples in FIG. 9 and FIG. 11, a gradient of acetonitrile in water with a 0.1% formic acid additive was used. Gradients started at 5% acetonitrile and ramped to 65% acetonitrile at a rate of 1% acetonitrile per minute. The full method included a hold time at 1% along with total time of gradient Initial Synthesis Conditions and System Characterization: At 20 mL·min-1 total system flow rate and at 70° C., treatment with 20% piperidine was chosen to be 20 s, conditions that were previously shown to be sufficient for complete Fmoc removal. The DMF washes were chosen to be 30 s. The washout time was verified by introducing Fmoc amino acid into the reactor and using the UV detector to ensure that the system was cleared of any UV active material after the DMF wash.

The scheme for in-line mixing the fluid streams of activating agent and the amino acid allowed for versatility in the conditions used for coupling. However, it required a departure from the conditions traditionally used for aminoacylation in Fmoc synthesis. Typically, reagents are used at their solubility limits, around 0.4M for Fmoc amino acids and uronium coupling agents. However, because these reagents were stored separately on the AFPS and coupling involved mixing two concentrated solutions, the final solution used for aminoacylation at the outset was composed of 0.2M amino acid and activating agent. For the typical coupling, a total of 9.6 mL of this coupling solution was used to ensure complete coupling. These conditions were initially tested for the synthesis of a short polypeptide, ALFALFA.

Optimization of Synthesis Cycle: A 10-residue peptide that is typically used as a diagnostic "difficult" sequence, ACP, was synthesized at 70° C., using the same volume of coupling reagent in each experiment, at 20, 40, and 60 mL/min total flow rate. At higher flow rates, the increasing formation of a chain termination side product—a tetramethylguanidyl truncation during the glutamine coupling was observed. It was hypothesized that this was due to incomplete activation at elevated flow rates: when the amounts of activating agent and amino acid are nearly equal, there could be residual HATU present which can guanidinylate the N-terminus of the growing peptidyl chain. Reducing the concentration of activating agent to 0.34M, as well as ensuring full synchronization of the pump heads eliminated this side reaction in most cases, allowing us to synthesize ACP at 80 mL/min in quantitative yield. For Fmoc-Arg couplings in other peptides, these truncations were still observed, so PyAOP was used as the activating agent for these couplings.

Investigation of Temperature Effect on Deprotection: The deprotection of Fmoc-Glycine-functionalized peptidyl resin with 20% piperidine at 70, 80, and 90° C. was examined. In all three cases, Fmoc-Gly was coupled to 200 mg of ChemMatrix Rink Amide resin at room temperature using batch coupling methods. The resins were then transferred to the automated flow synthesizer, where a single treatment of 20% piperidine was performed at either 70, 80, or 90° C. In all three cases, the integrated area of the Fmoc removal peaks was the same, suggesting complete Fmoc removal. However, at higher temperatures, the peak maximum occurs earlier, suggesting either faster deprotection, faster diffusion of the Fmoc-dibenzofulvene adduct out of the resin, or both.

Representative Protocol for Synthesis of Peptides on the Automated Flow Peptide Synthesizer: 200 mg of ChemMatrix PEG Rink Amide resin was loaded into a 6 mL Torviq fritted syringe fitted with an additional 7-12 µm Porex UHMWPE (XS-POR-7474) membrane on top of the frit. The resin was preswollen with DMF for 5 minutes, after which large resin aggregates were manually broken up by inserting the syringe plunger. The syringe was filled with DMF, loaded onto the fluidic inlet, and loaded into a 90° C. heated chamber. The synthesizer was set up as shown in FIG. 8, with all reagents pumped at a total flow rate of 80 mL·min-1 though a cross manifold, a mixer, and a 10 ft stainless steel heated loop at 90° C. before being pumped over the resin. Three Varian Prostar 210 HPLC pumps were used, two with 50 mL·min-1 pump heads for amino acid and activating agent, and one with a 5 mL·min-1 pump head, for diisopropylethylamine (DIEA). The 50 mL·min-1 pump head pumped 400 µL of liquid per pump stroke; the 5 mL·min-1 pump head pumped 40 µL of liquid per pump stroke.

The standard synthetic cycle used involved a first step of prewashing the resin at elevated temperatures for 20 s at 80 mL/min. During the coupling step, three HPLC pumps were used: a 50 mL·min-1 pump head pumped the activating agent (typically 0.34 M HATU), a second 50 mL·min-1 pump head pumped the amino acid (0.4M) and a 5 mL·min-1 pump head pumped diisopropylethylamine (DIEA). The first two pumps were activated for 5 pumping strokes in order to prime the coupling agent and amino acid before the DIEA pump was activated. The three pumps were then actuated together for a period of 7 pumping strokes, after which the activating agent pump and amino acid pump were switched using a rotary valve to select DMF. The three pumps were actuated together for a final 5 pumping strokes, after which the DIEA pump was shut off and the other two pumps continue to wash the resin for another 16 pump strokes.

During the deprotection step, two HPLC pumps were used. Using a rotary valve, one HPLC pump selects 40% piperidine and the other selects DMF. The pumps were activated for 13 pump strokes. After mixing, the final concentration of piperidine is 20%. Next, the rotary valves select DMF for both HPLC pumps, and the resin was washed for an additional 16 pump strokes. The coupling/deprotection cycle was repeated for all additional monomers.

Aspartimide Formation and Elevated Temperature GHRH Synthesis: GHRH synthesis at 70° C. as shown in FIG. 6 and at 90° C. was investigated. When performing this synthesis at 90° C., as opposed to 70° C., formation of an aspartimide byproduct with a signature −18 Da mass and shifted retention time was noticed. This side reaction is known to happen both at elevated temperature and with particular Asp-containing peptides. The effect of piperazine, a milder base, on this side reaction was investigated. Use of 2.5% piperazine instead of 20% piperidine for the deprotection significantly reduced the amount of this side product as measured by LC-MS, but increased the amount of amino acid deletions, particularly Ala and Leu. Addition of 0.1 M HOBt to the 2.5% piperazine deprotection cocktail resulted in roughly the same synthesis quality. For Asp-containing peptides where aspartimide formation is suspected, it is therefore advantageous to use either reduced temperature, a reduced strength deprotection cocktail, or both.

Synthesis of Reduced Loading Resin and JR 10-mer Loading Study: Reduced loading resins were prepared by coupling the first amino acid, Fmoc-Met-OH, to 200 mg of ChemMatrix Rink Amide HR resin, which has a nominal loading of 0.45 mmol/g. For one batch of resin, 1 mmol of Fmoc-Met-OH was mixed with 2.5 mL of a 0.4M HBTU, 0.4M HOBT solution and dissolved. 500 µL of DIEA was added, mixed thoroughly, and then added to the resin. Coupling was allowed to proceed for 1 hr. For the other four batches of resin, acetic acid was substituted stoichiometrically for Fmoc-Met-OH to reach the desired loadings: 90%, 80%, 70%, 60%, 50%, and 25% of the original loading. The relative loadings used in FIG. 11 were computed using the first deprotection integral.

Then, on the automated flow peptide synthesizer, the sequence WFTTLISTIM (SEQ ID NO: 2) was synthesized on each of these resins. The conditions were: 90° C. for the heat exchanger, reactor inlet, and reactor body. 80 mL/min coupling/deprotection, 7 coupling strokes, 13 deprotection strokes, 24 washing strokes. The first coupling—M—added nothing to the resin, as the resin was still fully protected. The first deprotection gave a baseline UV absorbance and allowed estimation of the loading obtained during the capping step.

Manual Synthesis of JR 10-mer, Insulin B chain, and GHRH: These peptides were synthesized according to Kent, et al., Org Lett. 2015, 17 (14), 3521. ChemMatrix Rinkamide resin (0.1 mmol; 0.45 mmol/g) was used. Amino acids were activated for 30 seconds by first dissolving 0.55 mmol of the amino acid to be coupled in 1.25 mL 0.4 M HBTU/0.4 M HOBT, and then adding 122 µL (0.7 mmol) of DIEA. After 30 seconds, the solution was added to the resin. The couplings were allowed to proceed for 30 minutes with intermittent stirring.

After each coupling step, a 45 mL DMF flow wash was performed. Then, 3 mL of 20% (v/v) piperidine was added to the resin, stirred, and allowed to incubate for 5 minutes. This process was repeated once. After each deprotection, a 45 mL flow wash was performed, followed by a 1 minute batch treatment with DMF.

Determination of Cys and His Epimerization: Cys and His epimerization were measured using the two model peptides GCF and FHL, respectively. For each synthesis, the flow rates for C and H coupling were varied, and the coupling conditions for the flanking residues (G and F for GCF; F and L for FHL) were kept constant at 90° C. and 80 mL/min total flow rate. After synthesis of each model peptide, cleavage was performed as described above.

LC-MS analysis of the cleaved product was performed. In order to determine the amount of D-epimer formed in each case, extracted ion chromatograms of the two stereoisomers were obtained: 342.5-329.0 Da for GCF and 494.9-417.6 Da for FHL. The peaks corresponding to each epimer were integrated. Authentic standards were prepared and analyzed on the same methods in order to verify the retention times of each epimer.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of operating a peptide synthesis system, comprising:
performing an amino acid addition cycle of a peptide synthesis process comprising a deprotection reaction, a coupling reaction, and one or more optional reagent removal steps;
detecting, during the amino acid addition cycle, an electromagnetic absorbance and/or an electromagnetic emission of a fluid stream at a detection zone positioned downstream of the reactor to produce a signal comprising a first peak;
determining whether improper resin loading and/or a mechanical failure has occurred during the coupling reaction based at least in part on a comparison between a property of the first peak and a corresponding property of a reference peak, wherein the reference peak is programmed into the peptide synthesis system; and
stopping the peptide synthesis process that included the amino acid addition cycle and starting a subsequent peptide synthesis process if the comparison indicates that improper resin loading and/or a mechanical failure has occurred during the coupling reaction.

2. The method of claim 1, wherein the coupling reaction is between an amino acid and an immobilized amino acid residue.

3. The method of claim 1, wherein the electromagnetic absorbance and/or the electromagnetic emission is selected from a group consisting of infrared absorbance, infrared emission, ultraviolet absorbance, and/or ultraviolet emission.

4. The method of claim 1, wherein the determining comprises comparing an area of the first peak to an area of the reference peak.

5. The method of claim 1, wherein the determining comprises determining whether improper resin loading and/or a mechanical failure has occurred during a coupling reaction based at least in part on a comparison between a property of the first peak, a corresponding property of the reference peak, and a corresponding property of a second reference peak that is part of a signal generated during an additional amino acid addition cycle.

6. The method of claim 1, wherein the determining comprises:
   determining that each of an area of the first peak and an area of the reference peak are below a value; and
   determining that a width of the first peak and a width of the reference peak are of a consistent size.

7. The method of claim 1, wherein the detecting, during the amino acid addition cycle, comprises detecting an electromagnetic absorbance of the fluid stream at the detection zone.

8. A method of operating a peptide synthesis system, comprising:
   performing an amino acid addition cycle of a peptide synthesis process to synthesize a peptide on a solid support in a reactor, the amino acid addition cycle comprising a deprotection reaction, a coupling reaction, and one or more optional reagent removal steps;
   detecting, during the amino acid addition cycle, an electromagnetic absorbance and/or an electromagnetic emission of a fluid stream at a detection zone positioned downstream of the reactor to produce a signal comprising a first peak;
   comparing a property of the first peak and a corresponding property of a reference peak, wherein the reference peak is programmed into the peptide synthesis system; and
   based at least in part on the comparing, stopping the peptide synthesis process that included the amino acid addition cycle and/or performing at least one of the following during a subsequent coupling reaction of a subsequent amino acid addition cycle, the subsequent coupling reaction corresponding to the coupling reaction of the amino acid addition cycle:
      increasing a residence time of an activating agent; and/or
      employing a different activating agent; and/or
      increasing a temperature of the reactor and/or the fluid stream; and/or
      employing a different stoichiometric ratio.

9. The method of claim 8, wherein the property of the first peak is an area of the first peak and the corresponding property of the reference peak is an area of the reference peak.

10. The method of claim 8, wherein the property of the first peak is a height of the first peak and the corresponding property of the reference peak is a height of the reference peak.

11. The method of claim 8, wherein the property of the first peak is a width of the first peak and the corresponding property of the reference peak is a width of the reference peak.

12. The method of claim 8, comprising:
   determining that each of an area of the first peak and an area of the reference peak that is part of a signal generated during the amino acid addition cycle are below a value;
   determining that a width of the first peak and a width of the reference peak are of a consistent size; and
   subsequently stopping the peptide synthesis process and starting a subsequent peptide synthesis process.

13. The method of claim 8, comprising:
   determining that each of an area of the reference peak is above a value while an area of the first peak is below the value;
   determining that a width of the first peak and a width of the reference peak, are of a consistent size; and
   subsequently, stopping the peptide synthesis process and/or performing at least one of the following during a coupling reaction of a subsequent peptide synthesis process, the coupling reaction of the subsequent peptide synthesis process corresponding to the coupling reaction of the peptide synthesis process:
      increasing a residence time of an activating agent; and/or
      employing a more reactive activating agent.

14. The method of claim 13, comprising:
   stopping the peptide synthesis process and starting a subsequent peptide synthesis process to synthesize the peptide if a change in area between the first peak and the reference peak is greater than 20%.

15. The method of claim 8, comprising:
   determining that an area of the reference peak is above a value, while an area of the first peak is below the value;
   determining that a width of the first peak and a width of the reference peak are of a consistent size; and
   subsequently stopping the peptide synthesis process and/or performing at least one of the following during a coupling reaction of a subsequent peptide synthesis process, the coupling reaction of the subsequent peptide synthesis process corresponding to the coupling reaction of the peptide synthesis process:
      employing a different activating agent; and/or
      employing a different stoichiometric ratio.

16. The method of claim 15, wherein the comparing comprises stopping the peptide synthesis process and starting a subsequent peptide synthesis process if a change in area between the first peak and the reference peak is greater than 30%.

17. The method of claim 8, comprising:
   determining that an area of the reference peak is above a value, while an area of the first peak is below the value;
   determining that a width of the reference peak and a width of the first peak are increasing starting from the width of the reference peak to the width of the first peak; and
   subsequently stopping the peptide synthesis process and/or increasing a temperature of the reactor and/or the fluid stream during a coupling reaction of a subsequent peptide synthesis process, the coupling reaction of the subsequent peptide synthesis process corresponding to the coupling reaction of the peptide synthesis process.

18. The method of claim 8, wherein comparing comprises:
   determining that an area of the first peak and an area of the reference peak are above a value;
   determining that a width of the reference peak and a width of the first peak are increasing starting from the width of the reference peak to the width of the first peak; and subsequently stopping the peptide synthesis process and/or increasing a temperature of the reactor and/or the fluid stream during a coupling reaction of a subsequent peptide synthesis process, the coupling reaction of the subsequent peptide synthesis-process corresponding to the coupling reaction of the peptide synthesis process.

19. A method of operating a peptide synthesis system, comprising:

performing an amino acid addition cycle of a peptide synthesis process to synthesize a peptide on a solid support in a reactor, the amino acid addition cycle comprising a deprotection reaction, a coupling reaction, and one or more optional reagent removal steps;

detecting, during the amino acid addition cycle, an electromagnetic absorbance and/or an electromagnetic emission of a fluid stream at a detection zone positioned downstream of the reactor to produce a signal comprising a first peak;

comparing a property of the first peak and a corresponding property of a reference peak, wherein the reference peak is programmed into the peptide synthesis system; and based at least in part on the comparing, increasing a temperature of the reactor and/or a fluid stream entering the reactor.

* * * * *